(12) United States Patent
Grinstaff et al.

(10) Patent No.: US 10,400,064 B2
(45) Date of Patent: Sep. 3, 2019

(54) GLYCEROL-BASED POLYCARBONATES

(71) Applicant: TRUSTEES OF BOSTON UNIVERSITY, Boston, MA (US)

(72) Inventors: Mark W. Grinstaff, Brookline, MA (US); Heng Zhang, Boston, MA (US); Iriny Ekladious, Bayonne, NJ (US); Marlena D. Konieczynska, Lawrenceville, NJ (US)

(73) Assignee: Trustees of Boston University, Boston, MA (US)

( * ) Notice: Subject to any disclaimer, the term of this patent is extended or adjusted under 35 U.S.C. 154(b) by 279 days.

(21) Appl. No.: 15/529,462

(22) PCT Filed: Nov. 25, 2015

(86) PCT No.: PCT/US2015/062648
§ 371 (c)(1),
(2) Date: May 24, 2017

(87) PCT Pub. No.: WO2016/086118
PCT Pub. Date: Jun. 2, 2016

(65) Prior Publication Data
US 2017/0369643 A1    Dec. 28, 2017

Related U.S. Application Data

(60) Provisional application No. 62/084,874, filed on Nov. 26, 2014.

(51) Int. Cl.
| C08G 64/34 | (2006.01) |
| C08G 64/42 | (2006.01) |
| A61K 47/59 | (2017.01) |
| A61K 31/337 | (2006.01) |
| C08G 64/02 | (2006.01) |

(52) U.S. Cl.
CPC ............ C08G 64/34 (2013.01); A61K 31/337 (2013.01); A61K 47/59 (2017.08); C08G 64/0208 (2013.01); C08G 64/42 (2013.01); C08G 2230/00 (2013.01)

(58) Field of Classification Search
None
See application file for complete search history.

(56) References Cited

U.S. PATENT DOCUMENTS

| 7,928,183 B2 | 4/2011 | Truong Dinh et al. |
| 8,247,520 B2 | 8/2012 | Allen et al. |
| 8,487,038 B2 | 7/2013 | Noordover et al. |
| 8,575,245 B2 | 11/2013 | Lapointe et al. |
| 2004/0086479 A1* | 5/2004 | Grinstaff .............. C08G 83/003 424/78.17 |
| 2006/0223973 A1 | 10/2006 | Hinz et al. |
| 2011/0172785 A1* | 7/2011 | Wolinsky ............. A61K 9/0024 623/23.72 |

OTHER PUBLICATIONS

Grinstaff et al.; J. Am. Chem. Soc.; 2013, 135, pp. 6806-6809; published Apr. 23, 2013.*
Coates et al., "Discrete Metal-Based Catalysts for the Copolymerization of CO2 and Epoxides: Discovery, Reactivity, Optimization, and Mechanism", Angewandte Chemie International Edition 43:6618-6639 (2004).
Cohen et al., "Cobalt Catalysts for the Alternating Copolymerization of Propylene Oxide and Carbon Dioxide: Combining High Activity and Selectivity", Journal of the American Chemical Society 127(31):10869-10878 (2005).
Lu et al., "Highly Active, Binary Catalyst Systems for the Alternating Copolymerization of CO2 and Epoxides under Mild Conditions", Angewandte Chemie International Edition 43:3574-3577 (2004).
Lu et al., "Cobalt catalysts for the coupling of CO 2 and epoxides to provide polycarbonates and cyclic carbonates", Chemical Society Reviews 41:1462-1484 (2012).
Lukaszczyk et al., "Synthesis and Modification of Functional Polycarbonates with Pendant Allyl Groups", Macromolecular Bioscience 1(7):282-289 (2001).
Nakano et al., "Selective Formation of Polycarbonate over Cyclic Carbonate: Copolymerization of Epoxides with Carbon Dioxide Catalyzed by a Colbalt(III) Complex with a Piperidinium End-Capping Arm", Angewandte Chemie International Edition 45:7274-7277 (2006).
Rokicki G., "Aliphatic cyclic carbonates and spiroorthocarbonates as monomers", Progress in Polymer Science 25:259-342 (2000).
Zhang et al., "Synthesis of Atactic and Isotactic Poly(1,2-glycerol carbonate)s: Degradable Polymers for Biomedical and Pharmaceutical Applications", Journal of the American Chemical Society 135:6806-6809 (2013).
Zhang et al., "Synthesis and Characterization of Poly(glyceric Acid Carbonate): A Degradable Analogue of Poly (acrylic Acid)", Journal of the American Chemical Society 137:12660-12666 (2015).

* cited by examiner

Primary Examiner — Jeffrey T. Palenik
(74) Attorney, Agent, or Firm — Nixon Peabody LLP

(57) ABSTRACT

The invention provides polymer compositions, compounds, processes, and methods of use of the polymers for drug delivery, biodegradable consumer plastics, or solvents for Li-based batteries or supercapacitors.

20 Claims, 18 Drawing Sheets

GLYCEROL-BASED POLYCARBONATES

CROSS-REFERENCE TO RELATED APPLICATIONS

This application is a 371 National Phase Entry of International Patent Application No. PCT/US2015/062648 filed on Nov. 25, 2015 which claims benefit under 35 U.S.C. § 119(e) of the U.S. Provisional Application No. 62/084,874, filed Nov. 26, 2014, contents of which are incorporated herein by reference in their entireties.

GOVERNMENT SUPPORT

This invention was made with government support under grant no. DMR 1410450 awarded by the National Science Foundation. The government has certain rights in the invention.

FIELD OF THE INVENTION

Provided herein are polymer compositions, compounds, processes, and methods of use of the polymers for drug delivery, biodegradable consumer plastics, or solvents for Li-based batteries or supercapacitors.

BACKGROUND OF THE INVENTION

Biodegradable plastics are widely used in consumer products from packing materials to grocery bags. A key component of these materials is their ability to degrade as well as the byproducts of the degradation be biocompatible and environmentally friendly. The polymer compositions reported herein degrade to CO2 and glycerol.

Li-ion batteries are widely used for portable devices in the current electric market due to their high gravimetric and volumetric energy densities and cyclability (Xu, K. Non-aqueous Liquid Electrolytes for Lithium-Based Rechargeable Batteries. *Chem. Rev.* 2004, 104, 4303-4417. Quartarone, E.; Mustarelli, P. Electrolytes for solid-state lithium rechargeable batteries: recent advances and perspectives. *Chem. Soc. Rev.* 2011, 40, 2525-2540). Recent developments in Li-ion battery technology have increased their performance and decreased their costs, which have led to their widespread use in everything from cell phones to electric vehicles. However, performance and safety issues still remain a concern. These concerns include capacity loss with cycling and thermal stability when operating above room temperature (Aurbach, D.; Talyosef, Y.; Markovsky, B.; Markevich, E.; Zinigrad, E.; Asraf, L.; Gnanaraj, J. S.; Kim, H.-J. Design of electrolyte solutions for Li and Li-ion batteries: a review. *Electrochimica Acta* 2004, 50, 247. Goodenough, J. B.; Kim, Y. Challenges for Rechargeable Li Batteries. *Chem. Mater.* 2010, 22, 587-603). Overcharging and extreme discharging of Li-ion batteries can lead to overheating and thermal runaway; while improper use of a Li-ion battery can lead to fire or explosion. 8 The volatility and flammability of the organic solvents (EC/DMC) used in typical Li-ion electrolytes are the major source of these thermal stability issues. Consequently, replacement of conventional electrolyte solutions with a non-flammable, non-volatile material to create a Li-ion battery for operation at room temperature and above is highly desirable and would represent both a basic and technological advancement.

Medicine traditionally utilizes pharmacologic agents or surgical interventions for the treatment of disease. Specific targeting or localization of pharmacologic or biologic agents to desired organs and tissues is a complex challenge.

For example, delivery of agents to tumors to treat or cure cancer is limited by non-specific targeting, agent degradation, and high systemic toxicity, to name a few. Treatments of conditions such as cancer remain relatively ineffective as evidenced by high rates of cancer recurrence and low survival; cancer is a leading cause of death for both men and women in the United States (Jemal et al., CA Cancer J. Clin., 60:277-300, 2010). Current methods of cancer treatment include chemotherapy, radiation treatment, and surgical resection.

Other medical applications which utilize drug delivery technologies include immunological applications, pain control, wound healing, infectious disease, transplants, and the development of vaccines. Potential drug candidates often present solubility, toxicity, and/or pharmacokinetic concerns. Thus, there is a broad need for locally and regionally targeted and sustained delivery of therapeutic agents.

Certain polyesters, polycarbonates, and polyamides are biodegradable polymers with low toxicity and degradation properties. Such polymers include poly($\varepsilon$-caprolactone), poly(p-dioxanone), poly(trimethylene carbonate), and most notably poly(glycolic acid) and poly(lactic acid)(see, e.g., Agrawal et al., Biomaterials, 13:176-182, 1992; Attawia et al., J. Biomed. Mater. Res., 29:1233-140, 1995; Heller et al., Adv. Drug Deliv. Rev., 54:1015-1039, 2002; Miller and Williams, Biomaterials, 8:129-137, 1987; and Athanasiou et al., Arthroscopy, 14:726-737, 1998). These polymers are used in a variety of applications including the delivery of therapeutic agents. However, physical properties of the aforementioned polymers are limited by monomer selection, polymerization techniques and post-polymerization modifications. Properties of interest include thermal transition temperatures, bulk strength, flexibility or elasticity, degradation, crystallinity, and hydrophobicity. When polymers are utilized for in vivo applications, the physical properties of the material affect host response. Hence, a need exists for polymers and delivery systems with desired characteristics that are effective for treatment of diseases and conditions in vivo and that can be tailored for specific therapeutic needs and tissue characteristics.

Linear poly(1,3 glycerol carbonate)s are known and synthesized via ring-opening polymerization of the six-membered 3-benzyloxytrimethylene carbonate (Ray, W. C.; Grinstaff, M. W. Macromolecules 2003, 36, 3557-3562, He, F.; Wang, Y.; Feng, J.; Zhuo, R.; Wang, X. Polymer 2003, 44, 3215-3219. (27) Helou, M.; Miserque, O.; Brusson, J. M.; Carpentier, J. F.; Guillaume, S. M. Chemistry—A European Journal 2010, 16, 13805-13813) or dimethylacetal dihydroxyacetone carbonate (Zelikin, A. N.; Zawaneh, P. N.; Putnam, D. *Biomacromolecules* 2006, 7, 3239-3244. Zhang, X.; Mei, H.; Hu, C.; Zhong, Z.; Zhuo, R. *Macromolecules* 2009, 42, 1010-1016. Simon, J.; Olsson, J. V.; Kim, H.; Tenney, I. F.; Waymouth, R. M. *Macromolecules* 2012, 45, 9275-9281) monomers. Post polymerization, the benzyl group can be hydrogenated or the ketone can be reduced to afford a hydroxyl group, respectively. Although these routes provide ample materials, the monomers require 2-3 steps for preparation and the resulting polymers possess a secondary, less reactive hydroxyl for subsequent use and are usually of broad molecular distribution. Surprisingly, to the best of our knowledge, linear poly(1,2-glycerol carbonate)s are far less explored. These materials would likely be challenging to synthesize via the ring opening of the corresponding five-membered cyclic glycerol carbonate monomer, as five-membered cyclic carbonate monomers are thermodynamic stable and, generally, incapable of ring-opening polymerization (Rokicki, A. *Prog. Polym. Sci.* 2000, 25, 259-342). However these polymers may be accessed via the ring-opening copolymerization of the corresponding glycidyl ether with $CO_2$. This polymerization route has been explored to prepare other polycarbonate polymers Coates, G. W.; Moore, D. R. *Angew Chem Int Edit* 2004, 43, 6618-6639. Darensbourg, D. J. *Chem Rev* 2007, 107, 2388-2410. Sakakura, T.; Choi, J. C.; Yasuda, H. *Chem Rev* 2007, 107, 2365-2387).

Poly(acrylic acid) have found extensive applications including water/sewage treatment, superabsorbent polymers, detergent, adhesives, dispersant, cosmetics, as well as drug delivery and really serve as the workhorse of chemical industry.

Despite its widespread use for both practical applications and fundamental studies, poly(acrylic acid) suffers from poor degradability which is rendered by the all-carbon backbone. It is well established that only oligomers of poly(acrylic acid)s with molecular weights (MWs) less than 600 g/mol (degree of polymerization <8) are biodegradable and yet, the molecular weights of most industrially relevant poly(acrylic acid)s are well above this value. For example, low molecular weight poly(acrylic acid)s used for detergent applications have an average MW of 4000-5000 g/mol. Furthermore, unlike structural materials (e.g. plastics) that can be easily collected and assorted for recycling or waste treatment such as land filling, composting and incineration, water soluble polymers, e.g. poly(acrylic acid)s, are difficult to recover. With all these factors coupled together, poly(acrylic acid)s constitute a major concern in industry as well as pharmaceutical and biomedical fields where biodegradability and biocompatibility are highly desired.

SUMMARY OF THE INVENTION

The invention is based, at least in part, on the discovery that poly(glyceric acid carbonate)s and alkyl functionalized poly(1,2 glycerol carbonates) and poly(glyceric acid carbonate)s and pharmaceutical agent/composition functionalized poly(1,2 glycerol carbonates) and poly(glyceric acid carbonate)s represent a new type of glycerol based polymer that 1) degrade into glycerol and carbon dioxide; 2) the poly(1,2 glycerol carbonates) degrade more readily than conventional poly(1,3 glycerol carbonates; and 3) poly(1,2 glycerol carbonates) can be processed to give melts, viscous fluids, liquids, films, sheets, gels, meshes, foams, fibers, or particles. These form factors can be used for the controlled, localized, sustained delivery of various agents for treatment of diseases and conditions. A further embodiment of this invention is the use of unloaded, empty form factors that localize to a specific site after administration to a subject where they remain and then concentrate an agent that is subsequently delivered to the subject. A further embodiment of this invention is the use of a pharmaceutical agent/composition functionalized polymer with a pharmaceutical agent/composition entrapped within the polymer to yield two distinct pharmaceutical composition (i.e., drug or agent) delivery release rates. Provided herein are compounds and processes to prepare polymer melts, viscous fluids, liquids, films, sheets, gels, meshes, foams, fibers, or particles and related compositions, as well as processes for delivery of agents. These polymers are of interest as components for medical and medical device applications, as electrolyte materials for batteries, and as degradable and environmentally friendly polymers/plastics for the consumer and electronics industries.

Also provided herein are compositions comprising a polymer described herein and a first pharmaceutical agent and a second pharmaceutical agent. In some embodiments, at least one of the first and the second pharmaceutical agent is covalently linked with the polymer described herein. In some embodiments, one of the first and the second pharmaceutical agent is covalently linked with the polymer and the other of the pharmaceutical agents is not covalently linked with the polymer. Without limitations the first and the second pharmaceutical agent can be the same or different. In some embodiments, the first and the second pharmaceutical agent are the same. In some other embodiments, the first and the second pharmaceutical agent are different. In some embodiments, the pharmaceutical agent that is not covalently linked with the polymer is encapsulated in an article, such as a polymeric film, sheet, mesh, foam, fiber, or particle, comprising the the pharmaceutical agent linked polymer. The pharmaceutical agent can be linked with the polymer via a linker. In some embodiments, the linker is a succinic acid moiety.

The delivery site of interest can include the following: specific cell types, a tissue, an organ, a wound, a lymph node, an established tumor, the remains of a tumor from a surgically resected tumor, etc. It can also be sites of inflammation or specific organs or biologic locations or sites of pathologic processes such as inflammation, such as in joints, where increased local drug concentrations are desired. Such a drug delivery system reduces systemic exposure of an agent and increases the local concentration of an agent at the tissue site.

The invention is based, at least in part, on the discovery that poly(glyceric acid carbonates) represent a new type of polycarbonates that 1) degrade into glyceric acid and carbon dioxide; 2) the poly(glyceric acid carbonates) degrade more readily than conventional acid polymer—poly(acrylic acid); and 3) poly(glyceric acid carbonates) can be processed to give melts, viscous fluids, liquids, films, sheets, gels, meshes, foams, fibers, or particles. These form factors can be used for the controlled, localized, sustained delivery of various agents for treatment of diseases and conditions. A further embodiment of this invention is the use of unloaded, empty form factors that localize to a specific site after administration to a subject where they remain and then concentrate an agent that is subsequently delivered to the subject. Provided herein are compounds and processes to prepare polymer melts, viscous fluids, liquids, films, sheets, gels, meshes, foams, fibers, or particles and related compositions, and processes for delivery of agents.

Likewise, alkyl (ether and ester) derivatives of poly(1,2 glycerol carbonates) can be synthesized and processed to give melts, viscous fluids, liquids, films, sheets, gels, meshes, foams, fibers, or particles and related compositions. These by polymers can degrade into glycerol acid, carbon dioxide, and the corresponding alcohol or ester.

Likewise, alkyl (ether and ester) derivatives of poly(1,2 glycerol carbonates) can be synthesized and processed to give melts, viscous fluids, liquids by preparing: 1) a polymer composition possessing a broad PDI (>2) and/or low molecular weight (<1000 g/mol); 2) a mixtures of poly(1,2 glycerol carbonates) with different functionalities. The discovery is that to prepare a non-flammable, biocompatible, non-volatile Li battery solvent based on polycarbonates, a low MW and broad PDI will prevent or inhibit polymer crystallization as well as the formation of materials with high melting temperatures. Such polymeric materials can then be mixed with Li salts to create the electrolyte solvent.

One of the polymers reported herein is a degradable version of poly(acrylic acid) by linking 1,2-position of polyacrylic acid with a carbonate linkage. This poly(glyceric acid carbonate) will be biodegradable to afford natural metabolites glyceric acid—a downstream metabolite of glycerol and $CO_2$, which are known to be non-toxic and biocompatible.

This polymer or polymer composition will potentially serve as a replacement for current acid polymer, mainly poly(acrylic acid)s, with additional and critical benefits that it is readily degradable and the degradation product is nontoxic and biocompatible. This polymer or polymer composition will potentially be used in water/sewage treatment, superabsorbent polymers, detergent, adhesives, dispersant, cosmetics, as well as drug delivery.

DETAILED DESCRIPTION OF THE INVENTION

Definitions

Figure 1:
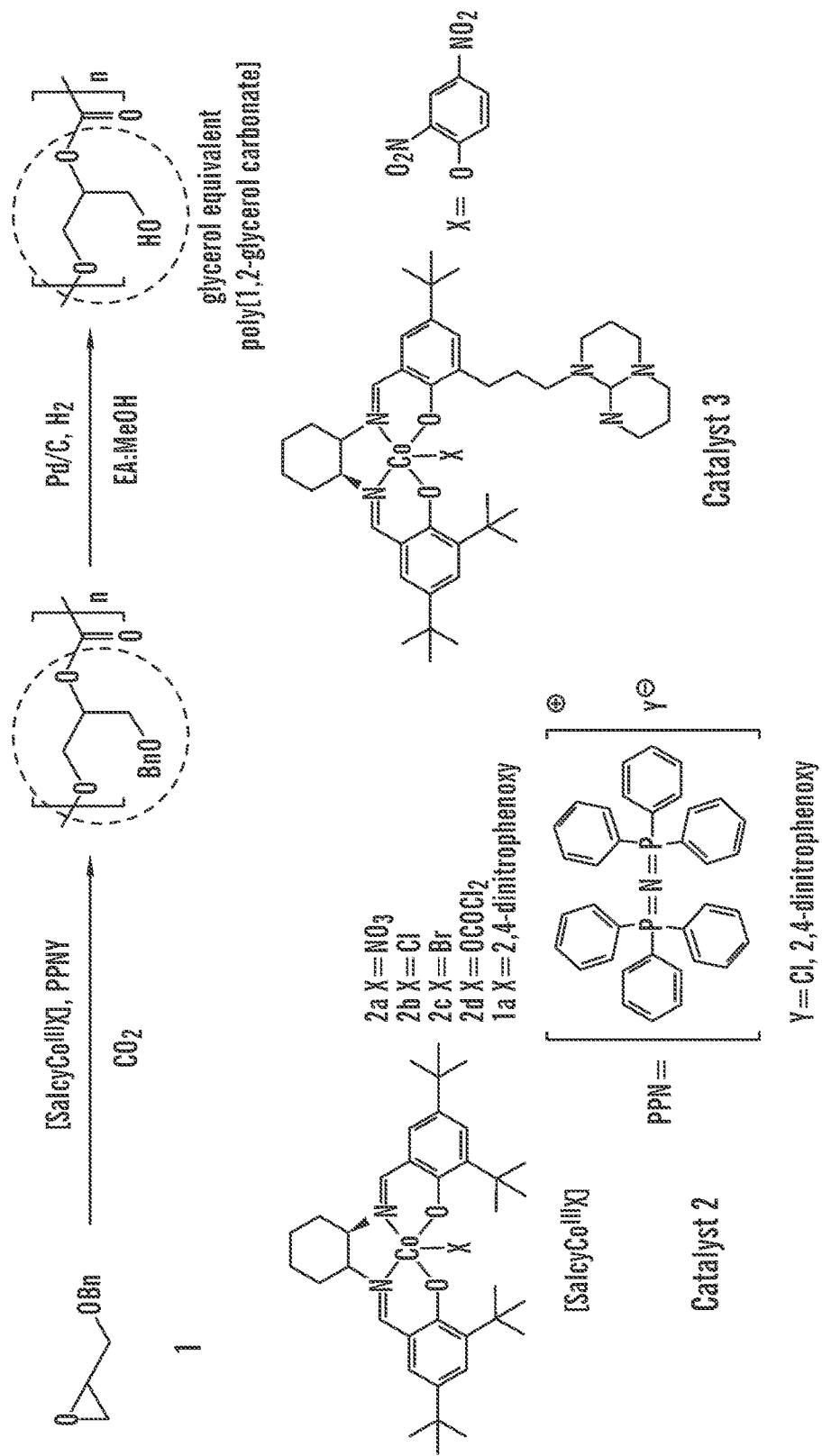
FIG. 1 is a synthesis scheme of synthesis of of atactic poly(benzyl 1,2-glycerol carbonate)s (PBGC's) using [(S, S)-SalcyCo$^{III}$X]/PPNY.

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein, the term "bioactive agent" refers to an agent that is capable of exerting a biological effect in vitro and/or in vivo. The biological effect can be therapeutic in nature. As used herein, "bioactive agent" refers also to a substance that is used in connection with an application that is diagnostic in nature, such as in methods for diagnosing the presence or absence of a disease in a patient. The bioactive agents can be neutral or positively or negatively charged. Examples of suitable bioactive agents include pharmaceuticals and drugs, cells, gases and gaseous precursors (e.g., O2), synthetic organic molecules, proteins, enzymes, growth factors, vitamins, steroids, polyanions, nucleosides, nucleotides, polynucleotides, and diagnostic agents, such as contrast agents for use in connection with magnetic resonance imaging, ultrasound, positron emission transmography, computed tomography, or other imaging modality of a patient.

As used herein, the term "biocompatible" refers to the absence of an adverse acute, chronic, or escalating biological response to an implant or coating, and is distinguished from a mild, transient inflammation which typically accompanies surgery or implantation of foreign objects into a living organism.

As used herein, the term "biodegradable" refers to the erosion or degradation of a material into smaller entities which will be metabolized or excreted under the conditions normally present in a living tissue. Biodegradation is preferably predictable both in terms of the degradation products formed, including metabolic byproducts formed, and in terms of duration, whereas the duration of biodegradation can be dependant upon the chemical structure of the material.

As used herein, the terms "controlled release," "sustained release," and "prolonged release" refer to the continuous release of drugs from a material for at least 24 hours wherein the release can be substantially constant or vary as a function of time. In some embodiments, the continuous release is greater than 30 days. In some embodiments, the release kinetics are linear and repeatable.

As used herein, the terms "compliance" or "compliant" are used in a general sense and refer, for example, to the ability of an implant to closely match the mechanical properties of tissues at the implant site, such as in the sense of bending or flexing with the natural movement of tissues at the implant site, except when "compliance" is used in the specific technical sense as the reciprocal of modulus.

As used herein, the term "co-polymer" refers to a polymer comprised of at least two different monomer constituents. A copolymer can comprise a co-polymer in which a base (main) monomer (which forms a biodegradable polymer) is polymerized with a doping agent as described herein. In some embodiments, a block co-polymer including doping agent in this manner is prepared and then mixed with the biodegradable polymer (i.e., the first monomer polymerized without the doping agent) and bioactive agent in the manufacture of a 3-dimensional composition as described herein. The co-polymer can possess a block or random structure.

As used herein, the term "pharmaceutical composition" refers to a chemical compound or composition capable of inducing a desired therapeutic effect in a subject. In certain embodiments, a pharmaceutical composition contains an active agent, which is the agent that induces the desired therapeutic effect. The pharmaceutical composition can contain a prodrug of the compounds provided herein. In certain embodiments, a pharmaceutical composition contains inactive ingredients, such as, for example, carriers and excipients.

As used herein, the term "pharmaceutically acceptable" refers to a formulation of a compound that does not significantly abrogate the biological activity, a pharmacological activity and/or other properties of the compound when the formulated compound is administered to a subject. In certain embodiments, a pharmaceutically acceptable formulation does not cause significant irritation to a subject.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates, PEGylation, or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzylphenethylamine, 1-para-chloro-benzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula $C=C(OR)$ where R is hydrogen, alkyl, alkenyl, alkynyl, aryl, heteroaryl, aralkyl, heteroaralkyl, cycloalkyl, or heterocyclyl. Pharmaceutically acceptable enol esters include, but are not limited to, derivatives of formula $C=C(OC(O)R)$ where R is hydrogen, alkyl, alkenyl, alkynyl, aryl, heteroaryl, aralkyl, heteroaralkyl, cycloalkyl, or heterocyclyl. Pharmaceutically acceptable solvates and hydrates are complexes of a compound with one or more solvent or water molecules, or 1 to about 100, or 1 to about 10, or one to about 2, 3, or 4, solvent or water molecules.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

The phrase "therapeutically effective amount" refers to the amount of a pharmaceutical composition that elicits the biological or medicinal response in a tissue, system, animal, individual, patient, or human that is being sought by a researcher, veterinarian, medical doctor or other clinician. Generally, the term "therapeutically effective amount" refers to an amount of a pharmaceutical composition sufficient to achieve a therapeutic effect. Therapeutic effect can be, e.g., reduction in the amount of a disease marker or partial normalization of other laboratory test, such as a urine analysis or blood chemistry for any particular disease or disorder, reduction in swelling, or subjective reduction in pain experienced by the subject.

As used herein, "tunable drug release" refers to the ability to reduce either the cumulative amount of released drug over a fixed time period by at least 20 percent, or the ability to alter the rate of drug release over a fixed time period by at least 20 percent, or both.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

Meshes, which include a preferred embodiment of the present invention, include commercially available products. Examples of films and meshes include INTERCEED (Johnson & Johnson, Inc.), PRECLUDE (W. L. Gore), and POLYACTIVE (poly(ether ester) multiblock copolymers (Osteotech, Inc., Shrewsbury, N.J.), based on poly(ethylene glycol) and poly(butylene terephthalate), and SURGICAL absorbable hemostat gauze-like sheet from Johnson & Johnson. Another mesh is a prosthetic polypropylene mesh with a bioresorbable coating called SEPRAMESH Biosurgical Composite (Genzyme Corporation, Cambridge, Mass.). One side of the mesh is coated with a bioresorbable layer of sodium hyaluronate and carboxymethylcellulose, providing a temporary physical barrier that separates the underlying tissue and organ surfaces from the mesh. The other side of the mesh is uncoated, allowing for complete tissue ingrowth similar to bare polypropylene mesh. In one embodiment, the fibrosis-inducing agent may be applied only to the uncoated side of SEPRAMESH and not to the sodium hyaluronate/carboxymethylcellulose coated side. Other films and meshes include: (a) BARD MARLEX mesh (C.R. Bard, Inc.), which is a very dense knitted fabric structure with low porosity; (b) monofilament polypropylene mesh such as PROLENE available from Ethicon, Inc. Somerville, N.J. (see, e.g., U.S. Pat. Nos. 5,634,931 and 5,824,082)); (c) SURGISIS GOLD and SURGISIS IHM soft tissue graft (both from Cook Surgical, Inc.) which are devices specifically configured for use to reinforce soft tissue in repair of inguinal hernias in open and laparoscopic procedures; (d) thin walled polypropylene surgical meshes such as are available from Atrium Medical Corporation (Hudson, N.H.) under the trade names PROLITE, PROLITE ULTRA, and LITEMESH; (e) COMPOSIX hernia mesh (C.R. Bard, Murray Hill, N.J.), which incorporates a mesh patch (the patch includes two layers of an inert synthetic mesh, generally made of polypropylene, and is described in U.S. Pat. No. 6,280,453) that includes a filament to stiffen and maintain the device in a flat configuration; (f) VISILEX mesh (from C.R. Bard, Inc.), which is a polypropylene mesh that is constructed with monofilament polypropylene; (g) other meshes available from C.R. Bard, Inc. which include PERFIX Plug, KUGEL Hernia Patch, 3D MAX mesh, LHI mesh, DULEX mesh, and the VENTRALEX Hernia Patch; and (h) other types of polypropylene monofilament hernia mesh and plug products include HERTRA mesh 1, 2, and 2A, HERMESH 3, 4 & 5 and HERNIAMESH plugs T1, T2, and T3 from Herniamesh USA, Inc. (Great Neck, N.Y.).

Where reference is made to a URL or other such identifier or address, it understood that such identifiers can change and particular information on the internet can come and go, but equivalent information can be found by searching the internet. Reference thereto evidences the availability and public dissemination of such information.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with a value can mean 5%, 4.5%, 4%, 3.5%, 3%, 2.5%, 2%, 1.5%, mean 1% or 0.5% of the value being referred to.

Unless specific definitions are provided, e.g., as indicated below, the nomenclature used in connection with, and the laboratory procedures and techniques of, analytical chemistry, biochemistry, synthetic organic chemistry, and medicinal and pharmaceutical chemistry described herein are those known in the art. In the event that there is a plurality of definitions for terms herein, those in this section prevail.

As used herein, the abbreviations for any protective groups, amino acids, and other compounds are, unless indicated otherwise, in accord with their common usage, recognized abbreviations, or the IUPAC-IUB Commission on Biochemical Nomenclature, Biochem., 11:942-944 (1972).

As used herein, use of the singular includes the plural unless specifically stated otherwise. As used herein, "or" means "and/or" unless stated otherwise. Furthermore, use of the term "including" as well as other forms, such as "includes," and "included," is not limiting.

As used herein, the terms "treating" or "treatment" encompass responsive measures, e.g., designed to inhibit, slow or delay the onset of a symptom of a disease or disorder, achieve reduction of a symptom or disease state, and/or to alleviate, ameliorate, or lessen a disease or disorder and/or its symptoms. As used herein, the terms "treating" or "treatment" encompass either or both responsive and prophylaxis measures, e.g., designed to inhibit, slow, or delay the onset of a symptom of a disease or disorder, achieve a full or partial reduction of a symptom or disease state, and/or to alleviate, ameliorate, lessen, or cure a disease or disorder and/or its symptoms.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, the term "carrier" refers to a compound that facilitates the administration and delivery of another compound and may also facilitate the administration and delivery of another compound and may also facilitate the incorporation of another compound into cells or tissues. For example, dimethyl sulfoxide (DMSO) is a commonly used carrier for improving incorporation of certain organic compounds into cells or tissues.

As used herein, the term "pharmaceutical composition" refers to a chemical compound or composition capable of inducing, alone or in combination with another agent, a desired therapeutic effect or outcome in a subject and includes agents or compounds that can increase bioavailability of other agents. In certain embodiments, a pharmaceutical composition contains an active agent, which is the agent that induces the desired therapeutic effect. The pharmaceutical composition can contain a prodrug of the compounds provided herein. In certain embodiments, a pharmaceutical composition contains inactive ingredients, such as, for example, carriers and excipients.

As used herein, the term "pharmaceutically acceptable" refers to a formulation of a compound that does not significantly abrogate the biological activity, pharmacological activity and/or other properties of the compound when the formulated compound is administered to a subject. In certain embodiments, a pharmaceutically acceptable formulation does not cause significant irritation to a subject.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates, PEGylation, or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzylphenethylamine, 1-para-chloro-benzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

"Alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. There can be optionally inserted along the alkyl chain one or more oxygen, silicon, sulfur, or substituted or unsubstituted nitrogen atoms, wherein the nitrogen substituent is lower alkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

"Alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

"Cycloalkyl" refers to a non-aromatic mono- or multicyclic ring system of about 4 to about 10 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

"Aryl" refers to an aromatic carbocyclic radical containing about 6 to about 10 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Aroyl" means an aryl-CO— group, wherein aryl is as previously described. Exemplary aroyl groups include benzoyl and 1- and 2-naphthoyl.

"Alkoxy" refers to an alkyl-O— group, wherein alkyl is as previously described. Exemplary alkoxy groups include methoxy, ethoxy, n-propoxy, i-propoxy, n-butoxy, and heptoxy.

"Aryloxy" refers to an aryl-O— group, wherein the aryl group is as previously described. Exemplary aryloxy groups include phenoxy and naphthoxy.

"Alkylthio" refers to an alkyl-S— group, wherein alkyl is as previously described. Exemplary alkylthio groups include methylthio, ethylthio, i-propylthio and heptylthio.

"Arylthio" refers to an aryl-S— group, wherein the aryl group is as previously described. Exemplary arylthio groups include phenylthio and naphthylthio.

"Aralkyl" refers to an aryl-alkyl-group, wherein aryl and alkyl are as previously described. Exemplary aralkyl groups include benzyl, phenylethyl and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Dialkylamino" refers to an —NRR' group, wherein each of R and R' is independently an alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H2N—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described. "Acylamino" refers to an acyl-NH— group, wherein acyl is as previously described. "Aroylamino" refers to an aroyl-NH— group, wherein aroyl is as previously described.

"Alkylene" refers to a straight or branched bivalent aliphatic hydrocarbon group having from 1 to about 30 carbon atoms. The alkylene group can be straight, branched, or cyclic. The alkylene group can be also optionally unsaturated and/or substituted with one or more "alkyl group substituents." There can be optionally inserted along the alkylene group one or more oxygen, sulphur, or substituted or unsubstituted nitrogen atoms, wherein the nitrogen substituent is alkyl as previously described. Exemplary alkylene groups include methylene (—CH— ethylene (—CH$_2$—CH$_2$—), propylene (—(CH$_2$)$_3$—), cyclohexylene (—C$_6$H$_{10}$—), —CH=CH—CH=CH—, —CH=CH—CH$_2$—, —(CF$_2$)$_n$(CH$_2$)$_m$—, wherein n is an integer from about 1 to about 50 and m is an integer from 0 to about 50, —(CH$_2$)$_n$—N(R)—(CH$_2$)$_m$—, wherein each of m and n is independently an integer from 0 to about 50 and R is hydrogen or alkyl, methylenedioxy (—O—CH$_2$—O—) and ethylenedioxy (—O—(CH$_2$)$_2$—O—). An alkylene group can have about 2 to about 3 carbon atoms and can further have 6-50 carbons.

"Halo" or "halide" refers to fluoride, chloride, bromide, or iodide.

As used herein, the term "linker" means an organic moiety that connects two parts of a compound. Linkers typically comprise a direct bond or an atom such as oxygen or sulfur, a unit such as NR$^1$, C(O), C(O)NH, C(O)O, NHC(O)O, OC(O)O, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, NR$^1$, C(O), C(O)NH, C(O)O, NHC(O)O, OC(O)O, SO$_2$NH, cleavable linking group, substituted or unsubstituted aryl, substituted or unsubstituted heteroaryl, substituted or unsubstituted heterocyclic; where R$^1$ is hydrogen, acyl, aliphatic or substituted aliphatic.

The term "agent" includes without limitation, medicaments, vitamins, mineral supplements, hormones, growth factors, substances used for the treatment, prevention, diagnosis, cure or mitigation of disease or illness, substances that affect the structure or function of the body, or pro-drugs, which become biologically active or more active after they have been placed in a predetermined physiological environment.

A "bioactive agent" refers to an agent that is capable of exerting a biological effect in vitro and/or in vivo. The biological effect can be therapeutic in nature. As used herein, "bioactive agent" refers also to a substance that is used in connection with an application that is diagnostic in nature, such as in methods for diagnosing the presence or absence of a disease in a patient. The bioactive agents can be neutral or positively or negatively charged. Examples of suitable bioactive agents include pharmaceuticals and drugs, cells, gases and gaseous precursors (e.g., O$_2$), synthetic organic molecules, proteins, enzymes, growth factors, vitamins, steroids, polyanions, nucleosides, nucleotides, polynucleotides and diagnostic agents, such as contrast agents for use in connection with magnetic resonance imaging, ultrasound, positron emission tomography (PET), X-ray computed tomography or other imaging modalities.

"Genetic material" refers generally to nucleotides and polynucleotides, including deoxyribonucleic acid (DNA), ribonucleic acid (RNA), and peptide nucleic acid (PNA). The genetic material can be made by synthetic chemical methodology known to one of ordinary skill in the art, or by the use of recombinant technology, or by a combination of the two. The DNA and RNA can optionally comprise unnatural nucleotides and can be single or double stranded. "Genetic material" refers also to sense and anti-sense DNA and RNA, that is, a nucleotide sequence that is complementary to a specific sequence of nucleotides in DNA and/or RNA.

The polymers provided herein can be utilized to diagnose disease, promote healing or prevent disease by targeting or concentrating a drug to local and regional areas. The polymers provided herein can also be used for a variety of applications including, but not limited to, production of micro- and nanoparticles. Such materials can be used to repair an injured tissue, organ, bone, or genetic defect. Other uses of the polymers provided herein include treatment of early, late or previously treated malignancies, pre-treatment of malignancies or other condition as a sensitizer to augment therapy of another agent such as with radiation sensitizers, avoidance of locoregional lymph node metastasis, augmentation of local wound healing and decrease in infection, manipulation of structure and abnormal scar formation, delivery of drugs, cytokines or steroids—into, for example, joint capsules—insulin, glucagon, or genetically missing enzymes and for the treatment of post-operative pain. In one embodiment, the polymers provided herein are used to treat cancer. For example, the polymers provided herein can be used to treat various malignancies, e.g., lung, colon, prostate, pancreas, ovarian, sarcoma, mesothelioma, or breast cancer at all stages.

The polymers provided herein can be used to deliver any agent by concentrating it at a specific site. The agent can be in any pharmaceutically acceptable form of an agent, including pharmaceutically acceptable salts. A large number of pharmaceutical agents are known in the art and are amenable for use in the pharmaceutical compositions of the polymeric materials described herein. Acceptable agents include, but are not limited to, chemotherapeutic agents, such as radio-sensitizers; receptor inhibitors and agonists or other anti-neoplastic agents; immune modulators, anti-inflammatory agents, and bioactive agents, such as cytokines, growth factors, or steroids with or without the co-incorporation of tumor or pathogen antigens to increase the anti-neoplastic response as a means of vaccine development; local anesthetic agents; antibiotics; or nucleic acids as a means of local gene therapy.

Unless otherwise defined, e.g., as above, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety, unless noted otherwise. In case of conflict, the present specification, including definitions, will control. In addition, the materials, methods, and examples are illustrative only and not intended to be limiting.

Standard techniques can be used for chemical syntheses, chemical analyses, pharmaceutical preparation, formulation and delivery, and treatment of subjects. Reactions and purification techniques can be performed, e.g., using kits according to manufacturer's specifications or as commonly accomplished in the art or as described herein. The foregoing techniques and procedures generally are performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989).

Other features and advantages of the invention will be apparent from the following detailed description, examples and claims.

Polymers

Without limitations, the dendritic oligomer or polymer disclosed herein can be a linear, comb, branched, or dendritic oligomer or polymer. Generally, the oligomer or the polymer comprises at least one of the following formulas:

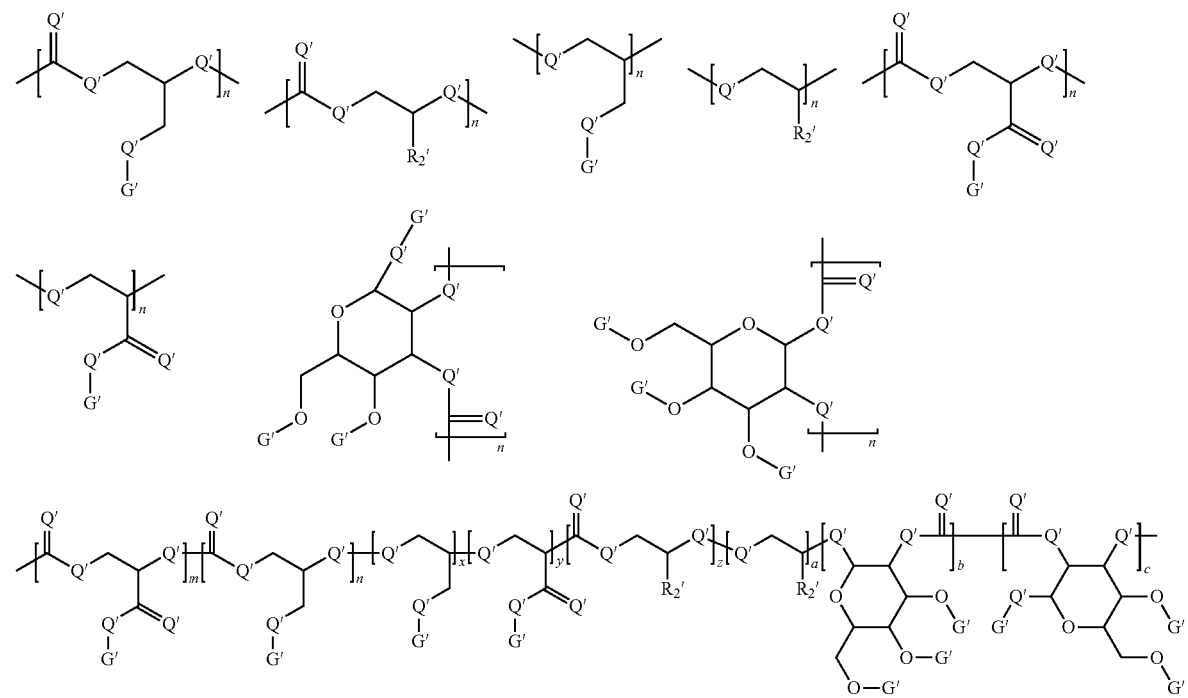

In the polymers disclosed herein, the polymeric terminal groups can be selected independently from among amines, thiols, amides, phosphates, sulphates, hydroxides, metals, alkanes, alkenes and alkynes.

In the polymers disclosed herein, each Q' is independently selected from among O, S, Se, or NH. In some embodiments, Q' is O.

In the polymers disclosed herein, each G' can be independently selected from among

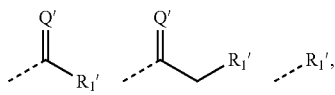

wherein G'1 and G'2 are not the same. In some embodiments, G' is

Without limitations, $R'_1$ can be selected from among hydrogen, a straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R'_1$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or $R'_1$ is selected from among a photocrosslinkable or ionically crosslinkable group.

In some embodiments, $R'_1$ is not hydrogen or phenyl or benzyl.

$R'_2$ can be selected from among hydrogen, a straight or branched alkyl, cycloalkyl, aryl, olefin, silyl, alkylsilyl, arylsilyl, alkylaryl, fluorocarbon, or arylalkyl chain of 1-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

In some embodiments, WI can be selected from among hydrogen or a straight or branched alkyl, cycloalkyl, aryl, olefin, silyl, alkylsilyl, arylsilyl, alkylaryl or arylalkyl chain of 2-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

In some preferred embodiments, $R'_1$ can be selected from among hydrogen or a straight or branched alkyl, cycloalkyl, aryl, olefin, silyl, alkylsilyl, arylsilyl, alkylaryl or arylalkyl chain of 3-50 carbons. In some still more preferred embodiments, $R'_1$ is selected from among hydrogen or a straight or branched alkyl, alkylaryl or arylalkyl chain of 3-50 carbons. In some embodiments, $R'_1$ is hydrogen, $C_1$-$C_6$ alkyl, aryl, or a $C_1$-$C_6$ alkyl substituted with an aryl or heteroaryl. In some embodiments, $R'_1$ is hydrogen, methyl, ethyl, propyl, butyl or benzyl.

In some embodiments, Q' is O and $R'_1$ is selected from among hydrogen or a straight or branched alkyl, cycloalkyl, aryl, olefin, silyl, alkylsilyl, arylsilyl, alkylaryl or arylalkyl chain of 2-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents. In some embodiments, Q' is O and $R'_1$ is selected from among hydrogen or a straight or branched alkyl, cycloalkyl, aryl, olefin, silyl, alkylsilyl, arylsilyl, alkylaryl or arylalkyl chain of 3-50 carbons. In some embodiments, Q' is O and $R'_1$ is selected from among hydrogen or a straight or branched alkyl, alkylaryl or arylalkyl chain of 3-50 carbons. In some embodiments, Q' is O and is selected from among hydrogen or a straight or branched alkyl chain of 3-50 carbons.

In some embodiments, the polymer disclosed herein is of formula

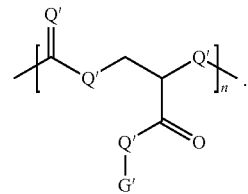

In some further embodiments of this G' is

In some embodiments, the polymer disclosed herein is of formula

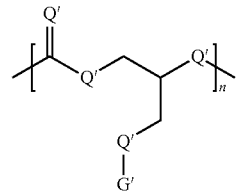

and G' is G' is

In some embodiments, the polymer disclosed herein is of formula

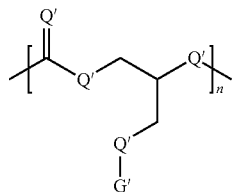

and $R_1'$ is $R_1'$ can be selected from among a straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R_1'$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, a pharmaceutical composition or any epitope for a biological receptor; or $R_1'$ is selected from among a photo-crosslinkable or ionically crosslinkable group.

In some embodiments, the polymer disclosed herein is of formula and

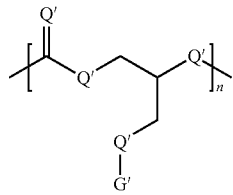

$R_1'$ is not hydrogen.

In some embodiments, the polymer disclosed herein is of formula

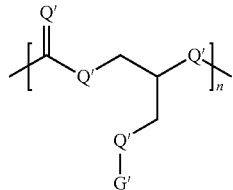

and $R_1'$ is not phenyl.

In some embodiments, the polymer disclosed herein is of formula

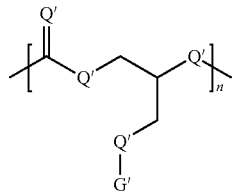

and $R_1'$ is not benzyl.

In some embodiments, the polymer disclosed herein is of formula

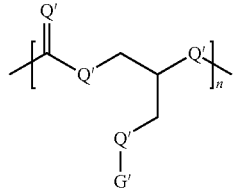

and $R_1'$ is a straight or branched alkyl, cycloalkyl, aryl, olefin, silyl, alkylsilyl, arylsilyl, alkylaryl or arylalkyl chain of 1-50 carbons. In some embodiments, the polymer is of formula

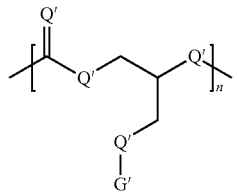

and $R_1'$ is a $C_1$-$C_{10}$ alkyl group. In one embodiment, the polymer is of formula

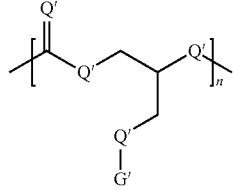

and $R_1'$ is methyl, ethyl, propyl, butyl, pentyl, or hexyl.

As is well known in the art, polymers can be created having various different chain lengths and architectures. Additionally, physical and chemical properties of a given polymer can be a function of chain length. The polymer dispersion Index (PDI) is a metric that details the distribution of polymer chain lengths within a sample polymer. For certain applications, a relatively short chain length may be desired, while other applications call for polymer properties associated with polymers having relatively long chain lengths. Generally, the PDI can range from about 0.25 to about 5. In some embodiments, the PDI is less than about 1.75, less than about 1.5, less than about 1.25, less than about 1, less than about 0.9, less than about 0.8, less than about 0.75, less than about 0.7, less than about 0.6, less than about 0.5, less than about 0.4, or less than about 0.3. In some embodiments, PDI is about 2, about 2.25, about 2.5, about 2.75, about 3 or higher. In some embodiments, PDI is in the range from about 1.05 to about 1.35 or from about 1.1 to about 1.3.

The polymers can have a molecular weight (MW) of from about 0.5 kDa to about 1,000 kDa. In some embodiments, polymers can have a molecular weight of about 10 kDa to about 500 kDa. Without limitations, the molecular weight can be the peak average molecular weight (Mp), the number average molecular weight (Mn), or the weight average molecular weight (Mw). In some embodiments, the polymer has a MW of less than 1000.

Generally, more than 50%, more than 55%, more than 60%, more than 65%, more than 70%, more than 75%, more than 80%, more than 85%, more than 90% or more than 95% of adjacent stereocenters in the polymer have the same relative stereochemistry. In some embodiments, greater than 50%, greater than 55%, greater than 60%, greater than 65%, greater than 70%, greater than 75%, greater than 80%, greater than 85%, greater than 90% or greater than 95%, of the stereocenters are of the same stereochemistry. In some other embodiments, the polymer has a random stereochemistry.

Without limitations, the polymer disclosed herein can be formed into films, sheets, meshes, mats, non-woven mats, foams, fibers, gels, cross-linked gels, and/or particles. The polymer disclosed herein can also be included in melts, waxes, and/or viscous liquids. Further, the polymer can also be mixed with or added to an electrolyte solvent. Moreover, the polymer can be combined with a second polymer, e.g., a polymer not disclosed herein, to form copolymers or mixtures.

Agents that can be Incorporated into Polymeric Materials

Any agent is a candidate to be incorporated within the polymer particles or delivered subsequently to the particle at the tissue site as described herein. The pharmaceutical composition or agent can be functionalized (covalently bound) to polymer and/or it can be entrapped or encapsulated within the polymer. For example, a polymer particle described herein can incorporate a pharmaceutical agent comprises (1) nonsteroidal anti-inflammatory drugs (NSAIDs) analgesics, including but no limited to diclofenac, ibuprofen, ketoprofen, and naproxen; (2) opiate agonist analgesics, including but no limited to codeine, vancomycin, ceftazidime, fentanyl, hydromorphone, and morphine; (3) salicylate analgesics, including but no limited to aspirin (ASA) (or enteric coated ASA); (4) H1-blocker antihistamines, including but no limited toclemastine and terfenadine; (5) H2-blocker antihistamines, including but no limited tocimetidine, famotidine, nizadine, and ranitidine; (6) anti-infective agents, including but no limited tomupirocin; (7) antianaerobic anti-infectives, including but no limited tochloramphenicol metronidazole and clindamycin; (8) antifungal antibiotic anti-infectives, including but no limited toamphotericin b, clotrimazole, fluconazole, and ketoconazole; (9) macrolide antibiotic anti-infectives, including but no limited toazithromycin and erythromycin; (10) miscellaneous beta-lactam antibiotic anti-infectives, including but no limited toaztreonam and imipenem; (11) penicillin antibiotic anti-infectives, including but not limited to nafcillin, oxacillin, penicillin G, and penicillin V; (12) quinolone antibiotic anti-infectives, including but not limited to ciprofloxacin and norfloxacin; (13) tetracycline antibiotic anti-infectives, including but not limited to doxycycline, minocycline, and tetracycline; (14) antituberculosis antimycobacterial anti-infectives including but not limited to isoniazid (INH), and rifampin; (15) antiprotozoal anti-infectives, including but not limited to atovaquone and dapsone; (16) antimalarial antiprotozoal anti-infectives, including but not limited to chloroquine and pyrimethamine; (17) antiretroviral anti-infectives, including but not limited to ritonavir and zidovudine; (18) antiviral anti-infective agents, including but not limited to acyclovir, ganciclovir, interferon alpha, and rimantadine; (19) alkylating antineoplastic agents, including but not limited to carboplatin and cisplatin; (20) nitrosourea alkylating antineoplastic agents, including but not limited to carmustine (BCNU); (21) antimetabolite antineoplastic agents, including but not limited to methotrexate; (22) pyrimidine analog antimetabolite antineoplastic agents, including but not limited to fluorouracil (5-FU), gemcitabine, or ceftazidine, aminoglycodi meroperium, or ticarcillin and tobramycin; (23) hormonal antineoplastics, including but not limited to goserelin, leuprolide, and tamoxifen; (24) natural antineoplastics, including but not limited to aldesleukin, interleukin-2, docetaxel, etoposide (VP-16), interferon alpha, paclitaxel, and tretinoin (ATRA); (25) antibiotic natural antineoplastics, including but not limited to bleomycin, actinomycin, daunorubicin, doxorubicin, and mitomycin; (26) vinca alkaloid natural antineoplastics, including but not limited to vinblastine and vincristine; (27) autonomic agents, including but not limited to nicotine; (28) anticholinergic autonomic agents, including but not limited to benztropine and trihexyphenidyl; (29) antimuscarinic anticholinergic autonomic agents, including but not limited to atropine and oxybutynin; (30) ergot alkaloid autonomic agents, including but not limited to bromocriptine; (31) cholinergic agonist parasympathomimetics, including but not limited to pilocarpine; (32) cholinesterase inhibitor parasympathomimetics, including but not limited to pyridostigmine; (33) alpha-blocker sympatholytics, including but not limited to prazosin; (34) beta-blocker sympatholytics, including but not limited to atenolol; (35) adrenergic agonist sympathomimetics, including but not limited to albuterol and dobutamine; (36) cardiovascular agents, including but not limited to aspirin (ASA), plavix (Clopidogrel bisulfate) etc; (37) beta-blocker antianginals, including but not limited to atenolol and propranolol; (38) calcium-channel blocker antianginals, including but not limited to nifedipine and verapamil; (39) nitrate antianginals, including but not limited to isosorbide dinitrate (ISDN); (40) cardiac glycoside antiarrhythmics, including but not limited to digoxin; (41) class I anti-arrhythmics, including but not limited to lidocaine, mexiletine, phenytoin, procainamide, and quinidine; (42) class II antiarrhythmics, including but not limited to atenolol, metoprolol, propranolol, and timolol; (43) class III antiarrhythmics, including but not limited to amiodarone; (44) class IV antiarrhythmics, including but not limited to diltiazem and verapamil; (45) alpha-blocker antihypertensives, including but not limited to prazosin; (46) angiotensin-converting enzyme inhibitor (ACE inhibitor) antihypertensives, including but not limited to captopril and enalapril; (47) beta blocker antihypertensives, including but not limited to atenolol, metoprolol, nadolol, and propanolol; (48) calcium-channel blocker antihypertensive agents, including but not limited to diltiazem and nifedipine; (49) central-acting adrenergic antihypertensives, including but not limited to clonidine and methyldopa; (50) diurectic antihypertensive agents, including but not limited to amiloride, furosemide, hydrochlorothiazide (HCTZ), and spironolactone; (51) peripheral vasodilator antihypertensives, including but not limited to hydralazine and minoxidil; (52) antilipemics, including but not limited to gemfibrozil and probucol; (53) bile acid sequestrant antilipemics, including but not limited to cholestyramine; (54) HMG-CoA reductase inhibitor antilipemics, including but not limited to lovastatin and pravastatin; (55) inotropes, including but not limited to amrinone, dobutamine, and dopamine; (56) cardiac glycoside inotropes, including but not limited to digoxin; (57) thrombolytic agents or enzymes, including but not limited to alteplase (TPA), anistreplase, streptokinase, and urokinase; (58) dermatological agents, including but not limited to colchicine, isotretinoin, methotrexate, minoxidil, tretinoin (ATRA); (59) dermatological corticosteroid anti-inflammatory agents, including but not limited to betamethasone and dexamethasone; (60) antifungal topical antiinfectives, including but not limited to amphotericin B, clotrimazole, miconazole, and nystatin; (61) antiviral topical anti-infectives, including but not limited to acyclovir; (62) topical antineoplastics, including but not limited to fluorouracil (5-FU); (63) electrolytic and renal agents, including but not limited to lactulose; (64) loop diuretics, including but not limited to furosemide; (65) potassium-sparing diuretics, including but not limited to triamterene; (66) thiazide diuretics, including but not limited to hydrochlorothiazide (HCTZ); (67) uricosuric agents, including but not limited to probenecid; (68) enzymes including but not limited to RNase and DNase; (69) immunosupressive agents, including but not limited to cyclosporine, steroids, methotrexate, tacrolimus, sirolimus, rapamycin; (70) antiemetics, including but not limited to prochlorperazine; (71) salicylate gastrointestinal anti-inflammatory agents, including but not limited to sulfasalazine; (72) gastric acid-pump inhibitor anti-ulcer agents, including but not limited to omeprazole; (73) H2-blocker anti-ulcer agents, including but not limited to cimetidine, famotidine, nizatidine, and ranitidine; (74) digestants, including but not limited to pancrelipase; (75) prokinetic agents, including but not limited to erythromycin; (76) opiate agonist intravenous anesthetics including but not limited to fentanyl; (77) hematopoietic antianemia agents, including but not limited to erythropoietin, filgrastim (G-CSF), and sargramostim (GM-CSF); (78) coagulation agents, including but not limited to antihemophilic factors 1-10 (AHF 1-10); (79) anticoagulants, including but not limited to warfarin, heparin (important for heparin bound polymers and cardiopulmonary bypass pump circuits), argatroban—each works by a different mechanism and is metabolized differently; (80) growth receptor inhibitors, including but not limited to erlotinib and gefetinib; (82) abortifaciens, including but not limited to methotrexate; (83) antidiabetic agents, including but not limited to insulin; (84) oral contraceptives, including but not limited to estrogen and progestin; (85) progestin contraceptives, including but not limited to levonorgestrel and norgestrel; (86) estrogens including but not limited to conjugated estrogens, diethylstilbestrol (DES), estrogen (estradiol, estrone, and estropipate); (87) fertility agents, including but not limited to clomiphene, human chorionic gonadatropin (HCG), and menotropins; (88) parathyroid agents including but not limited to calcitonin; (89) pituitary hormones, including but not limited to desmopressin, goserelin, oxytocin, and vasopressin (ADH); (90) progestins, including but not limited to medroxyprogesterone, norethindrone, and progesterone; (91)thyroid hormones, including but not limited to levothyroxine; (92) immunobiologic agents, including but not limited to interferon beta-1b and interferon gamma-1b; (93) immunoglobulins, including but not limited to immune globulin IM, IMIG, IGIM and immune globulin IV, IVIG, IGIV; (94) amide local anesthetics, including but not limited to lidocaine; (95) ester local anesthetics, including but not limited to benzocaine and procaine; (96) musculoskeletal corticosteroid anti-inflammatory agents, including but not limited to beclomethasone, betamethasone, cortisone, dexamethasone, hydrocortisone, and prednisone; (97) musculoskeletal anti-inflammatory immunosuppressives, including but not limited to azathioprine, cyclophosphamide, and methotrexate; (98) musculoskeletal nonsteroidal anti-inflammatory drugs (NSAIDs), including but not limited to diclofenac, ibuprofen, ketoprofen, ketorlac, and naproxen; (99) skeletal muscle relaxants, including but not limited to baclofen, cyclobenzaprine, and diazepam; (100) reverse neuromuscular blocker skeletal muscle relaxants, including but not limited to pyridostigmine; (101) neurological agents, including but not limited to nimodipine, riluzole, tacrine and ticlopidine; (102) anticonvulsants, including but not limited to carbamazepine, gabapentin, lamotrigine, phenytoin, and valproic acid; (103) barbiturate anticonvulsants, including but not limited to phenobarbital and primidone; (104) benzodiazepine anticonvulsants, including but not limited to clonazepam, diazepam, and lorazepam; (105) anti-parkisonian agents, including but not limited to bromocriptine, levodopa, carbidopa, and pergolide; (106) anti-vertigo agents, including but not limited to meclizine; (107) opiate agonists, including but not limited to codeine, fentanyl, hydromorphone, methadone, and morphine; (108) opiate antagonists, including but not limited to naloxone; (109) beta-blocker anti-glaucoma agents, including but not limited to timolol; (110) miotic anti-glaucoma agents, including but not limited to pilocarpine; (111) ophthalmic aminoglycoside antiinfectives, including but not limited to gentamicin, neomycin, and tobramycin; (112) ophthalmic quinolone anti-infectives, including but not limited to ciprofloxacin, norfloxacin, and ofloxacin; (113) ophthalmic corticosteroid anti-inflammatory agents, including but not limited to dexamethasone and prednisolone; (114) ophthalmic nonsteroidal anti-inflammatory drugs (NSAIDs), including but not limited to diclofenac; (115) antipsychotics, including but not limited to clozapine, haloperidol, and risperidone; (116) benzodiazepine anxiolytics, sedatives and hypnotics, including but not limited to clonazepam, diazepam, lorazepam, oxazepam, and prazepam; (117) psychostimulants, including but not limited to methylphenidate and pemoline; (118) antitussives, including but not limited to codeine; (119) bronchodilators, including but not limited to theophylline; (120) adrenergic agonist bronchodilators, including but not limited to albuterol; (121) respiratory corticosteroid anti-inflammatory agents, including but not limited to dexamethasone; (122) antidotes, including but not limited to flumazenil and naloxone; (123) heavy metal antagonists/chelating agents, including but not limited to penicillamine; (124) deterrent substance abuse agents, including but not limited to disulfiram, naltrexone, and nicotine; (125) withdrawal substance abuse agents, including but not limited to bromocriptine; (126) minerals, including but not limited to iron, calcium, and magnesium; (127) vitamin B compounds, including but not limited to cyanocobalamin (vitamin B12) and niacin (vitamin B3); (128) vitamin C compounds, including but not limited to ascorbic acid; (129) vitamin D compounds, including but not limited to calcitriol; (130) antiparasitic compounds including but not limited to metronidazole; (131) bronchodilators, including but not limited to salmeterol, and beta agonists; (132) leukotriene blockers/modifiers including montelukast or zileuton; (133) inhaled steroids including but not limited to fluticasone, beclomethasone, or budesonide. Anti-bleeding (hemostatic) agents including but not limited to protamine and antihelminth, radiation sensitizers, and other drugs including but not limited to racin and cyclosporine are also included. Additional anticancer drugs including but not limited to pycnidione as well as anti-Myc inhibitors.

In addition to the foregoing, the following less common drugs can also be used as encapsulated within the particles of the invention or in combination with the particles of the invention for targeted delivery of the drugs: chlorhexidine; estradiol cypionate in oil; estradiol valerate in oil; flurbiprofen; flurbiprofen sodium; ivermectin; levodopa; nafarelin; and somatropin. Further, the following drugs can also be used: pycnidione, cyclosporine, recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan. Further still, the following intravenous products can be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT).

Further specific examples of useful pharmaceutical agents from the above categories include: (a) anti-neoplastics including but not limited to androgen inhibitors, antimetabolites, cytotoxic agents, receptor inhibitors, and immunomodulators; (b) anti-tussives including but not limited to dextromethorphan, dextromethorphan hydrobromide, noscapine, carbetapentane citrate, and chlorphedianol hydrochloride; (c) antihistamines including but not limited to chlorpheniramine maleate, phenindamine tartrate, pyrilamine maleate, doxylamine succinate, and phenyltoloxamine citrate; (d) decongestants including but not limited to phenylephrine hydrochloride, phenylpropanolamine hydrochloride, pseudoephedrine hydrochloride, and ephedrine; (e) various alkaloids including but not limited to codeine phosphate, codeine sulfate and morphine; (f) mineral supplements including but not limited to potassium chloride, zinc chloride, calcium carbonates, magnesium oxide, and other alkali metal and alkaline earth metal salts; (g) ion exchange resins including but not limited to cholestryramine; (h) anti-arrhythmics including but not limited to N-acetylprocainamide; (i) antipyretics and analgesics including but not limited to acetaminophen, aspirin and ibuprofen; (j) appetite suppressants including but not limited to phenyl-propanolamine hydrochloride or caffeine; (k) expectorants including but not limited to guaifenesin; (l) antacids including but not limited to aluminum hydroxide and magnesium hydroxide; (m) biologicals including but not limited to peptides, polypeptides, proteins and amino acids, hormones, interferons or cytokines, and other bioactive peptidic compounds, including but not limited to interleukins 1-18 including mutants and analogues, RNase, DNase, luteinizing hormone releasing hormone (LHRH) and analogues, gonadotropin releasing hormone (GnRH), transforming growth factor-.beta. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; and (n) anti-infective agents including but not limited to antifungals, anti-virals, antihelminths, antiseptics and antibiotics. Additional agents include hemoglobin, oxygen, nitric oxide, silver or other nobel metals. Additional agents include drugs that have renal toxicity and cardio toxicity, wherein the delivery with the particles assists in reducing the renal or cardiotoxicity by delivering the drugs in a targeted manner to a tissue site other than kidneys or the heart.

Examples of specific drugs that can be used include, but are not limited to asparaginase; bleomycin; busulfan; capecitabine; carboplatin; carmustine; chlorambucil; cisplatin; cyclophosphamide; cytarabine; dacarbizine; dactinomycin; daunorubicin; dexrazoxane; docetaxel; doxorubicin; erlotinibil/gefetinib; etoposide; floxuridine; fludarabine; fluoruracil; gemcitabine; 10-hydrocamptothecin; hydroxyurea; idarubicin; ifosfamide; irinotecan; lomustine; mechlorethamine; melphalan; mercaptopurine; methotrexate; mitomycin; mitotane; mitoxantrone; paclitaxel; pentostatin; plicamycin; pemextred procarbazine; rituximabe; streptozocin; teniposid; thioguanine; thiotepa; vinplastine; vinchristine; and vinorelbineor derivates of these molecules.

Examples of anticancer, antineoplastic agents are camptothecins. These drugs are antineoplastic by virtue of their ability to inhibit topoisomerase I. Camptothecin is a plant alkaloid isolated from trees indigenous to China and analogs thereof including but not limited to 9-aminocamptothecin, 9-nitrocamptothecin, 10-hydroxycamptothecin, 10,11-methy lenedioxycamptothecin, 9-nitro 10,11, methylenehydroxycamptothecin, 9-chloro-10,11-methylenehydroxycamptothecin, 9-amino-10,11-methylenehydroxycamptothecin, 7-ethyl-10-hydroxycamptothecin (SN-38), topotecan, DX-8951, Lurtotecan (GII147221C), and other analogs (collectively referred to herein as camptothecin drugs) are presently under study worldwide in research laboratories for treatment of colon, breast, and other cancers.

Additionally, the pharmaceutical agent can be a radiosensitizer, including but not limited to metoclopramide, sensamide or neusensamide (manufactured by Oxigene); profiromycin (made by Vion); RSR13 (made by Altos); THYMITAQ® (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); agents that minimize hypoxia, and the like. The biologically active substance can be selected from the group consisting of peptides, polypeptides, proteins, amino acids, polysaccharides, growth factors, hormones, anti-angiogenesis factors, interferons or cytokines, elements, and pro-drugs. In a particularly preferred embodiment, the biologically active substance is a therapeutic drug or pro-drug, most preferably a drug selected from the group consisting of chemotherapeutic agents and other antineoplastics including but not limited to paclitaxel, antibiotics, anti-virals, antifungals, anesthetics, antihelminths, anti-inflammatories, and anticoagulants.

In certain useful embodiments, the agent is a biologically active substance that is a therapeutic drug or pro-drug, most preferably a drug selected from the group consisting of chemotherapeutic agents and other antineoplastics including but not limited to paclitaxel, carboplatin and cisplatin; nitrosourea alkylating antineoplastic agents, including but not limited to carmustine (BCNU); eupenifeldin, fluorouracil (5-FU), gemcitabine, and verticillin A; hormonal antineoplastics, including but not limited to goserelin, leuprolide, and tamoxifen; receptor inhibitors including but not limited to erlotinib, gefetinib, Sunitinib, Imatinib, or anti-ckit inhibitors (registered name is Gleevec); natural antineoplastics, including but not limited to aldesleukin, interleukin-2, docetaxel, etoposide (VP-16), interferon alpha, paclitaxel, and tretinoin (ATRA). Furthermore, the agent to delivered is dissolved in an aqueous solution or in an aqueous solution containing another compound to increase the agent's solubility including but not limited to cremaphor E/L for paclitaxel.

Biologically active agents amenable for use with the new polymers described herein include, without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Useful active agents amenable for use in the new compositions include growth factors, including but not limited to transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are preferred. Members of the TGF supergene family include the beta-transforming growth factors (for example, TGF-b1, TGF-b2, and TGF-b3); bone morphogenetic proteins (for example, BMP-1, BMP-2, BMP-3, BMP-4, BMP-5, BMP-6, BMP-7, BMP-8, and BMP-9); heparin-binding growth factors (for example, fibroblast growth factor (FGF), epidermal growth factor (EGF), platelet-derived growth factor (PDGF), and insulin-like growth factor (IGF)); inhibins (for example, Inhibin A, Inhibin B); growth differentiating factors (for example, GDF-1); and activins (for example, Activin A, Activin B, and Activin AB).

Non-limiting examples of broad categories of useful pharmaceutical agents include the following therapeutic categories: anabolic agents, anesthetic agents, antacids, anti-asthmatic agents, anticholesterolemic and anti-lipid agents, anti-coagulants, anti-convulsants, antidiarrheals, antiemetics, anti-infective agents, anti-inflammatory agents, antimanic agents, anti-nauseants, antineoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, small molecule inhibitors, receptor enzymes, stimulants, thyroid and anti-thyroid agents, uterine relaxants, vitamins, and prodrugs.

More specifically, non-limiting examples of useful pharmaceutical agents include the following therapeutic categories: analgesics, including but not limited to nonsteroidal anti-inflammatory drugs, opiate agonists and salicylates; antihistamines, including but not limited to H1-blockers and H2-blockers; anti-infective agents, including but not limited to anthelmintics, antianaerobics, antibiotics, aminoglycoside antibiotics, antifungal antibiotics, cephalosporin antibiotics, macrolide antibiotics, miscellaneous beta-lactam antibiotics, penicillin antibiotics, quinolone antibiotics, sulfonamide antibiotics, tetracycline antibiotics, antimycobacterials, anti-tuberculosis antimycobacterials, antiprotozoals, antimalarial antiprotozoals, antiviral agents, anti-retroviral agents, scabicides, and urinary anti-infectives; antineoplastic agents, including but not limited to alkylating agents, nitrogen mustard aklylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, including but not limited to anticholinergics, antimuscarinic anticholinergics, ergot alkaloids, parasympathomimetics, cholinergic agonist parasympathomimetics, cholinesterase inhibitor para-sympathomimetics, sympatholytics, alpha-blocker sympatholytics, beta-blocker sympatholytics, sympathomimetics, and adrenergic agonist sympathomimetics; cardiovascular agents, including but not limited to antianginals, betablocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, including but not limited to antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, including but not limited to acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, including but not limited to pancreatic enzymes and thrombolytic enzymes; gastrointestinal agents, including but not limited to antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, including but not limited to inhalation anesthetics, halogenated inhalation anesthetics, intravenous anesthetics, barbiturate intravenous anesthetics, benzodiazepine intravenous anesthetics, and opiate agonist intravenous anesthetics; hematological agents, including but not limited to antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, including but not limited to abortifacients, adrenal agents, corticosteroid adrenal agents, androgens, antiandrogens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, including but not limited to immunoglobulins, immunosuppressives, toxoids, and vaccines; local anesthetics, including but not limited to amide local anesthetics and ester local anesthetics; musculoskeletal agents, including but not limited to anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, including but not limited to anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, including but not limited to antiglaucoma agents, beta-blocker anti-gluacoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, including but not limited to antidepressants, heterocyclic antidepressants, monoamine oxidase inhibitors (MAOIs), sclerosants including but not limited to talc, alcohol or doxycyclin, selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, including but not limited to antitussives, bronchodilators, adrenergic agonist bronchodilators, antimuscarinic bronchodilators, expectorants, mucolytic agents, respiratory anti-inflammatory agents, leukotriene modifiers and respiratory corticosteroid anti-inflammatory agents; toxicology agents, including but not limited to antidotes, heavy metal antagonists/chelating agents, substance abuse agents, deterrent substance abuse agents, and withdrawal substance abuse agents; minerals; and vitamins, including but not limited to vitamin A, vitamin B, vitamin C, vitamin D, vitamin E, and vitamin K.

Formulation and Administration

In one aspect, the methods described herein provide a method for delivering an agent to a subject in need thereof. In one embodiment, the subject is a mammal. In another embodiment, the mammal is a human, although the approach is effective with respect to all mammals. The method comprises administering to the subject an effective amount of a pharmaceutical composition comprising an agent and a polymer described herein, in a pharmaceutically acceptable carrier. The dosage range for an agent depends upon the potency, and includes amounts large enough to produce the desired effect, e.g., a reduction in a symptom or marker of a disease. The dosage should not be so large as to cause unacceptable adverse side effects. Generally, the dosage of an agent will vary with the type of agent (e.g., an antibody or fragment, small molecule, siRNA, etc.), and with the age, condition, and sex of the patient. The dosage can be determined by one of skill in the art and can also be adjusted by the individual physician in the event of any complication. Typically, the dosage ranges for a free drug (i.e., not in a polymer drug delivery device) are from 0.001 mg/kg body weight to 5 g/kg body weight. In some embodiments, the dosage range for a free drug is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range for a free drug is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 mg/kg body weight to 30 mg/kg body weight. Alternatively, the dose range will be titrated to maintain serum levels between 5 μg/mL and 30 μg/mL. The dose of a bioactive agent delivered by the compositions described herein can be tailored to produce a similar free drug concentration (e.g., a therapeutically effective concentration) in e.g., blood as is achieved using a standard method of administration of the free drug.

Given the ability of a bioactive agent in a composition as described herein to provide sustained release of a free bioactive agent over time, it is also contemplated that the dose of the agent present in the polymeric composition is higher than the amount of free agent administered alone. This aspect is especially important for reducing dose-limiting toxicities of a free agent by permitting a slow, sustained release of a therapeutic amount of an agent from a polymeric composition. Thus, the amount of a bioactive agent administered using the compositions described herein agent is at least 5% higher than the dose necessary for a free drug to produce an equivalent effect (e.g., 50% reduction in a symptom or marker of disease); preferably the amount of an agent administered with the polymeric composition is at least 10% higher, at least 20% higher, at least 30% higher, at least 40% higher, at least 50% higher at least 60% higher, at least 70% higher, at least 80% higher, at least 90% higher, at least 95% higher, at least 1-fold higher, at least 2-fold higher, at least 5-fold higher, at least 50-fold higher, at least 100-fold higher, at least 1000-fold higher or more than the amount of free agent administered to achieve an equivalent bioactive effect.

Administration of the doses recited above can be repeated for a limited period of time. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy. Continuous, relatively low maintenance doses are contemplated after an initial higher therapeutic dose. It will be clear to one of skill in the art that the slow-release properties of the polymeric compositions described herein permit the compositions to be administered less frequently than that of the free drug. For example, the polymeric compositions described herein can be administered every 36 h, every 48 h, every 3 days, every 4 days, every 5 days, every 6 days, every week, every two weeks, every three weeks, every four weeks, ever six weeks, or longer. In some embodiments, the compositions described herein are administered only once, for example, the composition is implanted near a tumor or other site near the desired drug release, or otherwise administered as a bolus composition. In one embodiment, composition releases the bioactive agent continuously at a therapeutic dose for at least 7 days, at least 10 days, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or longer.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. The agent can be administered systemically, or alternatively, can be administered directly to a desired site, e.g., a tumor e.g., by intratumor injection, implantation near or on the tumor, or by injection into the tumor's primary blood supply.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

In some embodiments, the drug-eluting composition is administered on the surface of cancerous tissue or the site remaining after surgical resection and releases one or more anticancer agents in a gradual and prolonged manner to reduce or kill tumors and/or prevent recurrence or metastasis in tissues including but not limited to lung, colon, ovary, breast, pancreas, mesothelium, connective tissue, stomach, liver, and kidney. As such these drug-eluting compositions are of use for treating sarcomas, mesothelioma, lung cancer, breast cancer, colon cancer, ovarian cancer, etc. In some embodiments, the composition is administered to the resection margins after local surgery following the removal of a tumor to destroy residual remaining disease and prevent recurrence. The composition can be loaded with one or more prohealing drugs such as anti-inflammatories in addition to anticancer agents to ensure adequate healing of noncancerous tissue. In some embodiments, the composition is implanted e.g., stapled directly over the surface of diseased or treated tissue. The implants can also be combined with other therapeutic modalities, including radiotherapy, other chemotherapeutic agents administered systemically or locally, immunotherapy, or radiofrequency ablation. In some embodiments, the implant is administered to the site of disease utilizing methods currently used during standard surgical resection procedures, for example by simultaneously administering the composite using the surgical stapler during the removal of the primary tumor. By the appropriate selection of polymer, doping agent, and bioactive agent, a flexible implant capable of controlled release of a therapeutic agent to the surface of a tissue can be constructed.

In some embodiments, the chemotherapeutic agent is released at the site of disease for at least 7 days, at least 10 days, at least two weeks, at least 3 weeks, at least 1 month, at least 2 months, at least 3 months, at least 6 months or more.

In some embodiments, the implant is surgically stapled in direct contact with the tissue surface at the site of disease. In some embodiments, the implant is affixed in direct contact with the tissue surface at the site of disease using an adhesive or glue. The methods of administration can be used to administer any of the embodiments of the compositions described herein, or combination thereof.

It is further appreciated that certain features of the invention, which are, for clarity, described in the context of separate embodiments, can also be provided in combination in a single embodiment.

Applications for Polymer/Agent Compositions

The polymers provided herein can be utilized to promote healing or prevent disease by targeting prophylactic or therapeutic drug to a local and/or regional areas.

Accordingly, in some embodiments, the invention provides methods of treatment of diseases and disorders comprising the step of delivering the particles of the invention to a specific tissue location wherein a therapeutic agent is desired to be delivered. In some embodiments, the polymer particles are polymer particles without a drug also referred to as "empty polymer particles" and the particles are administered locally to the location wherein the drug is desired to be delivered, and the drug is administered systemically.

In some embodiments, the polymer particle is delivered first to the tissue site and the agent is administered subsequently, wherein the agent concentrates at the site of the polymer particle, thus delivering a targeted treatment of the tissue or location wherein the polymer particles have been delivered.

The polymers provided herein can also be used for a variety of applications including, but not limited to repair of an injured or malformed tissue, organ, bone, or amelioration of genetic defect.

In some embodiments, the invention provides a method of treating a malignancy in a subject, the method comprising administering to the subject one or more of the polymer particles of the invention to a location or multiple locations of the malignancy, and administering to the subject an agent that is toxic to the drug, such as a chemotherapeutic drug.

The drug or agent, such as a therapeutic agent, can be administered within the polymer particles, before administering the polymer particles, simultaneously with administering the polymer particles or after administering the polymer particles.

The treatment can be treatment of early, late or previously treated malignancy or it can include prevention or inhibition of recurrence of a malignancy that has been surgically removed or locally treated following radiofrequency ablation or radiosurgery/radiation therapy. The treatment may include avoidance of locoregional lymph node metastasis, augmentation of local wound healing and decrease in infection, manipulation of structure and abnormal scar formation to treat a chronic condition, and for the treatment of postoperative pain.

In some embodiments, the polymers provided herein are used to treat cancer. For example, the polymers provided herein can be used to treat lung, colon, prostate, pancreas, ovarian, or breast cancer or mesothelioma or sarcoma. The polymeric particles of the invention are also useful for bone marrow transplantation to target residual tumor cells in the graft (i.e. to target lymphomas and leukemias).

Typically, the polymer particles are administered locally. For example, the polymeric particles can be injected or infused into or around inoperable tumors to locally deliver drugs, such as chemotherapy, immunomodulators, or sensitizers etc, or injected/infused near the site of the operative incision, such as antibiotics, anesthetics or growth/healing factors, thereby avoiding side effects associated with systemic delivery. The polymeric particles provided herein can also be administered at a site of surgery to treat local residual tumor cells and to be carried by the lymph fluid to locoregional nodes. The particles can become trapped at the lymph nodes, allowing delivery of agents to tumor cells that also commonly migrate to lymph nodes. Cells that commonly migrate to lymph nodes include tumor cells and immune cells such as T cells or dendritic cells, and thus direct presentation of antigens, immunomodulating agents etc., by the particles can be used to enhance the immune system. Thus, the particles can be used to treat tumors systemically either by targeting the tumor cells directly of by upregulating the immune system to fight the tumor.

The drug or agent can be administered locally near the location of the particles or systemically, allowing it to concentrate to the location of the polymeric particles.

The polymeric particles provided herein can also be administered to sites where tumor regrowth is likely to occur. The particles can be administered to areas where, as a consequence of disease (COPD, inflammatory bowl disease etc) or systemic chemotherapy, poor healing can result in major complications. In addition, the particles can be administered to the margins of a surgical excision or resection, or to sites following local ablative therapy. For such applications, the polymeric particles can be prepared to adhere to the surgical margin or be retained within the confines and perimeter of the mass.

Any method of adhering particles to biological tissue can be used for this application. For example, the polymeric particles provided herein can be coated with PLURONIC® F127. In another embodiment, the particles are entrapped within a gel, hydrogel, adhesive, or sealant to increase there resident time at the implant site The particles can also be used to coat medican devices such as stents and artificial body parts.

In addition, other types of surgery can benefit from the use of the polymeric particles described herein. For example, particles can be delivered and then used with antibiotics for local delivery at a surgical site. The local concentration of the antibiotics can be prolonged at the surgical site to reduce the risk of post-surgical infections and complications, such as *clostridium difficile* infection. Accordingly, the invention provides a method for local delivery of antibiotics comprising administering to a subject in need of local antibiotic treatment the one or more of the polymeric particles of the invention and an antibiotic or a mixture of antibiotics. This method provides an alternative to the use and risk of systemic antibiotics.

The particles can contain and or be used with anesthetics, such as local amide anesthetics, IV narcotics, or anti-inflammatory agents (steroids, NSAIDS etc) to reduce the discomfort of patients, particularly surgical incisions or sites of injury or inflammation. The use of such polymeric materials can reduce morbidity secondary to delirium and constipation by decreasing systemic levels of narcotics, thus decreasing the length of hospital stay for patients, and reduce overall health care costs.

In certain embodiments, the polymeric particles are provided in aqueous or organic solutions, or combinations thereof. Examples of the aqueous solutions include but are not limited to water, buffered aqueous media, saline, buffered saline, solutions of amino acids, solutions of sugars, solutions of vitamins, solutions of carbohydrates or combinations of any two or more thereof. Examples of the organic solutions include but are not limited to DMSO, ethanol, methanol, tetrahydrofuran (THF), dichloromethane, dimethylformamide (DMF), hexane or toluene or combinations of any two or more thereof.

The polymeric microparticles, nanoparticles, and other polymer forms provided herein can be used for in vitro and in vivo local drug concentration. Depending upon the selected polymer, the rate of drug release can be delayed or immediate. In certain embodiments, the polymers provided herein can be used for prolonged drug delivery after an initial period of quiescence to permit surgical healing to occur.

Alternatively, the particles can swell and become lodged, embedded, entrapped, or otherwise immobilized at a certain target location. For example, swelled particles can become lodged or embedded within a specific tissue, organ, cavity, node, tubule, bronchus or capillary and can be used to occlude blood flow as an embolization agent for bleeding, arteriovenous malformations, or tumor devascularization or can be used to prevent airflow to a specific portion of the lung as for endoscopic lung volume reduction surgery, to cite only two examples of potential uses of this property. The resulting particle in the cell or tissue site can be used as a depot to concentrate agent that has been subsequently delivered. Methods of using polymer particles that localize to a tissue site and then target and concentrate a subsequently delivered agent to the site are described, for example, in WO2013059295, content of which is incorporated herein by reference in its entirety.

Particle swelling can be triggered by pH change from an exogenous agent added to the polymer, a change within a cavity or vessel as can occur in ischemic or infected tissues or within an intracellular compartment such as an endosome. Such particles can also be manufactured to deliver agents that manipulate healing or fibrosis to facilitate permanent or temporary closure of the occluded lumen or cavity.

The polymers provided herein can be used to deliver or concentrate any agent or agents. The agent can be in any pharmaceutically acceptable form, including pharmaceutically acceptable salts. A large number of pharmaceutical agents are known in the art and are amenable for use in the pharmaceutical compositions of the polymeric materials described herein. Acceptable agents are described elsewhere herein, and include, but are not limited to, chemotherapeutic agents, such as radiosensitizers, receptor inhibitors and agonists or other anti-neoplastic agent; small molecules, peptides, DNA/RNA nucleotides, immune modulators and bioactive agents, such as cytokines, growth factors or steroids with or without the co-incorporation of tumor or pathogen antigens to increase the anti-neoplastic response as a means of vaccine development; local anesthetic agents; or antibiotics.

The biologically active substances and agents are used in varying amounts. While the effective amount of a biologically active substance will depend on the particular material being used, amounts of the biologically active substance from about 1% to about 95%+weight/weight of the polymer can be desirable. Lesser amounts can be used to achieve efficacious levels of treatment for certain biologically active substances.

The amount of drug delivered will depend on the therapeutic range of the drug, its toxicity when and how it is delivered, and the clinical characteristics of the patient being treated as well as the interaction between the polymer nanoparticle and the agent which concentrates therein. The number of particles delivered to a site is selected depending on factors such as 1) the amount of agent delivered per particle, 2) the therapeutic range of the agent, 3) the local toxicity of the agent, and 4) the clinical characteristics of the patient being treated. The development of dosages based on these parameters is routinely performed by those skilled in the art of pharmacology and clinical medicine. For example, between $1 \times 10^4$ and $1 \times 10^{12}$ particles/cm can be administered to a biological area.

The particles of the invention can be microparticles and nanoparticles. In one embodiment, the size of the polymer particles described herein are between 2 and 100 nm in diameter. In other embodiments, the size of the polymer particle is between 0.002-10 micrometers in diameter. In other embodiments, the size of the polymer particle is between 150 micrometers in diameter. When the polymer nanoparticle swells and expands the size will larger with a preferable size of between 10 and 1000 nm. Other polymeric particles of these sizes or larger can be useful at specific sites, such as an established tumor or where tumor regrowth is prevalent. For example, at a surgical margin, where suturing or stapling has occurred, or within an established or treated tumor such as an ablated cavity secondary to radiofrequency ablation or other therapy, or within a spontaneous cavity such as occurs in squamous cell carcinoma. Placement of polymeric particles within pathologic cavities or biologic spaces (i.e. pleural or peritoneal spaces) could be utilized to treat abscess cavities with antibiotics or to result in sclerosis of the cavity, either with release of specific sclerosing agents such as talc powder, alcohol or doxycyclin as examples or other inflammatory agents. This approach can then be utilized in the treatment of bullous disease in emphysema or infectious diseases such as ecchinococcal cysts for example.

Applications for Polymer Compositions for Degradable Plastics

The alkyl ether and esters of poly(glyceric acid carbonate)s and poly(glyceric acid carbonate)s can be processed into a variety of form factors and used as degradable plastics for industrial applications where polyalkylacrylates and polycarbonates are used.

Polymer Compositions

Exemplary embodiments of the various aspects described herein can be described by one or more of the following numbered paragraphs:

1. A linear, comb, branched, or dendritic oligomer or polymer represented by one of the following formulas:

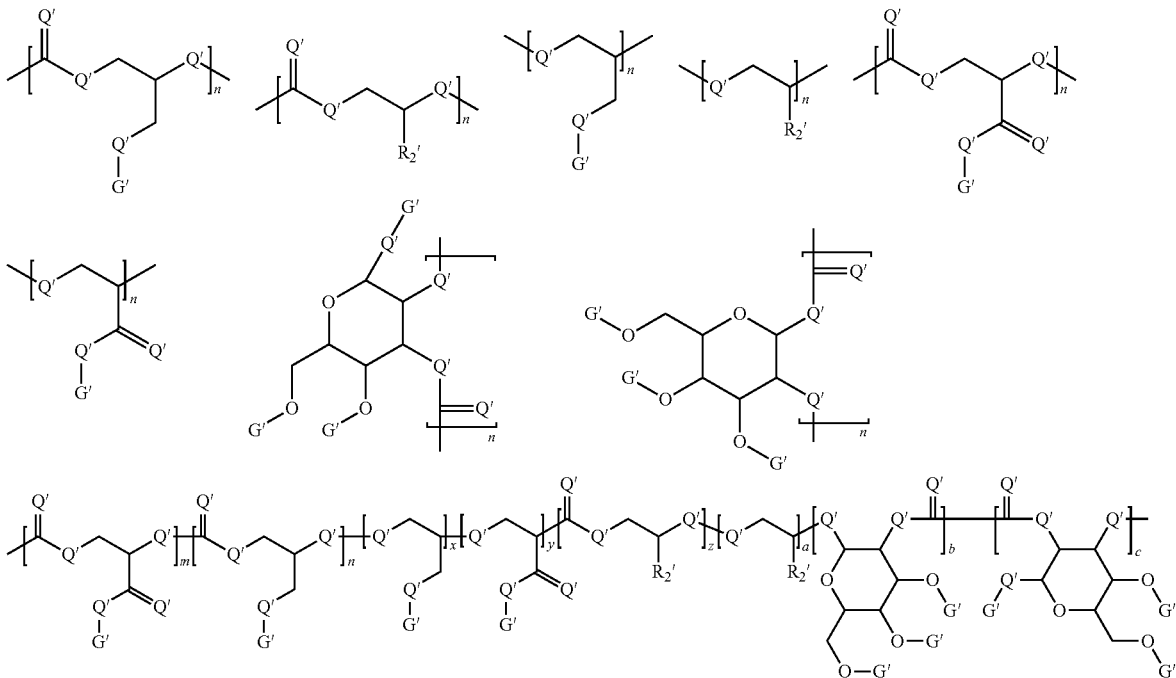

wherein:

each Q' is independently selected from among O, S, Se, or NH;

G' is each independently selected from among the following structures:

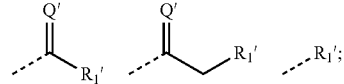

wherein G'1 and G'2 are not the same;

$R'_1$ is selected from among hydrogen, a straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, succinyl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R'_1$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or $R'_1$ is selected from among a photocrosslinkable or ionically crosslinkable group;

$R'_2$ is selected from among hydrogen, a straight or branched alkyl, cycloalkyl, aryl, olefin, silyl, alkylsilyl, arylsilyl, alkylaryl, fluorocarbon, or arylalkyl chain of 1-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

m, n, x, y, z, a, b, or c are each independently selected from an integer of 1-1000;

each polymeric terminal group is selected from among amines, thiols, amides, phosphates, sulphates, hydroxides, metals, alkanes, alkenes and alkynes, provided that $R'_1$ is not hydrogen, phenyl or benzyl when the polymer is

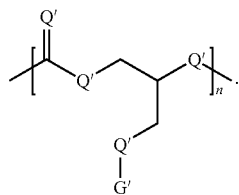

2. The polymer of paragraph 1, wherein Q' is O.
3. The polymer of paragraph 1 or 2, wherein $R'_1$ is selected from among hydrogen or a straight or branched alkyl, cycloalkyl, aryl, olefin, silyl, alkylsilyl, arylsilyl, alkylaryl or arylalkyl chain of 2-50 carbons, wherein each alkyl, cycloalkyl, succinyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.
4. The polymer of any of paragraphs 1-3, wherein $R'_1$ is selected from among hydrogen or a straight or branched alkyl, cycloalkyl, aryl, olefin, silyl, alkylsilyl, arylsilyl, alkylaryl or arylalkyl chain of 3-50 carbons.
5. The polymer of any of paragraphs 1-4, wherein $R'_1$ is selected from among hydrogen or a straight or branched alkyl, alkylaryl or arylalkyl chain of 3-50 carbons.
6. The polymer of any of paragraphs 1-5, wherein $R'_1$ is hydrogen, methyl, ethyl, propyl, butyl or benzyl.
7. The polymer of any of paragraphs 1-6, wherein Q' is O and $R'_1$ is selected from among hydrogen or a straight or branched alkyl, cycloalkyl, aryl, olefin, silyl, alkylsilyl, arylsilyl, alkylaryl or arylalkyl chain of 2-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.
8. The polymer of any of paragraphs 1-7, wherein Q' is O and $R'_1$ is selected from among hydrogen or a straight or branched alkyl, cycloalkyl, aryl, olefin, silyl, alkylsilyl, arylsilyl, alkylaryl or arylalkyl chain of 3-50 carbons.
9. The polymer of any of paragraphs 1-8, wherein Q' is O and $R'_1$ is selected from among hydrogen or a straight or branched alkyl, alkylaryl or arylalkyl chain of 3-50 carbons
10. The polymer of any of paragraphs 1-9, wherein Q' is O and $R'_1$ is selected from among hydrogen or a straight or branched alkyl chain of 3-50 carbons.

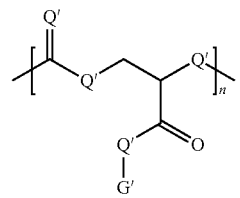

11. The polymer of any of paragraphs 1-10, wherein polymer is of formula and G' is

12. The polymer of paragraph 11, wherein Q' is O.
13. The polymer of paragraph 11 or 12, wherein $R'_1$ is selected from among hydrogen or a straight or branched alkyl, cycloalkyl, aryl, olefin, silyl, alkylsilyl, arylsilyl, alkylaryl or arylalkyl chain of 3-50 carbons.
14. The polymer of any of paragraphs 11-13, wherein $R'_1$ is selected from among hydrogen or a straight or branched alkyl, alkylaryl or arylalkyl chain of 3-50 carbons.
15. The polymer of any of paragraphs 11-14, wherein $R'_1$ is hydrogen or benzyl.
16. The polymer of any of paragraphs 11-15, wherein Q' is O and $R'_1$ is selected from among hydrogen or a straight or branched alkyl, alkylaryl or arylalkyl chain of 3-50 carbons.
17. The polymer of any of paragraphs 11-16, wherein Q' is O and $R'_1$ is hydrogen or benzyl.
18. The polymer of any of paragraphs 1-10, wherein the polymer is of formula

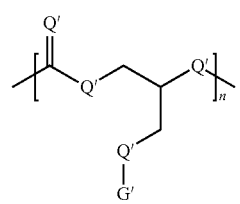

and G' is G' is $$\cdots R_1'.$$

19. The polymer of paragraph 18, wherein Q' is O.
20. The polymer of paragraph 18 or 19, wherein R'$_1$ is selected from among hydrogen or a straight or branched alkyl, cycloalkyl, aryl, olefin, silyl, alkylsilyl, arylsilyl, alkylaryl or arylalkyl chain of 3-50 carbons.
21. The polymer of any of paragraphs 18-20, wherein R'$_1$ is selected from among hydrogen or a straight or branched alkyl, alkylaryl or arylalkyl chain of 3-50 carbons.
22. The polymer of any of paragraphs 18-21, wherein R'$_1$ is methyl, ethyl, propyl, butyl, pentyl or hexyl.
23. The polymer of any of paragraphs 18-22, wherein Q' is O and R'$_1$ is selected from among a straight or branched alkyl, alkylaryl or arylalkyl chain of 3-50 carbons.
24. The polymer of any of paragraphs 18-23, wherein Q' is O and R'$_1$ is butyl.
25. The polymer of any of paragraphs 1-24, wherein the polymer has a MW of less than 1000.
26. The polymer of any of paragraphs 1-25, wherein the polymer has a PDI of >2.
27. The polymer of any of paragraphs 1-26, wherein the polymer has a PDI of >2 and a MW of less than 1000.
28. The polymer of any of claims 1-27, wherein R'$_1$ is a pharmaceutical agent.
29. The polymer of any of claims 1-28, wherein a pharmaceutical agent is conjugated via a succinc acid moiety to between 5 and 95% of the available primary hydroxyl of the polymer back bone.
30. The polymer of any of claims 1-28, wherein paclitaxel is conjugated via a succinc acid moiety to between 5 and 95% of the available primary hydroxyl of the polymer back bone
31. A polymeric film, sheet, mesh, foam, fiber, or particle comprising a polymer of any of paragraphs 1-30.
32. The polymeric particle of paragraph 31, wherein the particle is microparticle or nanoparticle.
33. The polymeric particle of paragraph 31 or 32, comprising a microparticle or nanoparticle.
34. The polymeric particle of any of paragraphs 31-33, wherein the particle comprises a diameter of between about 1 nm and 2 microns.
35. The polymeric particle of any of paragraphs 31-34, wherein the particle comprises a diameter between about 10 nm and 1 microns.
36. The polymeric fiber of paragraph 31, wherein the fiber has a diameter between about 1 nm and 5 mm.
37. The polymeric fiber of paragraph 31 or 36, wherein the fiber has a diameter between about 1 micron and 5 mm.
38. The polymer fiber of paragraph 31 or 36, wherein the fiber has a diameter between about 1 nm and 1 less than micron.
39. The polymeric foam of paragraph 31, wherein the foam has pores having a diameter of between about 1 nm and 10 mm.
40. The polymeric foam of paragraph 31 or 39, wherein the foam has pores having a diameter of between about 1 micron and 10 mm.
41. The polymeric foam of paragraph 31 or 39, wherein the foam has pores having a diameter of between about 1 nm and 1 less than micron.
42. The sheet, film, mesh of paragraph 31, wherein the film, sheet, or mesh is a single layered structure.
43. The sheet, film, or mesh of paragraph 31, wherein the film, sheet, or mesh comprises two or more layers to form a multi-layered structure.
44. The sheet, film, or mesh of paragraph 31, wherein the film, sheet, or mesh comprises two or more layers to form a multi-layered film.
45. The sheet, film, or mesh of paragraph 43 or 43, wherein at a first layer comprises a first polymer selected from polymers of any of paragraph 1-30 and a second layer comprises a second polymer that is different from the first polymer.
46. The sheet, film, or mesh of paragraph 45, wherein the second polymer is not a polymer of any of paragraphs 1-30.
47. The polymeric film, sheet, mesh, foam, fiber, or particle of any of paragraphs 31-46, further comprising additional polymer selected from the group consisting of poly(lactic acid), poly(glycolic acid), poly(lactic-co-glycolic acid), polycaprolactone, poly(trimethlene carbonate), polyester, polycarbonate, polyamide, and any combinations thereof.
48. The polymeric film, sheet, mesh, foam, fiber, or particle of any of paragraphs 31-47, further comprising an agent.
49. The polymeric film, sheet, mesh, foam, fiber, or particle of paragraph 48, wherein the agent is a biologically active agent comprising one or more of an anti-cancer, an anti-biotic, anti-neoplastic, and an analgesic, an angiogenic or agent that promotes healing, anelgesic, anti-inflammatory, or agents that treat or control pain, or avoid scar formation and adhesions.
50. The polymeric film, sheet, mesh, foam, fiber, or particle of paragraph 49, wherein the biologically active agent comprises one or more of asparaginase; bleomycin; busulfan; capecitabine; carboplatin; carmustine chlorambucil; cisplatin; cyclophosphamide; cytarabine; dacarbazine; dactinomycin; daunorubicin; dexrazoxane; docetaxel; doxorubicin; eupenifeldin, etoposide; floxuridine; fludarabine; fluorouracil; gemcitabine; hydroxyurea; idarubicin; ifosfamide; irinotecan; lomustine; mechlorethamine; melphalan; mercaptopurine; methotrexate; mitomycin; mitotane; mitoxantrone; paclitaxel; pemetrexed, pentostatin; plicamycin; procarbazine; rituximab; streptozocin; teniposide; thioguanine; thiotepa; verticillin A, vinblastine; vincristine; and vinorelbine.
51. A method comprising:
    applying a polymeric film, sheet, mesh, foam, fiber, or particle of any of paragraphs 31-50 to a surgical resection margin or within a treated or untreated tumor or cavity, or to target sites of disease away from the surgical margin such as in lymph nodes.
52. A method comprising:
    applying a polymeric film, sheet, mesh, foam, fiber, or particle of any of paragraphs 31-50 to a tissue site, wherein the polymeric film, sheet, mesh, foam, fiber, or particle is secured to the tissue site.
53. The method of paragraph 52, wherein the polymeric film, sheet, mesh, foam, fiber, or particle is secured to the tissue site using sutures, staples or an adhesive.
54. A method comprising:
    applying a polymeric film, sheet, mesh, foam, fiber, or particle of any of paragraphs 31-50 to a surgical resection margin or within a treated or untreated tumor or cavity, or to target sites of disease away from the surgical margin such as in lymph nodes; and delivering an active agent to the surgical resection margin or the treated or untreated tumor or cavity, or the target sites of disease away from the surgical margin.

55. A polymeric melt, wax, viscous liquid, or liquid comprising a polymer of any of paragraphs 1-30.
56. The polymeric melt, wax, viscous liquid, or liquid of paragraph 55, further comprising a lithium salt.
57. The polymeric melt, wax, viscous liquid, or liquid of paragraph 56, wherein the lithium salt is selected from the group consisting of LiBr, LiTFSI, LiPF6, LiBF4, and any combinations thereof.
58. The polymeric melt, wax, viscous liquid, or liquid of paragraph 56 or 57, wherein the polymer has a PDI>2.
59. The polymeric melt, wax, viscous liquid, or liquid of any of paragraphs 56-58, wherein the polymer has a MW of less than 1000.
60. The polymeric melt, wax, viscous liquid, or liquid of any of paragraphs 56-59, wherein the 1 and the polymers have a PDI>2 and/or MW less than 1000.
61. A Li ion, Li-air battery, or Li ion supercapacitor comprising a polymeric melt, wax, viscous liquid, or liquid of any of paragraphs 56-60.
62. A composition comprising a polymeric melt, wax, viscous liquid, or liquid of any of paragraphs 56-60 mixed with an electrolyte solvent.
63. The composition of paragraph 62, wherein the polymeric melt, wax, viscous liquid, or liquid is mixed with EDC, DMC or ionic liquids.
64. A composition comprising a polymer of any of paragraphs 1-30.
65. The composition of paragraph 64, further comprising a second polymer, wherein the second polymer is not a polymer of any of paragraphs 1-30.
66. The composition of paragraph 65, wherein the second polymer is selected from the group consisting of poly (lactic acid), poly(glycolic acid), poly(lactic-co-glycolic acid), polycaprolactone, poly(trimethlene carbonate), polyester, polycarbonate, polyamide, and any combinations thereof.
67. The composition of any of paragraphs 64-66, further comprising a lithium salt.
68. The composition of any of paragraphs 67, wherein the lithium salt is selected from the group consisting of LiBr, LiTFSI, LiPF6, LiBF4, and any combinations thereof.
69. The composition of any paragraphs 64-68, further comprising an electrolyte solvent.
70. The composition of any of paragraphs 64-69, further comprising an ionic liquid.
71. The composition of any of paragraphs 64-70, further comprising EDC or DMC.
72. A Li-ion, Li-air battery, or Li-ion supercapacitor comprising a composition of any of paragraphs 67-71.
73. The composition of any of paragraphs 64-67, further comprising an agent.
74. The composition of paragraph 73, wherein the agent is a biologically active agent comprising one or more of an anti-cancer, an anti-biotic, anti-neoplastic, and an analgesic, an angiogenic or agent that promotes healing, anelgesic, anti-inflammatory, or agents that treat or control pain, or avoid scar formation and adhesions.
75. The composition of paragraph 74, wherein the biologically active agent comprises one or more of asparaginase; bleomycin; busulfan; capecitabine; carboplatin; carmustine chlorambucil; cisplatin; cyclophosphamide; cytarabine; dacarbazine; dactinomycin; daunorubicin; dexrazoxane; docetaxel; doxorubicin; etoposide; eupenifeldin floxuridine; fludarabine; fluorouracil; gemcitabine; hydroxyurea; idarubicin; ifosfamide; irinotecan; lomustine; mechlorethamine; melphalan; mercaptopurine; methotrexate; mitomycin; mitotane; mitoxantrone; paclitaxel; pemetrexed, pentostatin; plicamycin; procarbazine; rituximab; streptozocin; teniposide; thioguanine; thiotepa; verticillin A, vinblastine; vincristine; and vinorelbine.
76. A biodegradable plastic for consumer goods comprising a polymer of any of paragraphs 1-30.
77. A biodegradable plastic for consumer goods comprising a polymer of any of paragraphs 1-30 and a polymer that is not a polymer of any of paragraphs 1-30.
78. A biodegradable plastic for consumer goods comprising a polymeric sheet or film of any of paragraphs 31-50.
79. A biodegradable plastic for consumer goods comprising a polymeric sheet or film of any of paragraphs 31-50 and a polymer that is not a polymer of any of paragraphs 1-30.
80. A biodegradable plastic for electronic products comprising a polymeric sheet or film of any of paragraphs 31-50.
81. A biodegradable plastic for constructions products comprising a polymeric sheet or film of any of paragraphs 31-50.
82. A biodegradable polymer comprising a polymer of any of paragraphs 1-30, wherein the polymer comprises pendent carboxylic acid groups.
83. The biodegradable polymer of paragraph 82, wherein the biodegradable polymer is a biodegradable polyacrylic acid.
84. The biodegradable polymer of paragraph 82 or 83, wherein the biodegradable polymer is an absorbent of liquids and/or moist solids.
85. The biodegradable polymer of any of paragraphs 82-84', wherein the polymer is used as a replacement and/or add on to polyacrylic acid such as an absorbent of liquids and/or moist solids.
86. A copolymer or polymer blend comprising a polymer of any of paragraphs 1-30.
87. The copolymer or polymer blend of paragraph 86, further comprising a polymer that is not a polymer of any of paragraphs 1-30.
88. A superabsorbent polymer, detergent, adhesive, dispersant, or cosmetic comprising a copolymer or polymer blend of paragraph 86 or 87.
89. A superabsorbent polymer, detergent, adhesive, dispersant, or cosmetic of paragraph 88 for use in water/sewage treatment.
90. A cross-linked gel comprising a polymer of any of paragraphs 1-30.
91. The cross-linked gel of paragraph 90, further comprising a polymer that is not a polymer of any of paragraphs 1-30.
92. The cross-linked gel of paragraph 90 or 91, further comprising an agent.
93. The cross-linked gel of paragraph 92, wherein the agent is a biologically active agent comprising one or more of an anti-cancer, an anti-biotic, anti-neoplastic, and an analgesic, an angiogenic or agent that promotes healing, anelgesic, anti-inflammatory, or agents that treat or control pain, or avoid scar formation and adhesions.
94. The cross-linked gel of paragraph 93, wherein the biologically active agent comprises one or more of asparaginase; bleomycin; busulfan; capecitabine; carboplatin; carmustine chlorambucil; cisplatin; cyclophosphamide; cytarabine; dacarbazine; dactinomycin; daunorubicin; dexrazoxane; docetaxel; doxorubicin; etoposide; eupenifeldin, floxuridine; fludarabine; fluorouracil; gemcitabine; hydroxyurea; idarubicin; ifosfamide; irinotecan; lomustine; mechlorethamine; melphalan; mercaptopurine; methotrexate; mitomycin; mitotane; mitoxantrone; paclitaxel; pemetrexed, pentostatin; plicamycin; procarbazine; rituximab; streptozocin; teniposide; thioguanine; thiotepa; verticillin A, vinblastine; vincristine; and vinorelbine.

95. A superabsorbent polymer, detergent, adhesive, dispersant, or cosmetic comprising a cross-linked gel of paragraphs 90-94.

96. The superabsorbent polymer, detergent, adhesive, dispersant, or cosmetic of paragraph 96 for use in water/sewage treatment.

97. A method for treating cancer comprising administering a composition comprising a polymer of any of paragraphs 1-30 and an agent to a subject in need thereof.

Some additional exemplary embodiments of the various aspects described herein can be described by one or more of the following numbered paragraphs:

1. A linear, comb, branched, or dendritic oligomer or polymer represented by one of the following formulas:

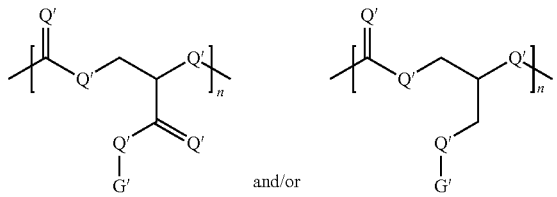

and/or wherein:

Q' is independently selected from among O, S, Se, or NH;
G' is each independently selected from among the following structures:

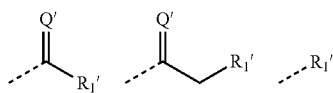

R'1 is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, succinyl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or R'1 is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or R'1 is selected from among a photocrosslinkable or ionically crosslinkable group; each polymeric terminal group is selected from among amines, thiols, amides, phosphates, sulphates, hydroxides, metals, alkanes, alkenes and alkynes.

2. The compound of paragraph 1, wherein Q' is O and R'1 is independently selected from among a straight or branched alkyl, cycloalkyl, aryl, olefin, silyl, alkylsilyl, arylsilyl, alkylaryl or arylalkyl chain of 2-50 carbons, wherein each alkyl, cycloalkyl, succinyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or R'1 is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or R'1 is selected from among a photocrosslinkable or ionically crosslinkable group;

each polymeric terminal group is selected from among amines, thiols, amides, phosphates, sulphates, hydroxides, metals, alkanes, alkenes and alkynes.

3. The compound of paragraph 1, wherein Q' is O and R'1 is independently selected from among a straight or branched alkyl, cycloalkyl, aryl, olefin, silyl, alkylsilyl, arylsilyl, alkylaryl or arylalkyl chain of 2-50 carbons, wherein each alkyl, cycloalkyl, succinyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

4. The compound of paragraph 2, wherein Q' is O and R'1 is selected from among a straight or branched alkyl, cycloalkyl, aryl, olefin, silyl, alkylsilyl, arylsilyl, alkylaryl or arylalkyl chain of 350 carbons.

5. The compound of paragraph 3, wherein Q' is O and R'1 is selected from among a straight or branched alkyl chain of 3-50 carbons.

6. A polymeric film, sheet, mesh, foam, fiber, or particle comprising a polymer of paragraph 1.

7. A polymeric particle of paragraph 6, comprising a microparticle or nanoparticle.

8. A polymeric particle of paragraph 7, wherein the particle comprises a diameter of between about 1 nm and 2 microns.

9. A polymeric particle of paragraph 7, wherein the particle comprises a diameter between about 10 nm and 1 micron.

10. A polymeric fiber of paragraph 6, wherein the fiber diameter is between about 1 nm and 1 micron.

11. A polymeric fiber of paragraph 6, wherein the fiber diameter is between about 1 micron and 5 mm.

12. A polymeric foam of paragraph 6, wherein the diameter of the pore is between about 1 micron and 10 mm.

13. A polymeric foam of paragraph 6, wherein the diameter of the pore is between about 1 nm and 1 micron.

14. The polymeric film, sheet, mesh, foam, fiber, or particle of paragraph 6, further comprising an agent.

15. An active agent loaded polymeric film, sheet, mesh, foam, fiber, or particle of paragraph 14, wherein the agent is a biologically active agent comprising one or more of an anti-cancer, an antibiotic, anti-neoplastic, and an analgesic, an angiogenic or agent that promotes healing, anelgesic, anti-inflammatory, or agents that treat or control pain, or avoid scar formation and adhesions.

16. The polymeric film, sheet, mesh, foam, fiber, or particle of paragraph 14, wherein the biologically active agent comprises one or more of asparaginase; bleomycin; busulfan; capecitabine; carboplatin; carmustine chlorambucil; cisplatin; cyclophosphamide; cytarabine; dacarbazine; dactinomycin; daunorubicin; dexrazoxane; docetaxel;

doxorubicin; etoposide; eupenifeldin, floxuridine; fludarabine; fluorouracil; gemcitabine; hydroxyurea; idarubicin; ifosfamide; irinotecan; lomustine; mechlorethamine; melphalan; mercaptopurine; methotrexate; mitomycin; mitotane; mitoxantrone; paclitaxel; pemetrexed, pentostatin; plicamycin; procarbazine; rituximab; streptozocin; teniposide; thioguanine; thiotepa; verticillin A, vinblastine; vincristine; and vinorelbine.

17. A method of using the polymeric film, sheet, mesh, foam, fiber, or particle of paragraph 14, wherein the material is applied to a surgical resection margin or within a treated or untreated tumor or cavity, or to target sites of disease away from the surgical margin such as in lymph nodes.
18. A method of using the polymeric film, sheet, mesh, foam, fiber, or particle of paragraph 1 or 2, wherein the material is applied to a surgical resection margin or within a treated or untreated tumor or cavity, or to target sites of disease away from the surgical margin such as in lymph nodes.
19. The sheet, film, mesh of paragraph 14, wherein the film, sheet, or mesh is a single layered structure.
20. The sheet, film, or mesh of paragraph 19, further comprising two or more layers to form a multi-layered film.
21. The sheet, film, or mesh of paragraph 20, wherein one layer comprises a first polymer of paragraph 1, and another layer comprises a second polymer different from paragraph 1.
22. The polymeric film, sheet, mesh, foam, fiber, or particle of paragraph 1 or 2, wherein additional polymers are added to the composition comprising one or more of poly(lactic acid), poly(glycolic acid), poly(lactic-co-glycolic acid), polycaprolactone, poly(trimethlene carbonate), polyester, polycarbonate, and polyamide.
23. A method where the polymeric film, sheet, mesh, foam, fiber, or particle paragraph 1 or 2 or 22 is secured in a tissue site using sutures, staples or an adhesive.
24. A method where the polymeric film, sheet, mesh, foam, fiber, or particle paragraph 1 or 2 or 22 is applied to a surgical resection margin or within a treated or untreated tumor or cavity, or to target sites of disease away from the surgical margin such as in lymph nodes and the active agent is subsequently delivered.
25. A polymeric sheet or film of paragraph 1 used as a biodegradable plastic for consumer goods.
26. A polymeric sheet or film of paragraph 1 used as a biodegradable plastic for consumer goods combined with a polymer not of paragraph 1.
27. A copolymer or polymer blends of polymer of paragraph 1 with one or more polymers that are not paragraph 1.
28. A cross-linked gel comprising polymer from paragraph 1 and one or more polymers that are not from paragraph 1.
29. A cross-linked gel from paragraph 28, further comprising an agent.
30. An active agent loaded cross-linked gel of paragraph 29, wherein the agent is a biologically active agent comprising one or more of an anti-cancer, an anti-biotic, antineoplastic, and an analgesic, an angiogenic or agent that promotes healing, anelgesic, anti-inflammatory, or agents that treat or control pain, or avoid scar formation and adhesions.
31. A cross-linked gel from paragraph 28, further comprising an agent, wherein the biologically active agent comprises one or more of asparaginase; bleomycin; busulfan; capecitabine; carboplatin; carmustine chlorambucil; cisplatin; cyclophosphamide; cytarabine; dacarbazine; dactinomycin; daunorubicin; dexrazoxane; docetaxel; doxorubicin; etoposide; eupenifeldin, floxuridine; fludarabine; fluorouracil; gemcitabine; hydroxyurea; idarubicin; ifosfamide; irinotecan; lomustine; mechlorethamine; melphalan; mercaptopurine; methotrexate; mitomycin; mitotane; mitoxantrone; paclitaxel; pemetrexed, pentostatin; plicamycin; procarbazine; rituximab; streptozocin; teniposide; thioguanine; thiotepa; verticillin A, vinblastine; vincristine; and vinorelbine.
32. A compound of paragraph 27 or a cross-linked gel of paragraph 28 used in water/sewage treatment, superabsorbent polymers, detergent, adhesives, dispersant, and cosmetics.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Synthesis of poly(1,2-glycerol carbonate)

The benzyl protected poly(1,2-glycerol carbonate) was synthesized via ring-opening copolymerization of benzyl glycidyl ether (BGE), 1, with $CO_2$ (220 psi) using the [SalcyCo$^{III}$X] complexes, 2a-2e, shown in FIG. 1. We first examined a series of catalysts with different axial ligands including nitrate, chloride, bromide, trichloroacetate, and 2,4-dinitrophenoxy (DNP) (Table 1). All of the resultant polymers contained >99% carbonate linkage, as determined by NMR and the selectivity for polycarbonate over cyclic carbonate ranged from 73% to 98% depending on the axial ligand. The selectivity was highest for DNP and lowest for bromide. When DNP serves as both axial ligand and cocatalyst anion, highest selectivity of >99% was achieved. All resultant polymers showed a head-to-tail selectivity of 92%. The catalyst activity, however, was significantly lower than that reported for the polymerization of propylene oxide (~150 h$^{-1}$ vs.~500 h$^{-1}$, respectively). This is likely a result of a more sterically hindered side chain. It is known that water not only acts as a chain transfer agent but also competitively binds to the Coreducing catalyst activity. We also suspect that trace water still present in the viscous benzyl glycidyl ether may contribute to the low activity. Increasing the temperature to 50° C. lead to moderately increased activity, but selectivity was still compromised. SEC analysis revealed molecular weights significant lower than theoretical values and bimodal but narrow PDIs (<1.07 for each and <1.15 combined). A plot of molecular weight versus conversion showed a linear increase of $M_n$ with conversion. These results are consistent with a living polymerization mechanism involving fast and reversible chain transfer with water acting as a chain transfer agent, as has been reported for the polymerization of propylene oxide.

TABLE 1

Axial ligand effect on the polymerization of rac-BGE with carbon dioxide using [(S,S)-SalcyCo$^{III}$X]/[PPN]Y.

| # | Catalyst | Turnover Freq. (h$^{-1}$) | Selectivity (% PBGC) | M$_n$ (kg/mol)[1] | PDI[1] |
|---|---|---|---|---|---|
| 1 | 2a | 123 | 96 | 32.3 | 1.13 |
| 2 | 2b | 142 | 94 | 34.4 | 1.12 |
| 3 | 2c | 146 | 73 | 19.7 | 1.15 |
| 4 | 2d | 160 | 96 | 25.5 | 1.09 |
| 5 | 2e | 140 | 98 | 41.3 | 1.10 |
| 6[2] | 2e | 150 | >99 | 33.6 | 1.13 |
| 7[3] | 2e | 200 | 87 | 27.3 | 1.12 |

The reactions were performed in neat rac-BGE (3.81 ml, 25 mmol) in a 45 ml autoclave under 220 psi CO$_2$ pressure with 1000:1:1 substrate/catalyst/cocatalyst loading at 22° C. for 4 h. All resultant poly(benzyl 1,2-glycerol carbonate)s (PBGC's) contain >99% carbonate linkage, determined by $^1$H spectroscopy.
[1]All resultant polymers exhibit bimodal distribution, the values are averaged over two peaks.
[2]The reaction was performed with cocatalyst PPNDNP.
[3]The reaction was performed at 50° C.

Figure 2:
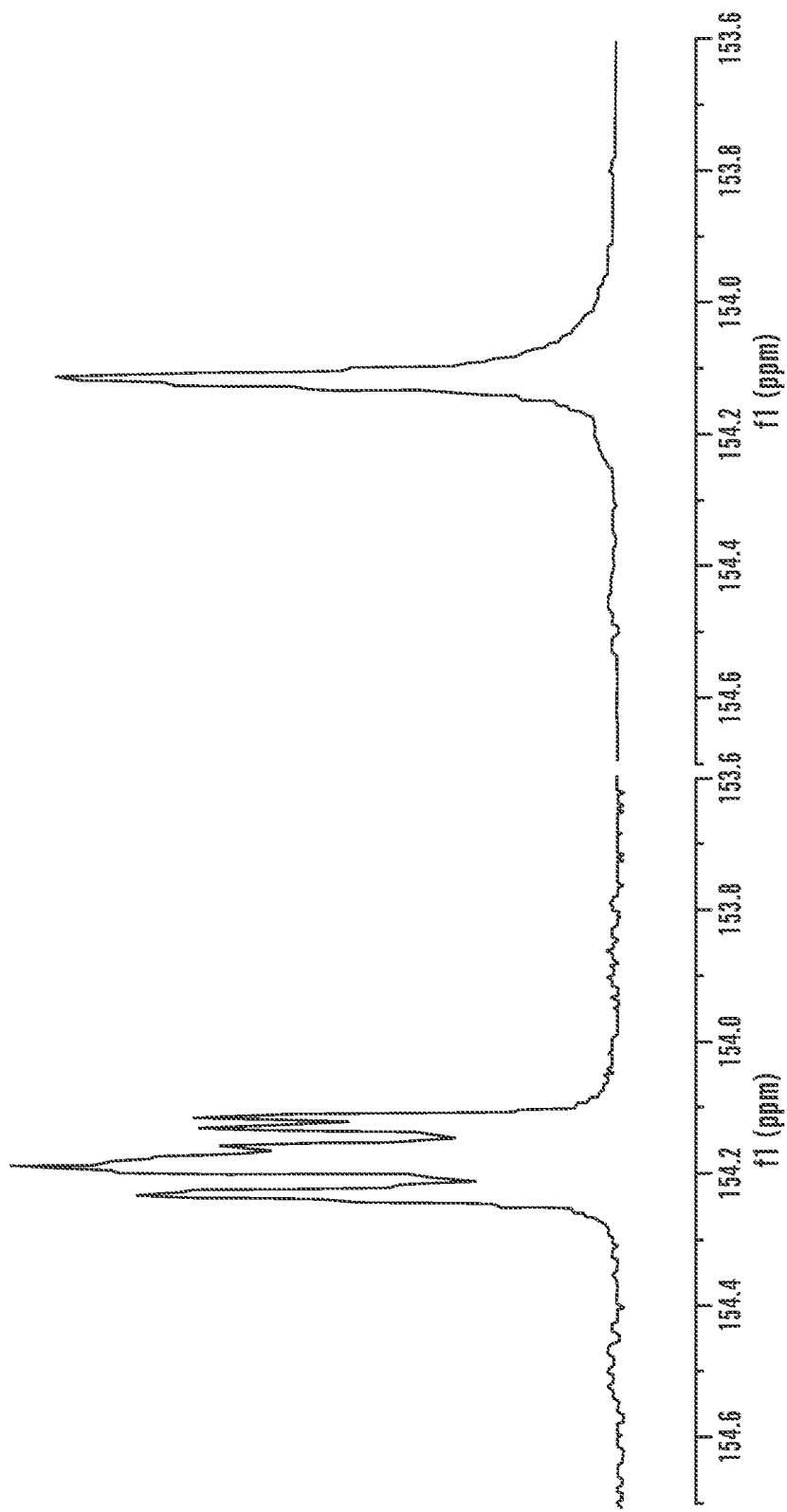
FIG. 2 shows the $^{13}$C NMR of carbonyl region of atactic (left) and isotactic (right) polymer.

However, as what is observed in copolymerization of propylene oxide with CO2, in our system, we also noticed that the cyclic carbonate product was being produced when the conversion reached ~70%. Based on the work by Lu who reported that a tethered 1,5,7-triabicyclo[4,4,0]-dec-5-ene coordinating [SalcyCo$^{III}$X] complex was a more thermally stable and robust catalyst (even under diluted solutions) for CO2/epoxide polymerizations,[41,42] we investigated this catalyst, 3, for the polymerization of monomer 1 (FIG. 1). Catalyst 3 was synthesized following a slightly modified literature procedure.[41] The polymers ranged in M$_n$ from 30,000 to 50,000 g/mol, contained >99% carbonate linkage with >97% polycarbonate selectivity, and possessed narrow PDIs (Table 2). Increasing the temperature or decreasing the catalyst loading afforded an increase in the catalyst turnover number with a greatest value, 620 h$^{-1}$, achieved at a temperature of 60° C. and a 10000:1 monomer to catalyst ratio, with slightly compromised polymer selectivity. Running the reaction in 1 ml toluene at 4000:1 catalyst loading (#6, Table 2) resulted in complete conversion (>97%) of the monomer. The poly(benzyl 1,2-glycerol carbonate)s polymers were soluble in DCM, THF, and toluene, but not in alcohols or water Given the encouraging result above, we next synthesized a chiral, isotactic, version of the polymer. A hydrolytic kinetic resolution of monomer 1 was performed with Jacobson's catalyst in greater than 98% yield to afford the R-enantiomer, following a published procedure.[43] Subsequent, polymerization of the R-enantiomer with CO2 using catalyst 3 afforded an isotactic polymer of 20.3 kg/mol with PDI of 1.11 (Scheme 1). The isotactic nature of the polymer is evident from the $^{13}$C NMR spectrum as shown in FIG. 2. The atactic polymer is characterized by the clearly-splited carbonyl triads peaks that are close in intensity, while the isotactic polymer exhibits one single sharp peak at 154.1 ppm. The $^{13}$C spectrum also shows a head-to-tail selectivity of 98%. When the polymer is dissolved in THF, it possesses a specific rotation of −15.2° at 27° C.

TABLE 2

Copolymerization of rac-BGE with CO$_2$ using catalyst 3.

| # | Catalyst loading | Temp (° C.) | Turnover Freq. (h$^{-1}$) | Selectivity (% PPC) | M$_n$ (kg/mol)/PDI[1] |
|---|---|---|---|---|---|
| 1 | 2000:1 | 20 | 148 | >99 | 34.9/1.10 |
| 2 | 2000:1 | 40 | 362 | >99 | 33.6/1.11 |
| 3 | 4000:1 | 40 | 328 | >99 | 48.1/1.13 |
| 4 | 10,000:1 | 40 | 288 | >99 | 38.1/1.09 |
| 5 | 10,000:1 | 60 | 620 | 97 | 32.2/1.14 |
| 6[2] | 4,000:1 | 40 | 235 | >99 | 37.3/1.15 |

The reactions were performed in neat rac-BGE (3.81 ml, 25 mmol) in a 45 ml autoclave under 220 psi CO$_2$ pressure to 50%-60% conversion. All resultant poly(benzyl 1,2-glycerol carbonate)s (PBGC's) contain >99% carbonate linkage, determined by $^1$H spectroscopy.
[1]All resultant polymers exhibit bimodal distribution, the values are averaged over two peaks.
[2]The reaction was performed in 1 ml toluene.

Scheme 1. Synthesis of isotactic poly(benzyl 1,2-glycerol carbonate).

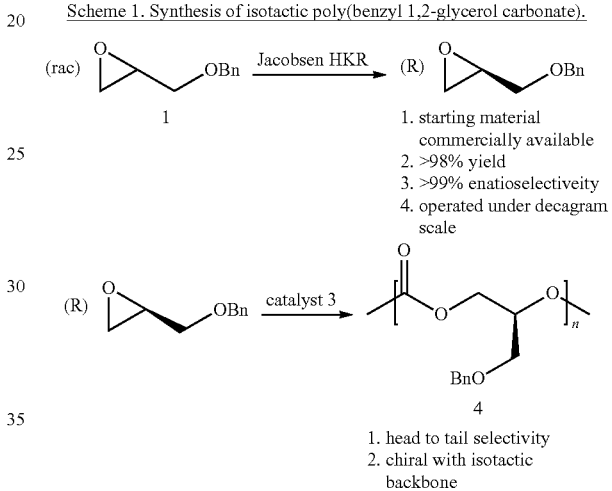

1. starting material commercially available
2. >98% yield
3. >99% enatioselectiveity
4. operated under decagram scale 1. head to tail selectivity
2. chiral with isotactic backbone Next, the benzyl-protecting group of the 1° OH of the polymer was removed using hydrogenation. Specifically, the polymer was dissolved in 7:3 ethyl acetate: methanol with Pd/C (20% catalyst loading based on Pd) and pressurized to 600 psi of H2 for 24 hours. After isolation of the polymer, NMR analysis revealed that the aromatic peaks located at 7.1-7.2 ppm were no longer present, confirming loss of the benzyl group from the polymer. The result from SEC analysis was consistent with the proposed structure (M$_n$=13.7 kg/mol; PDI 1.11). Hydrogenation reactions performed in THF, DCM and at low H2 pressure did not give the deprotected polymer. The poly(1,2-glycerol carbonate) is not soluble in common organic solvent (DCM), but is soluble in polar organic solvents such as DMF and DMSO.

Figure 3:
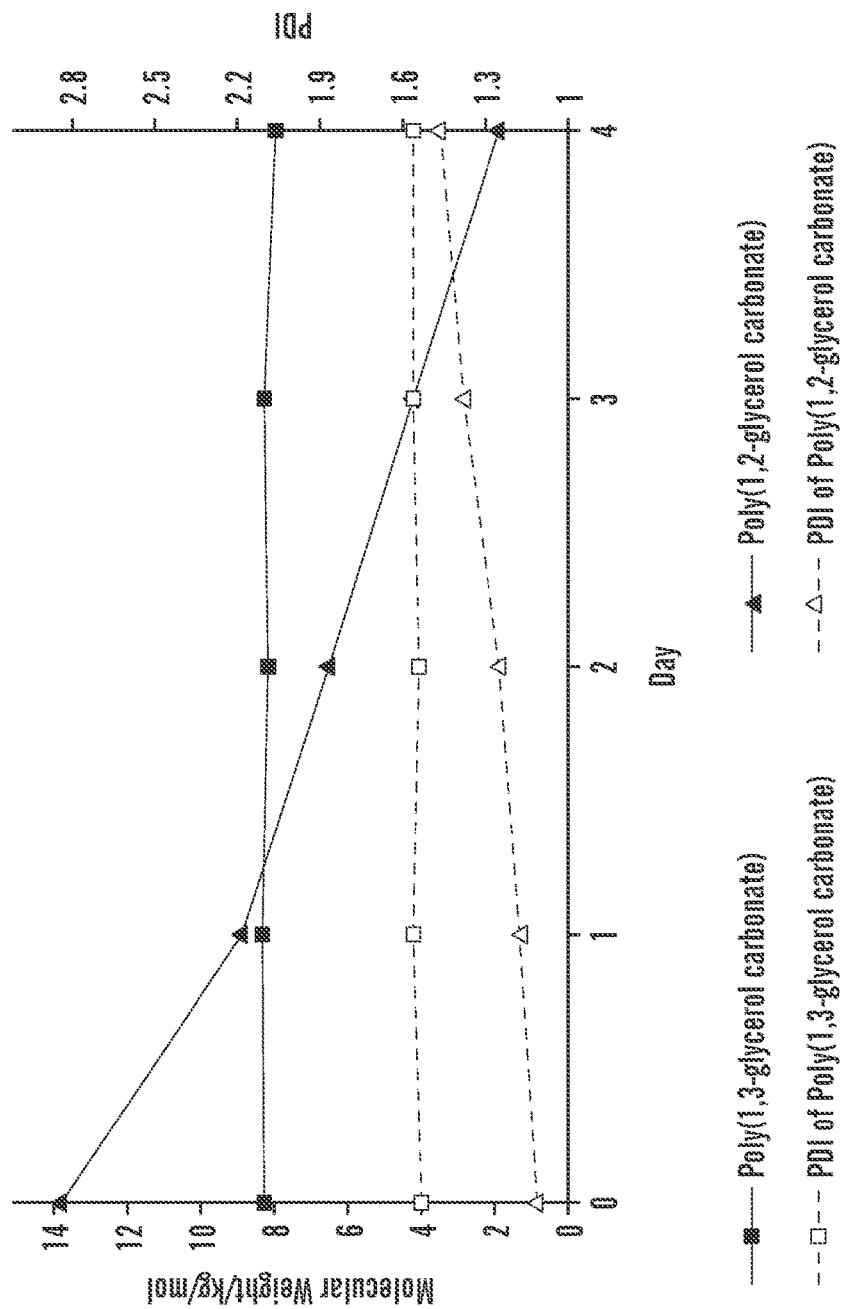
FIG. 3 shows degradation of poly(1,2-glycerol carbonate) compare to poly (1,3-glycerol carbonate in DMF at 37° C.

Finally, the rate of poly(1,2-glycerol carbonate) degradation in DMF (with 0.05 M LiBr for SEC purpose) at 37° C. was monitored by SEC and compared to that of a poly(1,3-glycerol carbonate). As shown in FIG. 3, poly(1,2-glycerol carbonate) degrades significantly faster than Poly(1,3-glycerol carbonate) with a t$_{1/2}$ of ~2 days. We attribute this increase in degradation to intramolecular attack of the pendant primary hydroxyl of poly(1,2-glycerol carbonate) to the carbonate linkage with formation of the thermodynamically stable 5-membered cyclic glycerol carbonate.

Figure 4:
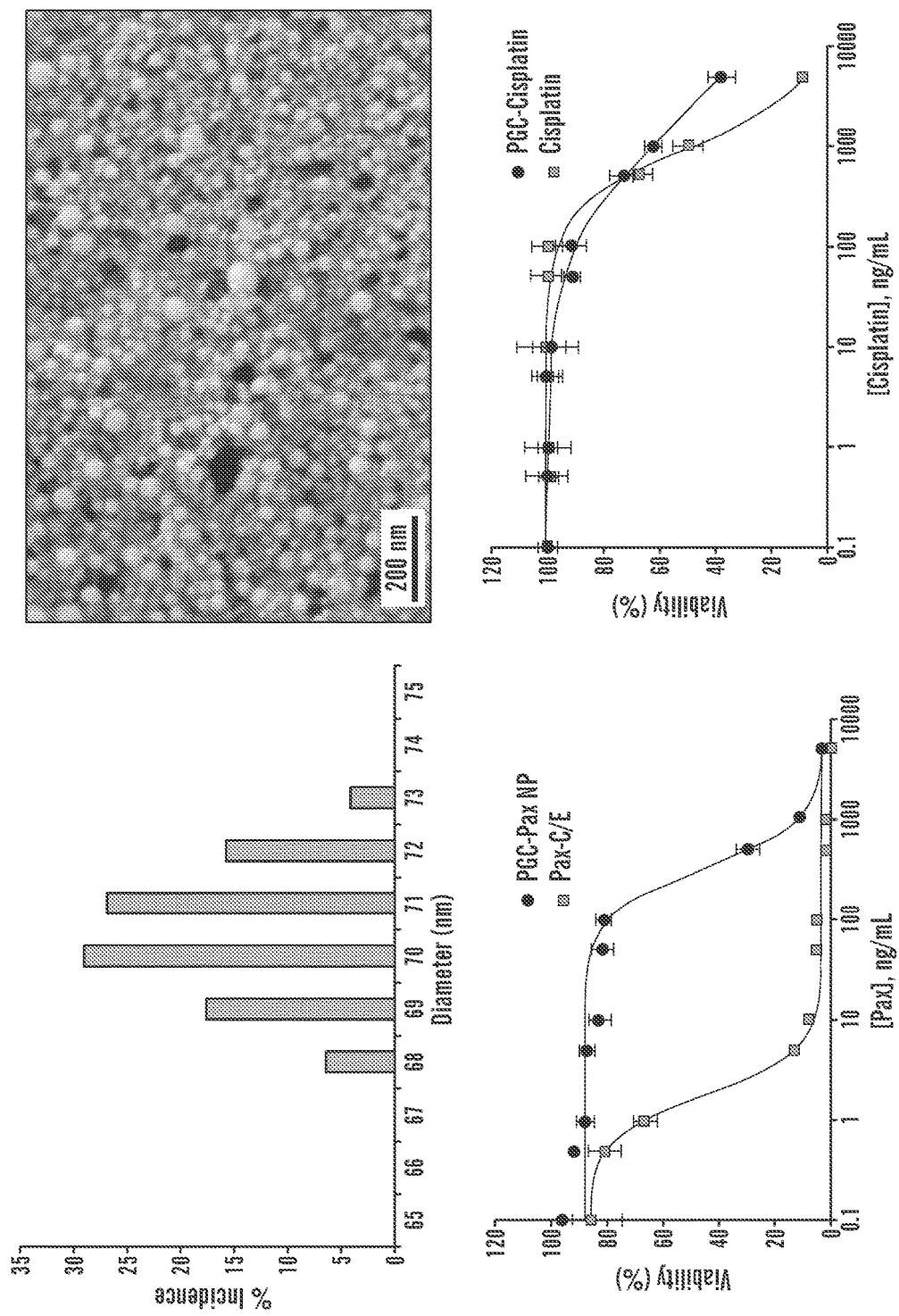
FIG. 4 Left upper panel: Dynamic light scattering analysis of PGC-Pax NPs. Average diameter=70.64 nm, PDI=0.093 nm; Right upper panel: SEM micrograph of PGC-Pax NPs. Scale bar=200 nm. Left lower panel: In vitro toxicity analysis of PGC-Pax NPs and Pax-C/E in MDA-MB-231 cells. Cells were incubated with treatment for 5 days, and viability was assessed. $IC_{50}$ of PGC-Pax NPs and Pax-C/E were 321.6 ng/mL and 1.9 ng/mL, respectively. Right lower panel: In vitro toxicity analysis of PGC-Cisplatin and cisplatin alone in A549 cells. Cells were incubated with treatment for 3 days, and viability was assessed. $IC_{50}$ of PGC-Cisplatin and cisplatin were 1530 ng/mL and 927.3 ng/mL, respectively.

Cytotoxicity Profile of poly(1,2-glycerol carbonate)-graft-succinic acid-Paclitaxel PGC-Pax and PGC-Cisplatin nanoparticles are synthesized using a miniemulsion technique. Briefly, the polymer is added to dichloromethane, and the organic phase is dispersed via sonication into an aqueous phase, containing sodium dodecyl sulfate as a surfactant. Nanoparticles are approximately 70 nm in diameter (PDI of 0.093), and they exhibit dose dependent toxicity against a breast cancer cell line, MDA-MB-231 (PGC-Pax), as well as a lung cancer cell line, A549 (PGC-Cisplatin). (FIG. 4)

Synthesis of alkyl-functionalized poly(1,2-glycerol carbonate)s.

The poly(1,2-butyl glycerol carbonate)s was synthesized via ring-opening copolymerization of butyl glycidyl ether with $CO_2$ (220 psi) using the bifunctional rac-[SalcyCo$^{II}$-$t$DNP] catalyst with DNP (2,4-dinitrophenoxy) as an axial ligand and quaternary ammonium salt on the ligand framework (Table 3). This catalyst has been reported to be stable and active under elevated temperatures and diluted conditions. During the optimization studies, we obtained polymers with low polydispersities (PDIs) in the range of 1.1-1.3 and molecular weights in the range of 18400-36300 g/mol containing >99% carbonate linkage with >90% selectivity. At monomer-to-catalyst ratio of 2000:1, increasing the temperature from 25 to 60° C. resulted in an increase in catalyst activity (Turnover Frequency, TOF) from 65 to 199 h$^{-1}$, with slightly compromised selectivity of 91% (Table 3, entry 3). To decrease the viscosity of the reaction mixture, the reaction was run in 1 mL of toluene at a 2000:1 catalyst loading and resulted in a decrease in TOF from 123 to 48 h-1 (Table 3, entries 2 and 4). Contrary to our expectations, decreasing catalyst loading to 4000:1 resulted in decrease in catalyst activity as compared to the exact conditions with a higher catalyst concentration (Table 3, entries 5 and 2). At catalyst loading of 10000:1, no reaction took place (Table 3, entry 6).

Subsequently, we carried out copolymerizations at higher $CO_2$ pressures of 440 psi. As expected, there was no substantial change in polymer formation as the catalyst activity increased from 123 to 150 h$^{-1}$ with a slight drop of selectivity from 99 to 97% (Table 3, entries 2 and 7). Running the reaction for a prolonged time resulted in nearly complete conversion of the monomer (>93%) with TOF of 67 h$^{-1}$ and high selectivity of 96% (Table 3, entry 8).

The catalyst, along with cyclic carbonate side product, can be efficiently removed from the synthesized polymer solution after copolymerization by precipitation in cold methanol and centrifugation (three cycles total). After purification, the cyclic carbonate side product was not observed in either $^1$H NMR or IR spectra.

Synthesis of poly(1,2-glyceric acid carbonate)

Monomer 4, binary catalyst 1 and bifunctional catalysts 2 and 3 were synthesized. Based on our previous results about axial ligand effect on polymer/cyclic carbonate selectivity, 2,4-dinitrophenolate (DNP) was used as both the axial ligand and the counter anion in all catalysts. Benzyl glycidate (BG) 4 was synthesized via an efficient two-step esterification-oxidation route in high overall yield (~85%). The benzyl protected poly(glyceric acid carbonate) was synthesized via ring-opening copolymerization of BG with $CO_2$ (220 psi) using both binary and bifunctional [SalcyCo$^{III}$X] complexes, 1-3, as shown in Scheme 2B. Under standard screening condition (neat epoxide, 500:1 catalyst loading, 25° C. and 220 psi $CO_2$ pressure), binary catalyst 1 failed to exhibit any catalytic activity in the copolymerization and surprisingly, bifunctional catalyst 2, which was highly active towards a range of substrates including epoxide bearing electron-withdrawing group, were also inactive. To our delight, bifunctional catalyst 3 bearing quaternary ammonium salt on the ligand framework turned out to be the catalyst that catalyzed the copolymerization.

Scheme 2. (A) Attempts to synthesize poly(glyceric acid carbonate) by oxidation of poly(1,2-glycerol carbonate). (B) Copolymerization of benzyl glycidate with $CO_2$ using binary and bifunctional [SalcyCo$^{III}$X] catalysts.

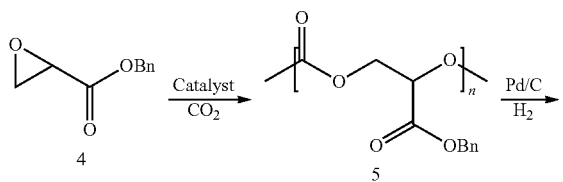

TABLE 3

Optimization of Reaction Parameters for Copolymerization of CO2 and Butyl Glycidyl Ether

| Entry | Catalyst Loading | Temp (° C.) | TOF (h$^{-1}$) | Selectivity (%) | $T_g$ (° C.) | $T_{decomp}$$^a$ 5/50 (° C.) | $M_n$$^b$ (kg/mol) | PDI ($M_w/M_n$) |
|---|---|---|---|---|---|---|---|---|
| 1 | 2000:1 | 25 | 65 | 99 | −22 | 222/253 | 19.3 | 1.3 |
| 2 | 2000:1 | 40 | 119 | 98 | −24 | 219/269 | 20.9 | 1.3 |
| 3 | 2000:1 | 60 | 183 | 91 | −25 | 210/261 | 23.8 | 1.2 |
| 4$^c$ | 2000:1 | 40 | 57 | 98 | ND | ND | ND | ND |
| 5 | 4000:1 | 40 | 105 | 99 | −22 | 215/259 | 19.3 | 1.1 |
| 6 | 10000:1 | 40 | ND | ND | ND | ND | ND | ND |
| 7$^d$ | 2000:1 | 40 | 150 | 97 | −23 | 216/272 | ND | ND |
| 8$^e$ | 2000:1 | 40 | 70 | 95 | −38 | 217/273 | 29.3 | 1.2 |

All reactions were performed in neat butyl glycidyl ether in a 15 mL autoclave under 220 psi of CO2 pressure to 40-60% conversion (2-3 runs).
ND = Not Determined.
$^a$The temperature at 5 and 50% weight loss, respectively, on the TGA curve of the copolymers.
$^b$Determined by GPC analysis using polystyrene as standards. All resultant polycarbonates showed bimodal distribution.
$^c$Reaction was run in 1 mL of toluene.
$^d$Reaction was run under 440 psi of CO2 pressure.
$^e$Reaction was run to >93% conversion.

-continued

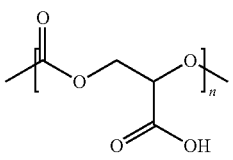

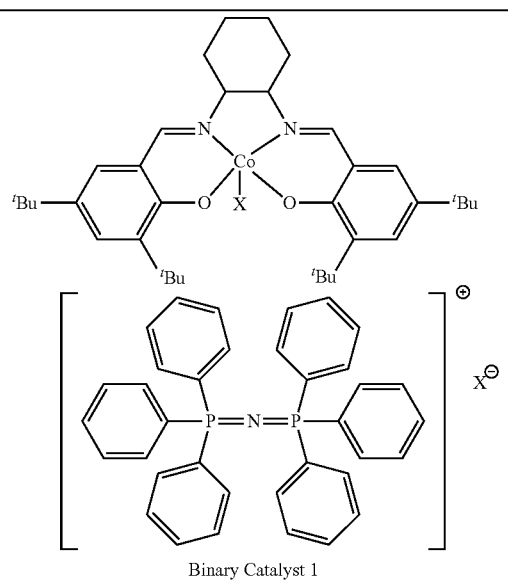

Binary Catalyst 1

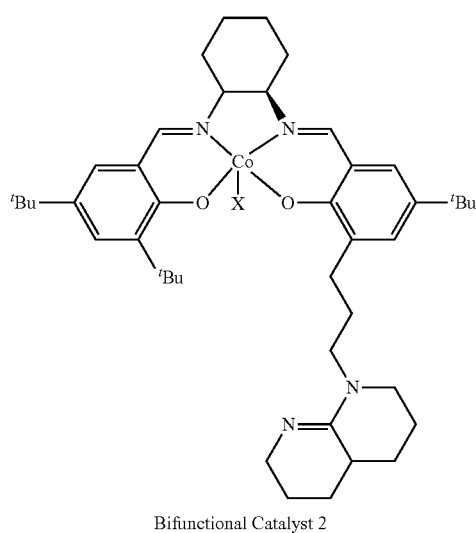

Bifunctional Catalyst 2

-continued

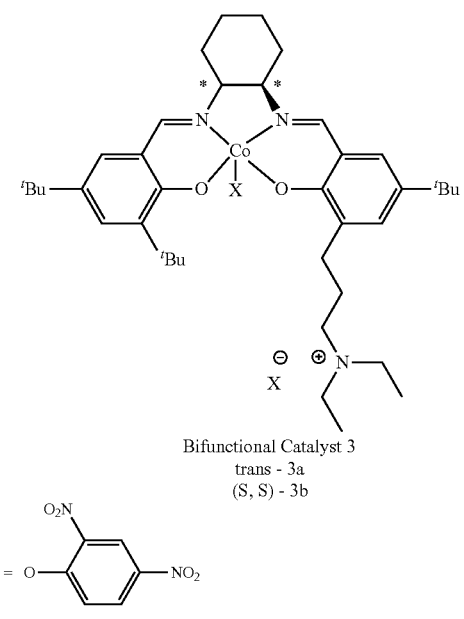

Bifunctional Catalyst 3
trans - 3a
(S, S) - 3b

As shown in Table 4, catalyst 3 effectively catalyzed the copolymerization of BG with CO2 with excellent carbonate linkage selectivity (>99%) and high polymer/cyclic carbonate selectivity (>90%) to give high molecular weight polymers with narrow molecular weight distribution. All resultant polymers are of high regioregularity and showed a head-to-tail connectivity of 91%. The catalyst activity, however, was significantly lower than that reported for the polymerization of benzyl glycidyl ether (~15 $h^{-1}$ vs.~150 $h^{-1}$, respectively). This is likely a result of the electron withdrawing effect of the carbonyl group and the resultant much-lowered HOMO (highest occupied molecular orbital) of the epoxide. Decreasing the catalyst loading from 500:1 to 1000:1 resulted in slight decrease in activity and polymer selectivity and significant increase in molecular weight (MW). Increase the temperature to 40° C. causes a significant decrease in polymer selectivity (Table 4, entry 5). Performing the reaction in toluene resulted in >90% monomer conversion with compromised activity (8 $h^{-1}$) and polymer selectivity (80%) while MW almost remained the same, presumably due to both decreased polymer selectivity and trace amount of water introduced by toluene.

TABLE 4

Synthesis of Poly(benzyl glycidate carbonate) Using [SalcyCoIIIX] Complexes 1-3

| # | Catalyst | Catalyst loading | Turnover Freq. ($h^{-1}$) | Selectivity (% polymer) | $M_n$ (kg/ml)/ PDI |
|---|---|---|---|---|---|
| 1 | 1 | 500:1 | — | — | — |
| 2 | 2 | 500:1 | — | — | — |
| 3 | 3a | 500:1 | 12 | 90 | 18.2/1.18 |
| 4 | 3a | 1000:1 | 11 | 89 | 25.4/1.19 |
| 5[1] | 3a | 1000:1 | 24 | 77 | 18.1/1.21 |
| 6[2] | 3a | 1000:1 | 8 | 86 | 27.2/1.22 |
| 7[3] | 3a | 1000:1 | 13 | 92 | 24.2/1.19 |

TABLE 4-continued

Synthesis of Poly(benzyl glycidate carbonate)
Using [SalcyCoIIIX] Complexes 1-3

| # | Catalyst | Catalyst loading | Turnover Freq. (h$^{-1}$) | Selectivity (% polymer) | M$_n$ (kg/ml)/ PDI |
|---|---|---|---|---|---|
| 8 | 3b | 1000:1 | 15 | 93 | 30.5/1.14 |
| 10 | 3a | 2000:1 | 10 | 90 | 32.2/1.15 |

The reactions were performed in neat rac-BG (1.42 ml, 10 mmol) in an 8 ml autoclave under 220 psi CO2 pressure to ~65% conversion unless otherwise noted. All resultant poly(benzyl glycidate carbonate)s (PBGC's) contain >99% carbonate linkage, as determined by $^1$H spectroscopy.
$^1$The reaction was performed at 40° C.,
$^2$The reaction was performed in 0.4 ml toluene,
$^3$The reaction was performed under 440 psi.

Size exclusion chromatography analysis revealed molecular weights significant lower than theoretical values and monomodal distribution with narrow PDIs (<1.20). This is in sharp contrast to most of the previously reported systems where bimodal distributions were observed due to trace amount of water acting as chain transfer agent, leading to two populations of polymers with different molecular weights.

Figure 5A:
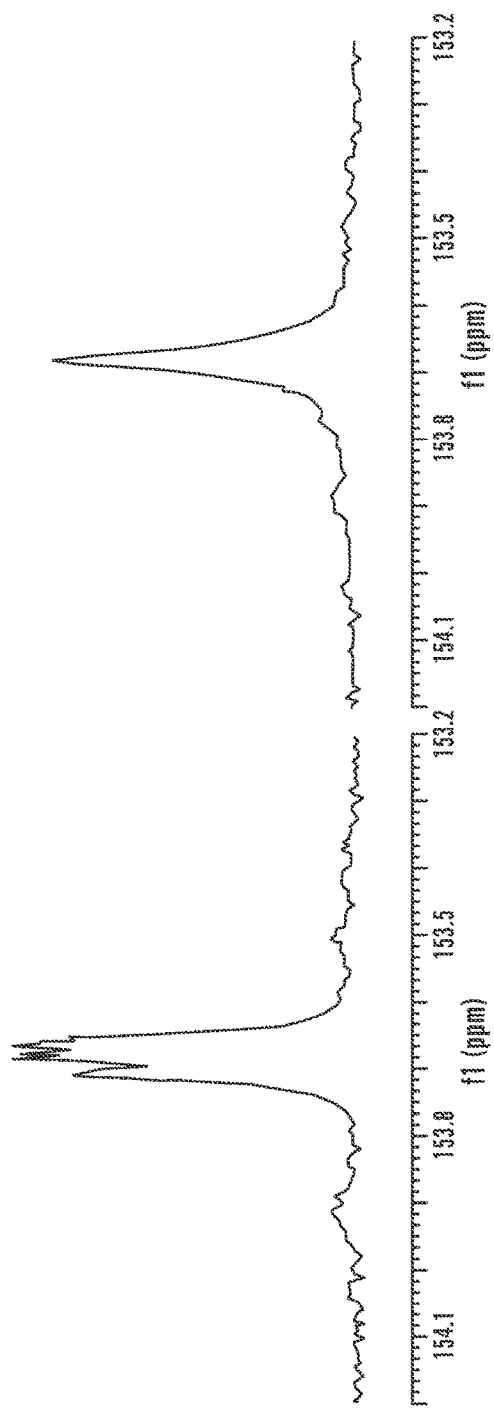
FIG. 5A shows the $^{13}$C NMR of carbonyl region of atactic (left) and isotactic (right) poly(benzyl glycidate carbonate).
Figure 5B:
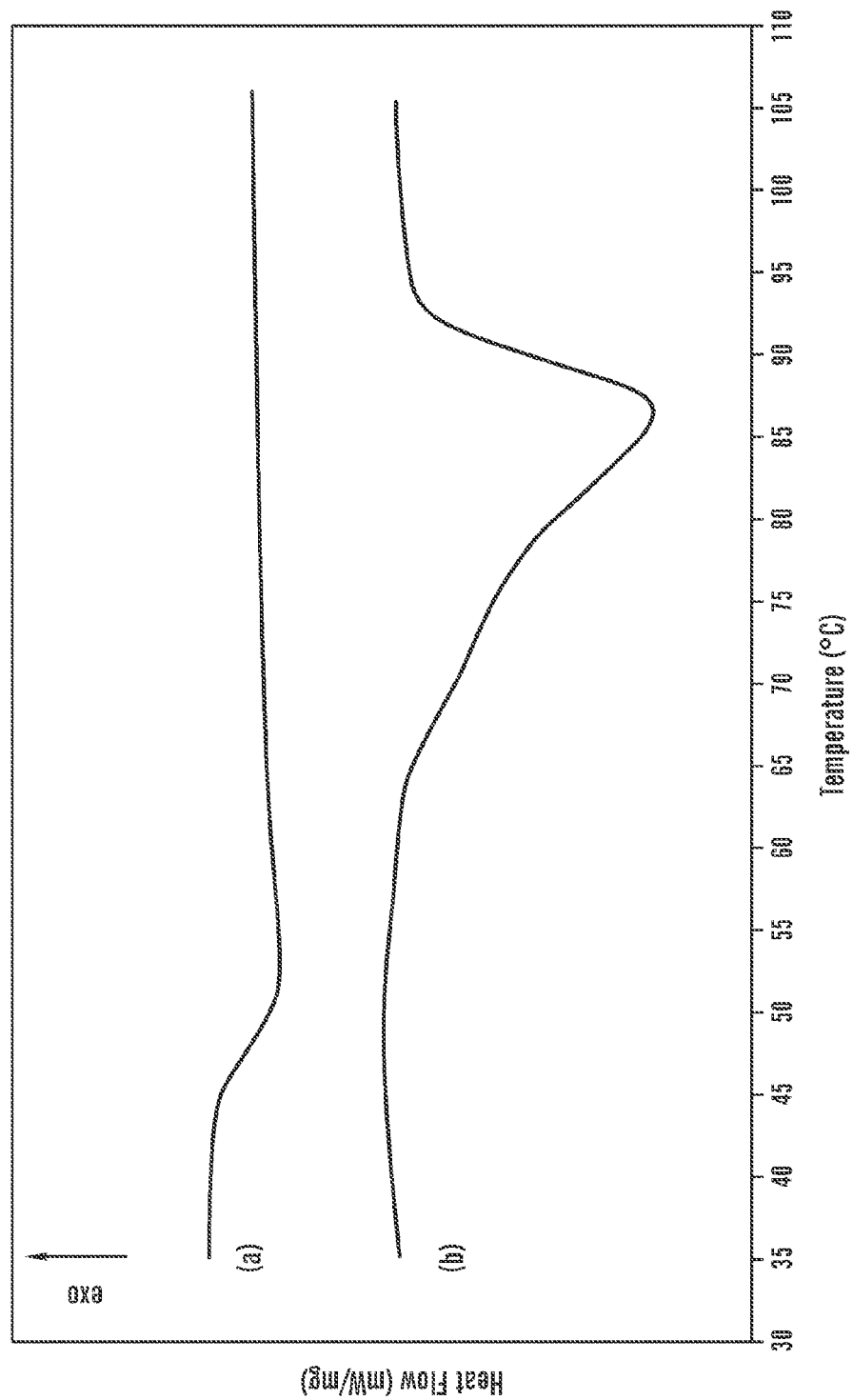
FIG. 5B shows the differential scanning calorimetry (DSC) trace of (a) atactic (b) isotactic poly(benzyl glycidate carbonate).

Given the encouraging results above, we set out to synthesize an isotactic version of poly(benzyl glycidate carbonate). Surprisingly, the hydrolytic kinetics resolution (HKR) of BG has never been accomplished before. In our hand, HKR of racemic BG using (R,R)-SalcyCo$^{III}$OTs provided (R)-benzyl glycidate in >90% yield with >98% enantiomeric excess (data not shown). Copolymerization of (R)-BG with CO2 using chiral catalyst 3b afforded a polymer with isotactic backbone (FIG. 5A). Interestingly, contrary to poly(1,2-benzyl glycerol carbonate), which is an amorphous material (T$_g$ (glass transition temperature)=8° C.) when it is both atactic or isotactic, isotactic poly(benzyl glycidate carbonate) turned out to be a semicrystalline polymer with a T$_m$ (melting temperature)=87° C. (FIG. 5B).

Figure 6A:
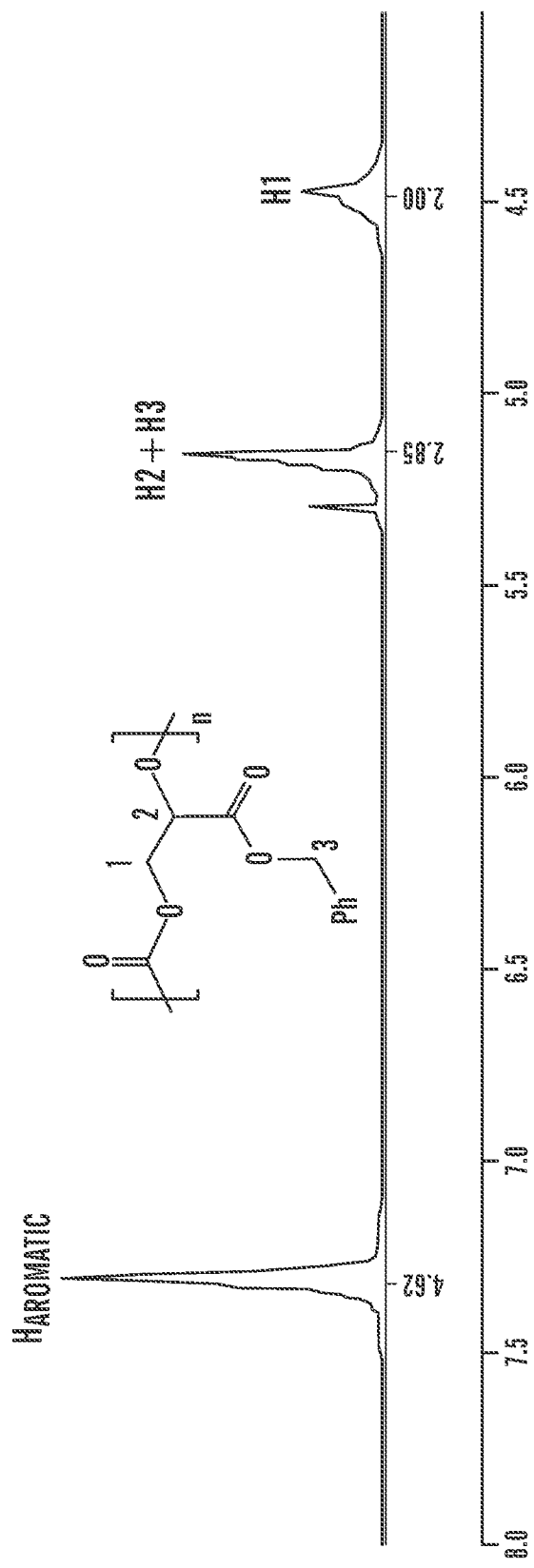
FIG. 6A shows the $^1$H NMR of PBGAC in $CDCl_3$.
Figure 6B:
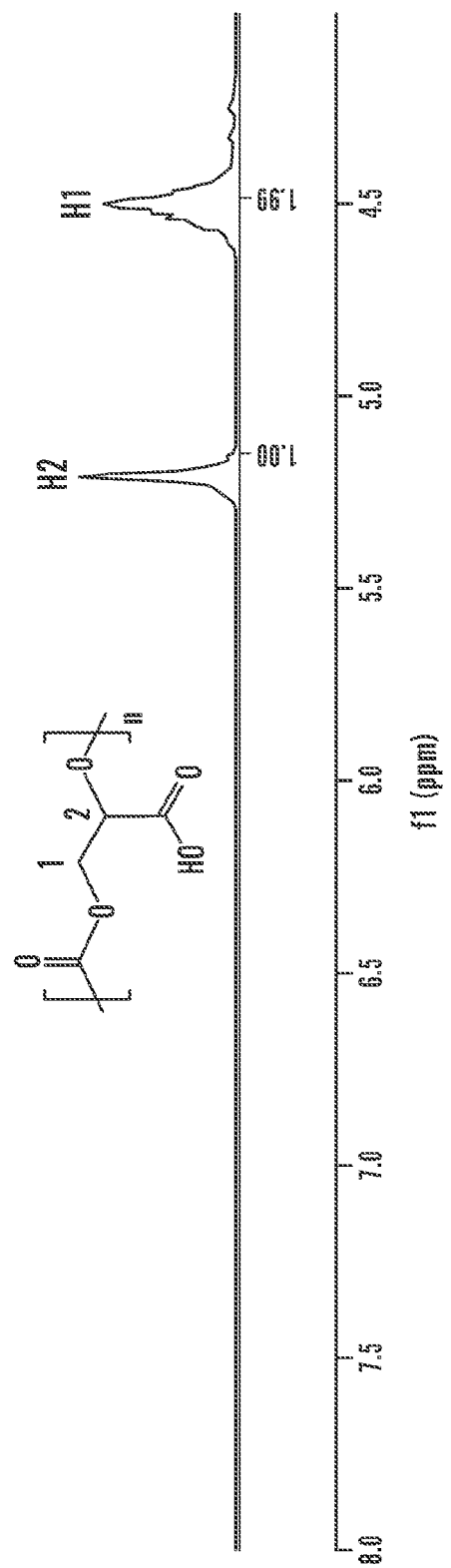
FIG. 6B shows the $^1$H NMR of PGAC in DMSO-$d_6$ after hydrogenolysis.

Benzyl protecting group was removed by hydrogenolysis to provide poly(glyceric acid carbonate) (PGAC). Specifically, PBGAC (MW=25.4 kg/mol, PDI 1.19, Table 4, entry 4) was dissolved in ethyl acetate:methanol=3:1 with Pd/C (20 wt % loading) and pressurized to 400 psi of H2 for 8 h. After isolation of the polymer, $^1$H NMR analysis revealed the aromatic peaks located at 7.1-7.2 ppm were no long present, confirming the loss benzyl group (FIG. 6). The result from SEC was consistent with the proposed structure without backbone scission. PGAC was isolated as a white polymer. It is soluble in polar aprotic or protic solvent such as dimethylformide, dimethylsulfoxide, water, and methanol, while not soluble in relatively non-polar solvent such as tetrahydrofuran, dichloromethane, etc.

Figure 7:
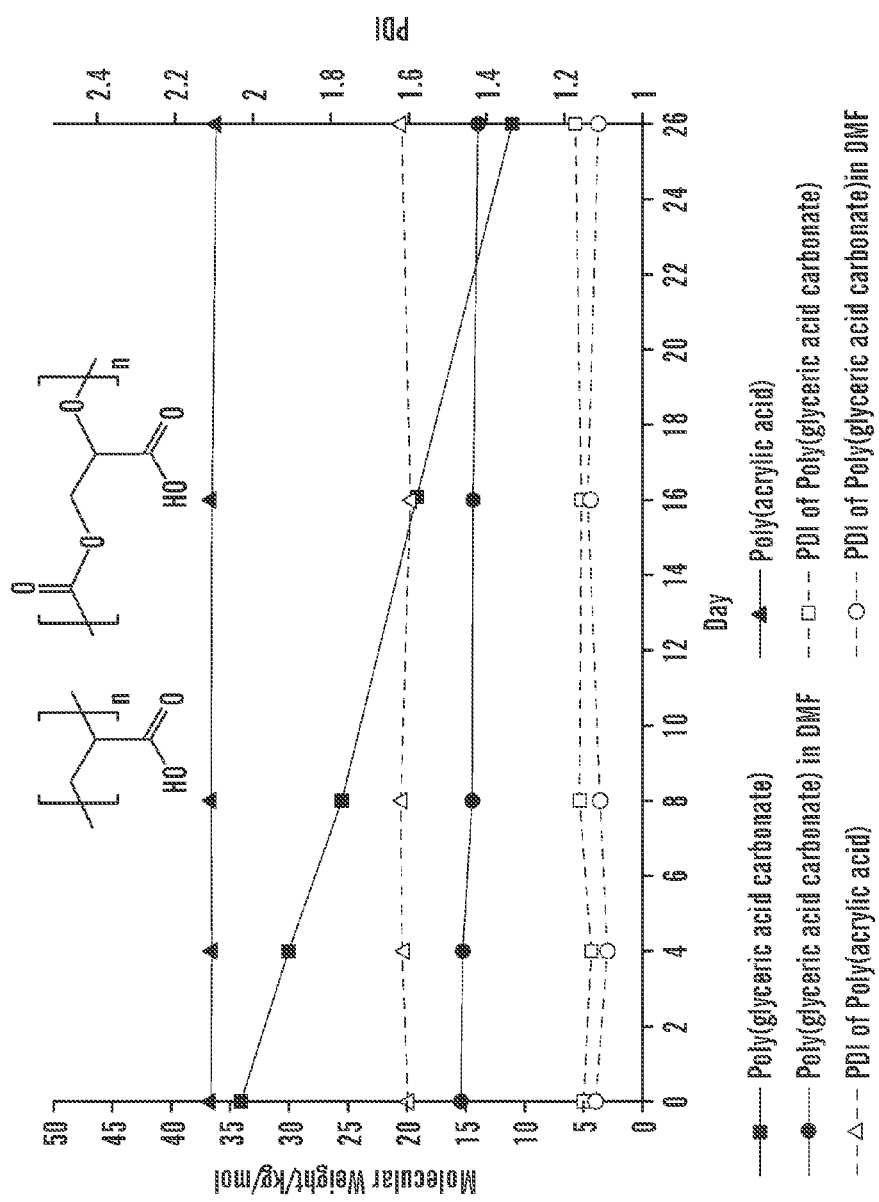
FIG. 7 shows degradation behavior of poly(glyceric acid carbonate)s in water and DMF.

The rate of PGAC degradation in deionized water was monitored by SEC and compared to that of a poly(acrylic acid) with the same molecular weight (FIG. 7). In water, PGAC showed significant degradation over a 26-day period with a t$_{1/2}$~12 days, while as expected, no degradation occurred for poly(acrylic acid). It is proposed that the accelerated degradation for poly(1,2-glycerol carbonate)s is attributed to the intramolecular attack of the primary hydroxyl group onto the polycarbonate backbone, leading to the formation of thermally stable five-membered cyclic carbonate. In order to determine if this mechanism is partially responsible for PGAC degradation in water along with acidic hydrolytic degradation mechanism, we performed the degradation in anhydrous DMF, which eliminates the hydrolysis mechanism. Interestingly, PGAC showed negligible degradation over a 26-day period, indicating that acidic hydrolytic degradation is likely the only contributor for the degradation of PGAC in water. This is presumably a result of the much-lowered nucleophilicity and relatively higher rigidity of the carboxylic acid group in PGAC comparing to the primary hydroxyl group in poly(1,2-glycerol carbonate). The stability of PGAC was also evidenced by the fact that the dry state PGAC remains stable over a few months period at room temperature on bench top, as monitored by SEC. This is in contrast to poly(1,2-glycerol carbonate) which even degrades in dry state at room temperature.

Example 2

Synthesis and Characterization of poly(1,2-glycerol Carbonate)

Figure 8A:
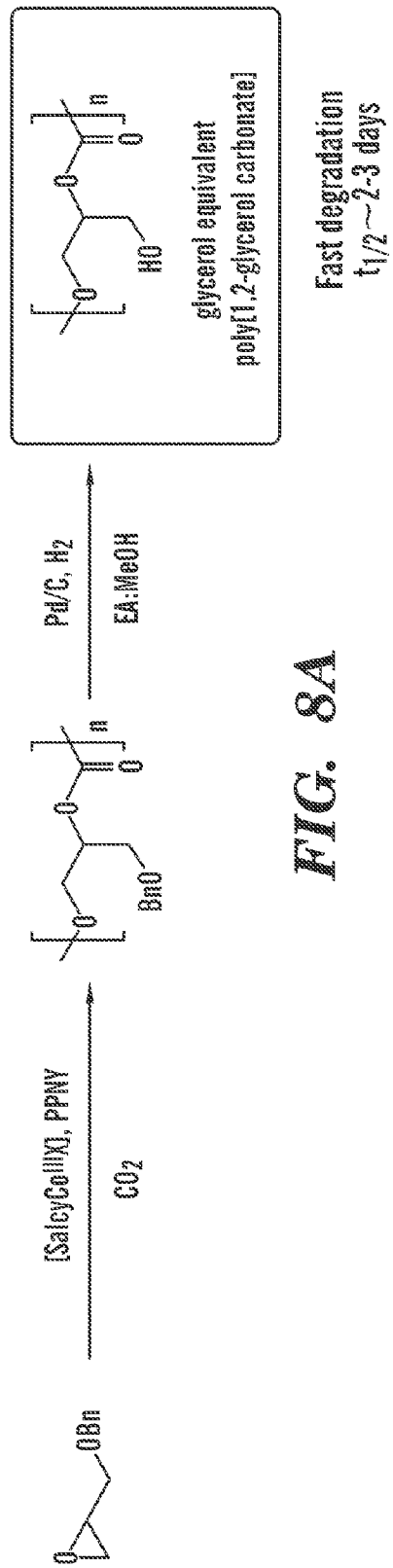
FIG. 8A is a schematic representation of synthesis of poly(1,2-glycerol carbonate).

Poly(1,2-glycerol carbonate) (PGC) is synthesized by the copolymerization of epoxide with CO2 as schematically shown in FIG. 8A. Specifically, benzyl glycidyl ether is copolymerized with CO2 to afford poly(benzyl 1,2-glycerol carbonate). The benzyl group is then removed by hydrogenolysis to give poly(1,2-glycerol carbonate) with a functionalizable hydroxyl group on each repeating unit. This polymer can be synthesized in a range of MWs; as an example, for a MW of 10 kDa, we obtain a PDI of approximately 1.1. PGC shows remarkably accelerated degradation, with a half-life of 2-3 days in dimethylformamide. The hypothesized mechanism of breakdown is the intramolecular cyclization of the primary hydroxyl group onto the carbonate backbone, leading to the thermodynamically stable 5-membered cyclic glycerol carbonate.

PGC-Pax Synthesis and Characterization

Figure 8B:
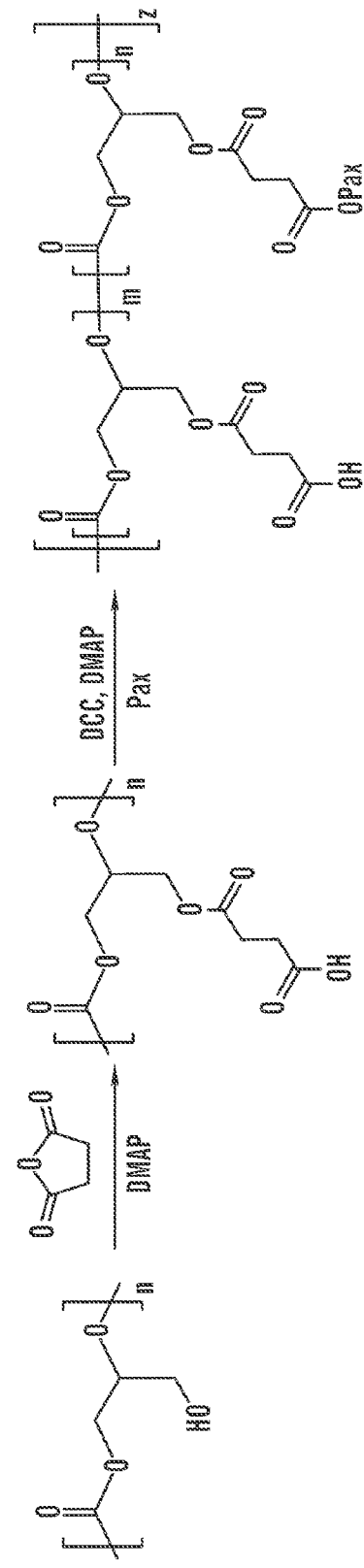
FIG. 8B is a schematic representation of synthesis of poly(1,2-glycerol carbonate)-graft-succinic acid-paclitaxel conjugate.
Figure 9:
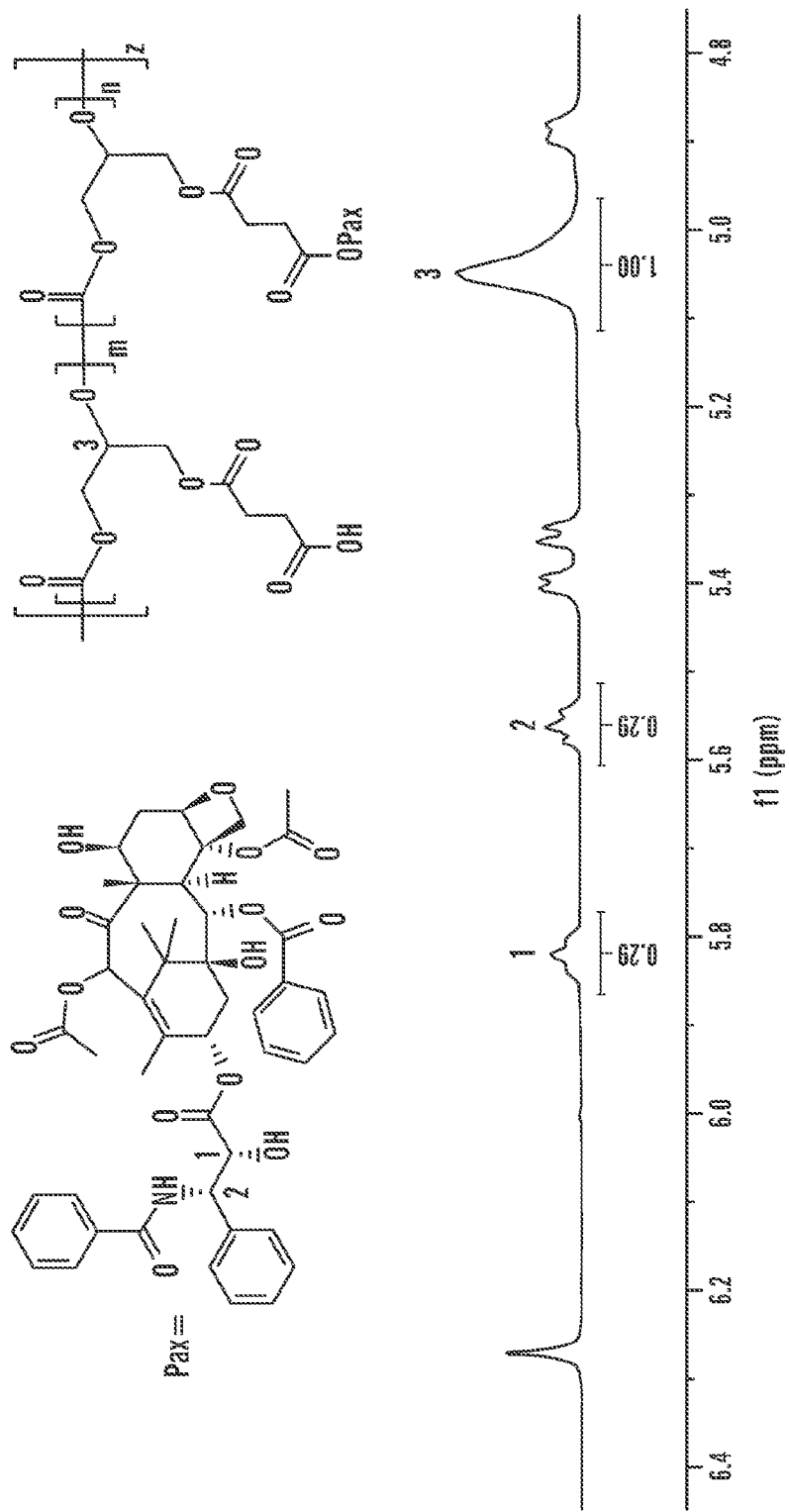
FIG. 9 shows $^1$H NMR of poly(1,2-glycerol carbonate)-graft-succinic acid-paclitaxel conjugate with 29 mol % Pax incorporation. Pax incorporation can be quantified in molar ratio by comparing the peaks of protons on Pax to a peak on the polymer backbone.

PGC-Pax is synthesized by treating PGC with succinic anhydride and DMAP to give PGC-graft-succinic acid (FIG. 8B). Standard coupling chemistry using DCC and DMAP with Pax then affords us PGC-Pax with high Pax loadings of up to 70 wt %. For a 57 wt % Pax loaded polymer, the MW is 5 kDa, with a PDI of 1.1. The incorporation of Pax in molar ratio can be quantified via proton NMR by comparing the peaks of protons on Pax to one of the peaks on the polymer backbone (FIG. 9).

Formulation and Characterization of PGC-Pax and PGC-Bn NPs

SDS-coated 34, 37, 39, and 43 mol % Pax-loaded PGC-Pax NPs, and PGC-Bn NPs have been synthesized using the miniemulsion procedure previously described. 25-50 mg of polymer is dissolved into 0.5 mL of DCM, and SDS (at a 1:5 SDS:polymer ratio) is dissolved into 2 mL of 10 mM pH 7.4 phosphate buffer. The aqueous phase is then added to the oil phase, and the solution is emulsified under an argon blanket via ultrasonication. The emulsion is then subjected to stirring under air overnight to allow for the evaporation of remaining solvent. The NP solution is finally dialyzed for 2 hours against 1 L of 5 mM pH 7.4 phosphate buffer to allow for the removal of excess salts and surfactants.

Figure 10A:
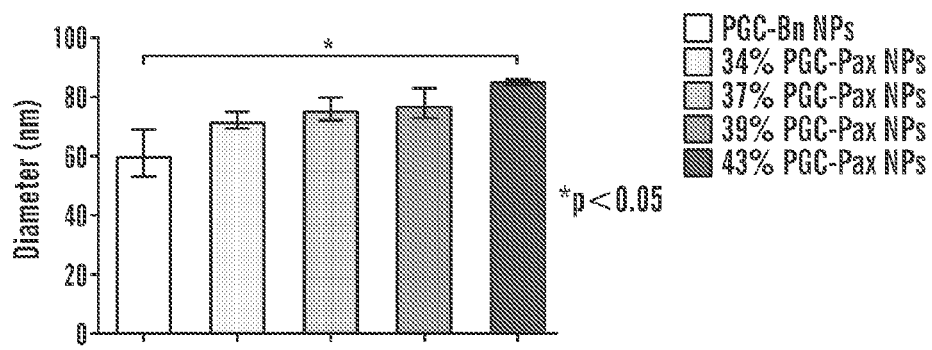
FIG. 10A-10C show DLS size (FIG. 10A), PDI (FIG. 10B) and zeta potential (FIG. 10C) analysis of PGC-Bn NPs and PGC-Pax NPs with varying Pax loadings in mol %.
Figure 10B:
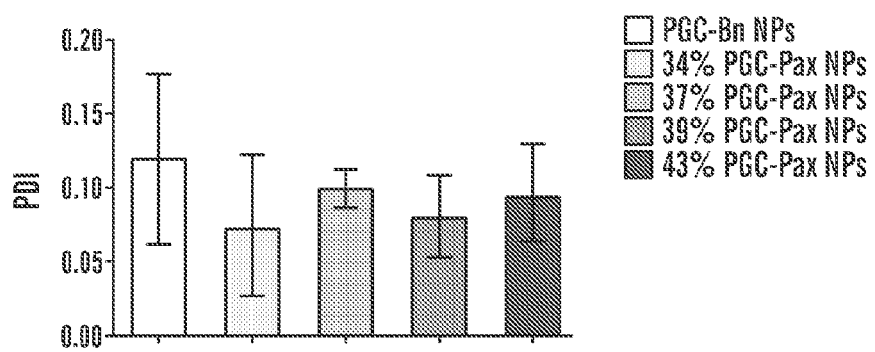
Figure 10C:
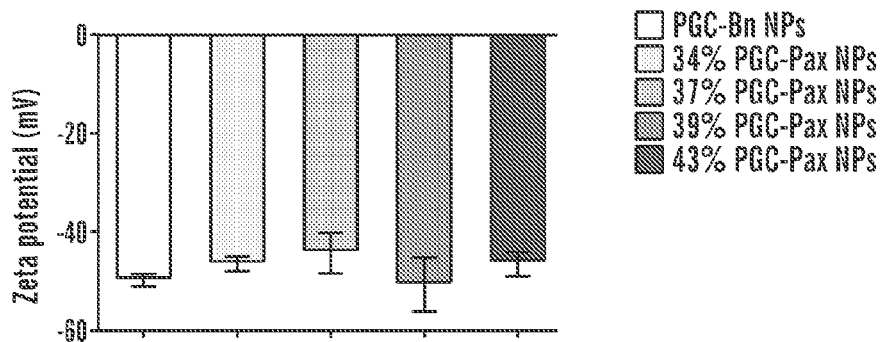
Figure 11C:
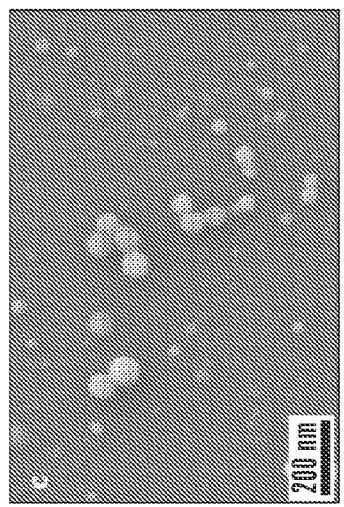
FIGS. 11A-11E are SEM micrographs of PGC-Bn NPs (FIG. 11A), 34% PGC-Pax NPs (FIG. 11B), 37% PGC-Pax NPs (FIG. 11C), 39% PGC-Pax NPs (FIG. 11D), and 43% PGC-Pax NPs (FIG. 11E).
Figure 11B:
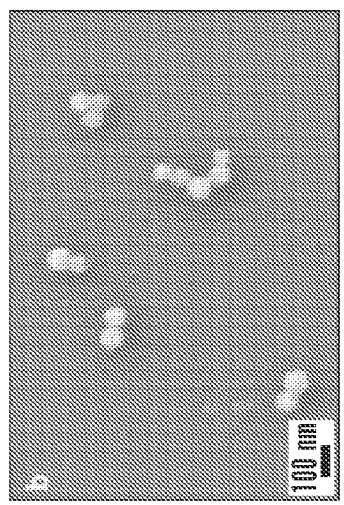
Figure 11A:
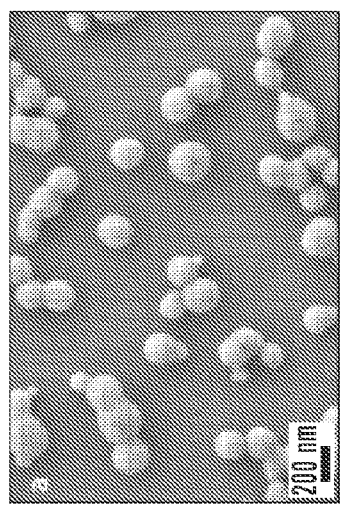
Figure 11E:
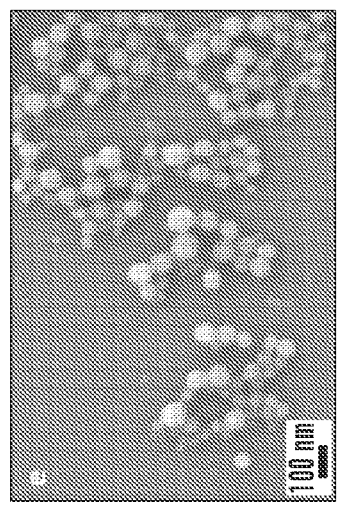
Figure 11D:
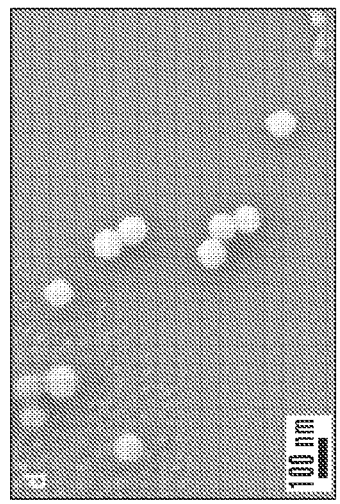
Figure 12A:
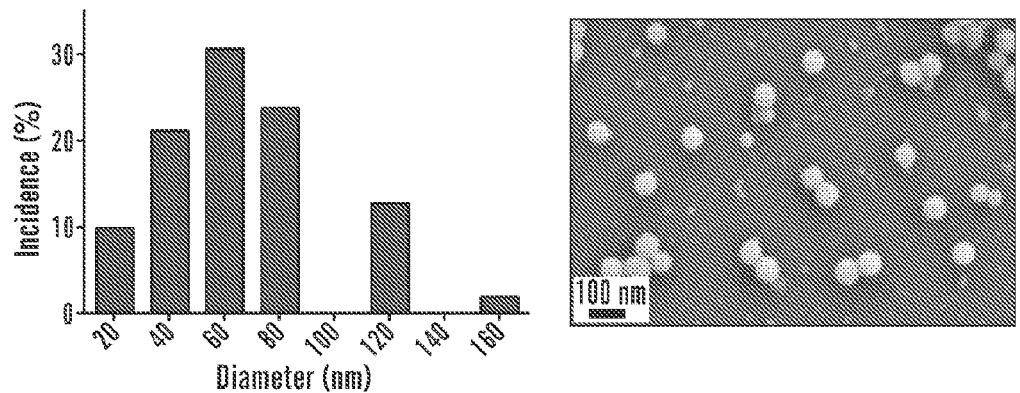
FIGS. 12-12C show DLS size analysis (left) and SEM micrograph (right) of PGC-Pax-Rho (37 mol % Pax, 3 mol % Rho) NPs (FIG. 12A), 43% PGC-Pax+5 wt % Pax NPs (FIG. 12B) and 50/50 43% PGC-Pax/PLGA NPs (FIG. 12C).

By DLS, PGC-Bn and PGC-Pax NPs are approximately 60-80 nm in diameter (N=2-3; FIG. 10A). As Pax loading increases, there is a trend suggesting that NP size also increases, but not significantly. PGC-Bn and PGC-Pax NPs are fairly monodisperse, with PDIs between 0.07 and 0.12 (FIG. 10B). Due to the negative charge of the SDS surface coating, these particles have zeta potentials in the range of −45 to −55 mV (FIG. 10C). By SEM, PGC-Bn NPs appear larger than what is measured in solution (FIG. 11A), likely as a result of particle aggregation which occurs as the particles are drying prior to imaging. While PGC-Pax is a solid polymer, PGC-Bn is a viscous, amorphous polymer, rendering it more prone to aggregation. Average PGC-Pax NP sizes appear to be 70-80 nm by SEM, in accordance with DLS measurements (FIGS. 11B-11E). NPs have been synthesized with up to 16 mg/mL conjugated Pax loadings, compared to the 6 mg/mL pharmaceutical formulation of Pax in C/E (Bristol-Myers Squibb). PGC-Pax-Rho (37 mol % Pax, 3 mol % Rho) NPs were also formulated for uptake studies. These particles are 70.74 nm in diameter with a PDI of 0.051 (N=1; FIG. 12A).

Figure 12B:
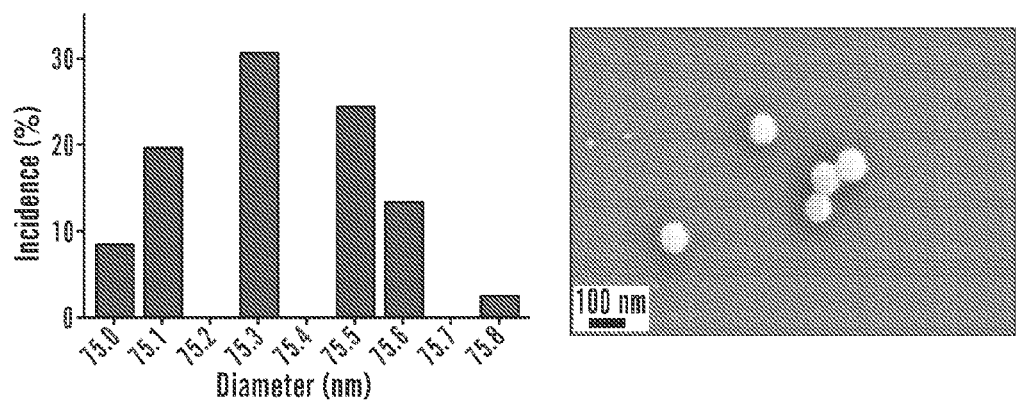

Additionally, we have synthesized SDS-coated PGC-Pax NPs with encapsulated free Pax. 43% PGC-Pax NPs with 5 wt % physically entrapped free Pax (43% PGC-Pax+5 wt Pax NPs) have an average diameter of 75.34 nm, with a PDI of 0.067 and a zeta potential of −45.67 mV (N=1; FIG. 12B). These particles have an encapsulation efficiency (EE) of 81.73%. 37% PGC-Pax NPs were also formulated with 5 wt % physically entrapped free Pax (37% PGC-Pax+5 wt % Pax NPs). These nanocarriers have an average diameter of 85.24 nm, with a PDI of 0.056 and an EE of 100% (N=1).

Figure 12C:
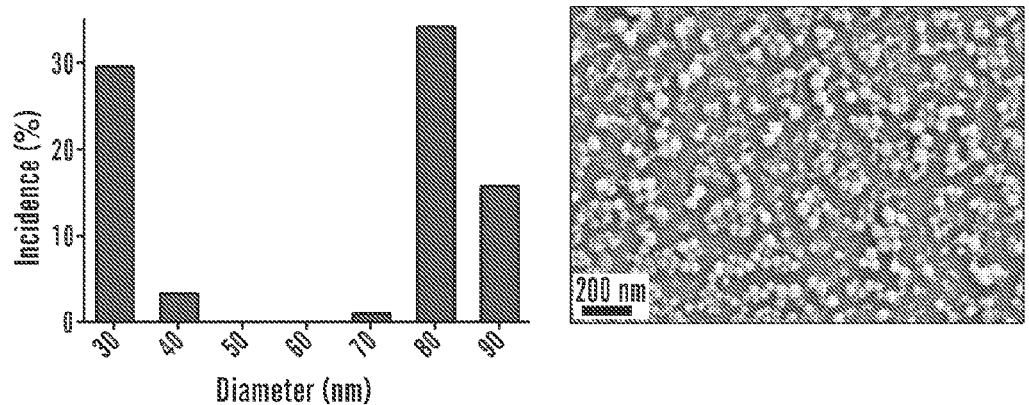

PLGA (MW 30-60 kDa) was used in combination with PGC-Pax to formulate "blended polymer" NPs with SDS surface coatings. NPs were synthesized from 50/50 43% PGC-Pax/PLGA (N=1; FIG. 12C) as well as 20/80 43% PGC-Pax/PLGA (N=1). These particles have average diameters of 71.01 and 79.66 nm, PDIs of 0.125 and 0.146, and zeta potentials of −47.00 and −49.66 mV, respectively. Although the average diameter of these NPs was not different from that of the "base" PGC-Pax NP formulations, the heterogeneity of the NP populations, as indicated by increased PDIs, increased with the incorporation of PLGA. This is expected since varying degrees of polymer mixing will be present in each NP, with few, but perhaps some, particles consisting of PLGA or PGC-Pax only, for example.

Figure 13:
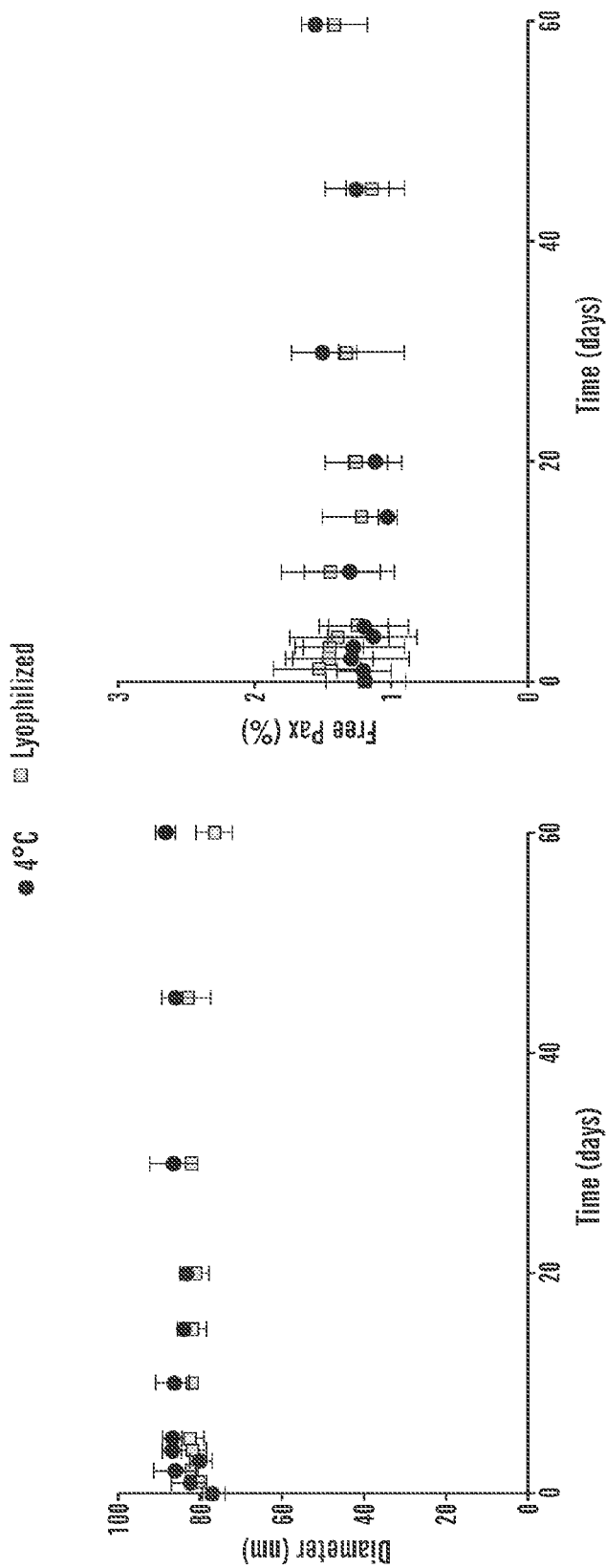
FIG. 13 shows DLS size analysis (left) and HPLC free Pax quantitation (right) of 39% PGC-Pax NPs stored at 4° C. or lyophilized, stored at −20° C., and resuspended in phosphate buffer for analysis at given time-points.

An important parameter in the characterization of NP formulations is their storage stability. Thus, the inventors assessed the NP storage stability for colloidal solutions stored at 4° C., as well as for NPs which are lyophilized, stored at −20° C., and resuspended in solution for use at later time-points. 39% PGC-Pax NPs were synthesized, and either stored at 4° C. or divided into 50 µL aliquots, lyophilized, and stored at −20° C. At later time points, lyophilized particles were resuspended in 10 mM pH 7.4 phosphate buffer and diameter was measured via DLS. Particle size of NPs stored at 4° C. was also measured over time. Both sets of particles were analyzed for free Pax content via HPLC in order to ensure that Pax cleavage does not occur under storage conditions. Over the course of 60 days, NPs stored in solution, as well as lyophilized NPs, maintained their size. Free Pax content also remained at approximately 1% of the total Pax loading (FIG. 13).

PGC-Pax-Rho NP Uptake in MDA-MB-231 Cells

Figure 14A:
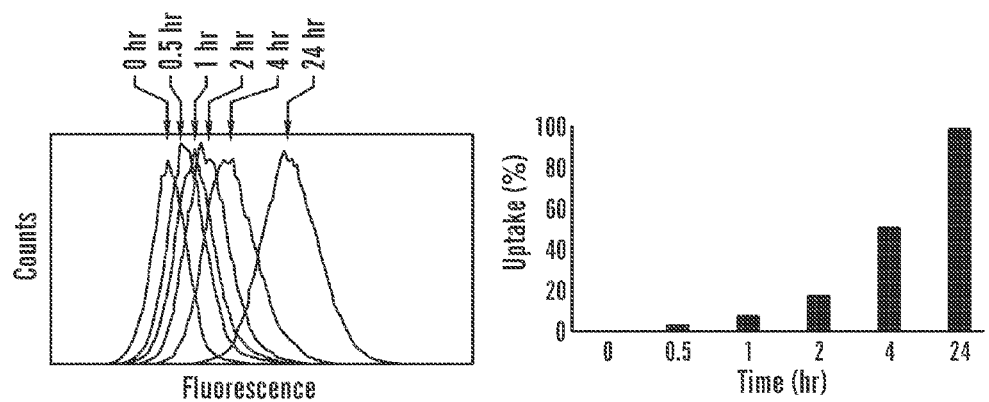
FIG. 14A shows uptake of PGC-Pax-Rho NPs in MDA-MB-231 cells as quantified by flow cytometry. Percent uptake denotes that cells have taken up particles from the population counted.
Figure 14B:
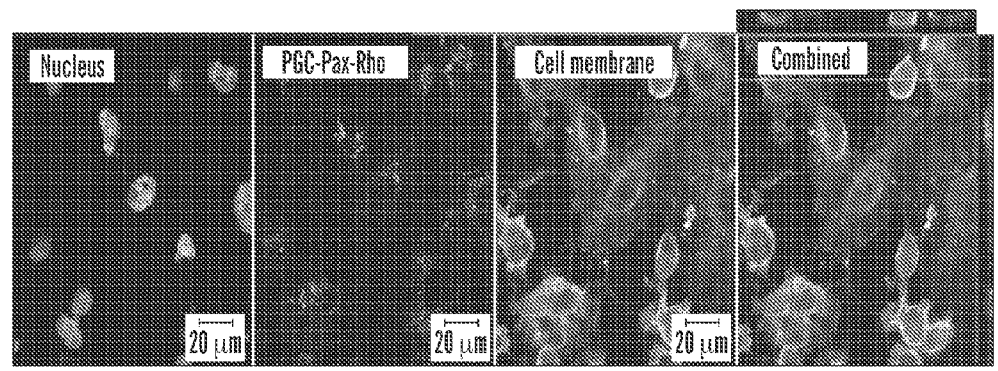
FIG. 14B shows confocal microscopy photographs confirming confirms uptake of PGC-Pax-Rho NPs at 24 hours. Cells were co-stained with Hoechst and Concanavalin-A to mark the nucleus and cell-membrane, respectively. PGC-Pax-Rho NPs are observed within the cell.

To evaluate NP cellular uptake, the intentors synthesized PGC-Pax-Rho NPs with 37 mol % Pax, and 3 mol % Rho. MDA-MB-231 triple negative breast cancer cells were first treated with 37% PGC-Pax NPs, and viability was assessed after 24 hours of incubation. From this experiment, we determined the maximum NP content (~100 ng/mL Pax equivalent) that can be used to assess NP uptake, without inducing cell death at a maximal incubation time of 24 hours. MDA-MB-231 cells were then treated with PGC-Pax-NPs for 0.5, 1, 2, 4, and 24 hours, and uptake was quantified via flow cytometry (FIG. 14A). By 24 hours, nearly 100% of the cell population has taken up particles. The same experiment was repeated using confocal microscopy. After 24 hours of incubation, PGC-Pax NPs can be visualized in the cell cytoplasm (FIG. 14B).

In Vitro Activity of PGC-Pax NPs

Figure 15:
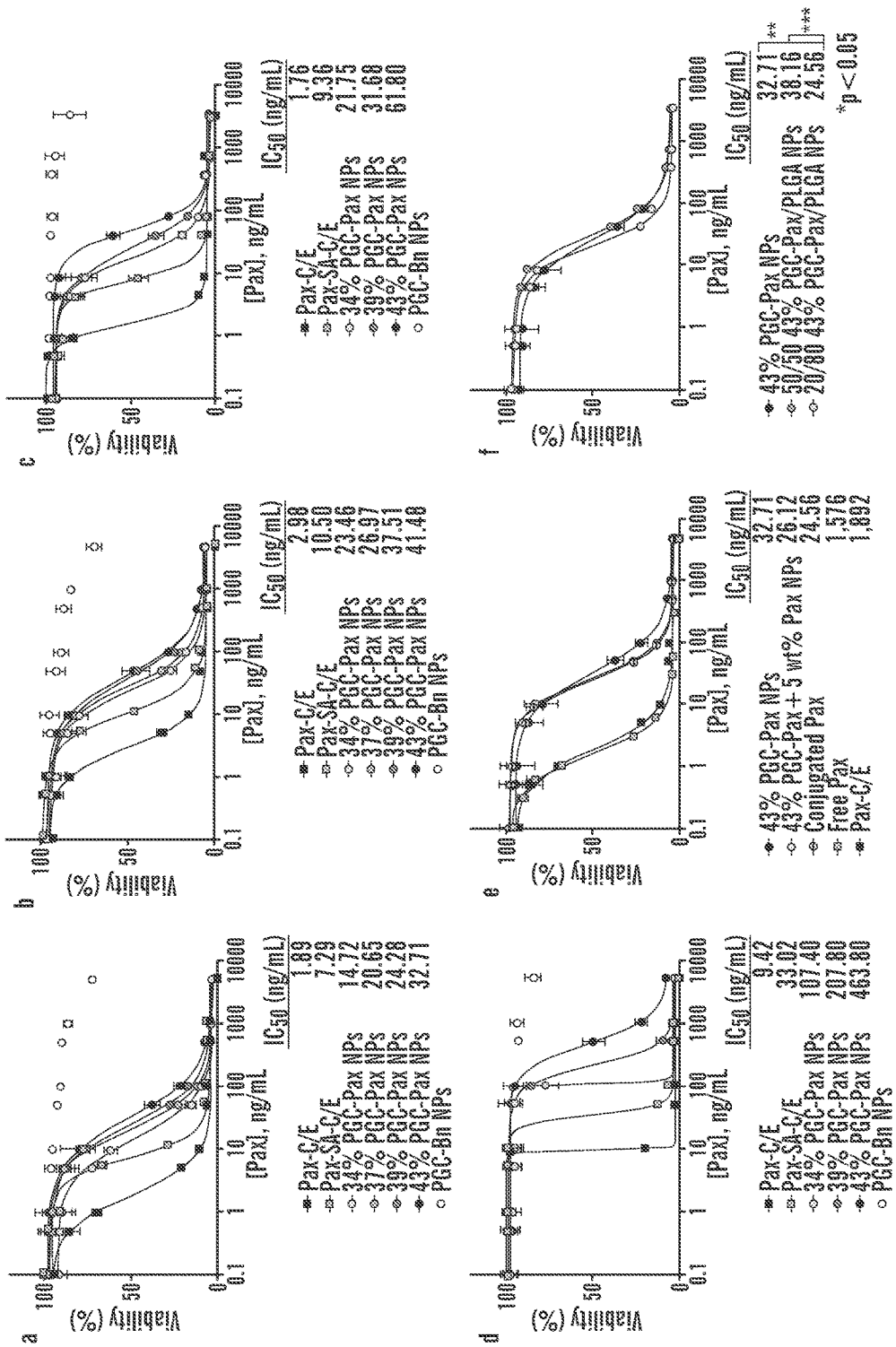
FIGS. 15A-15D show in vitro cytotoxicity analysis of PGC-Pax NP formulations with varying Pax loadings (in mol %), PGC-Bn, NPs, Pax-C/E, and Pax-SA-C/E in MDA-MB-231 (FIG. 15A), Panc1 ((FIG. 15B), A549 (FIG. 15C), and MSTO-211H cells (FIG. 15D).
FIG. 15E shows cytotoxicity analysis of 43% PGC-Pax+5 wt % Pax NPs in MDA-MB-231 cells.
FIG. 15F shows cytotoxicity analysis of 43% PGC-Pax/ PLGA polymer blend NPs in MDA-MB-231 cells.

The in vitro cytotoxicity of SDS-coated PGC-Pax NPs was evaluated in MDA-MB-231 cells (FIG. 15A), Panc1 pancreatic cancer cells (FIG. 15B), A549 lung cancer cells (FIG. 15C), and MSTO-211H mesothelioma cancer cells (FIG. 15D). Cells were plated on day 1, allowed to attach overnight, and then treated with either PGC-Pax NPs, PGC-Bn NPs (vehicle control), Pax-C/E (positive control), or Pax-SA-C/E (conjugate control). Cells were incubated with the treatments for 5 days, and then viability was assessed using an MTS assay according to previously published procedures. By conjugating Pax to succinic acid at the 2' hydroxyl required for tubulin binding (Pax-SA-C/E), we reduce the in vitro potency of the agent by requiring the additional cleavage of Pax into its active form. These data supports our findings that in vitro treatment potency is proportional to the rate of drug cleavage and release. It is evident that PGC-Pax NPs achieve slow drug release since the potencies of the NP formulations are lower, as indicated by higher $IC_{50}$ values, than that of Pax-C/E after 5 days of treatment. Furthermore, as we previously hypothesized, the in vitro potency is inversely proportional to the hydrophobicity of the NP core, which increases with increasing Pax loading.

SDS-coated 43% PGC-Pax+5 wt % Pax NPs also demonstrated significantly increased potency as compared to 43% PGC-Pax NPs when used to treat MDA-MB-231 cells for 5 days (FIG. 15E). By separately analyzing the cell viability data for conjugated Pax as well as free Pax, we can qualitatively evaluate the extent of free Pax and conjugated Pax release. Free Pax has similar potency to Pax-C/E (no statistical difference), indicating that the encapsulated free Pax is released in its entirety within the 5 day incubation period. The conjugated Pax demonstrates statistically increased potency compared to the 43% PGC-Pax formulation, supporting our hypothesis that the diffusion of free Pax from the polymer core facilitates that cleavage and release of conjugated Pax.

MDA-MB-231 cells were similarly treated with SDS-coated 50/50 43% PGC-Pax/PLGA NPs and 20/80 43% PGC-Pax/PLGA NPs for 5 days (FIG. 15F). 50/50 43% PGC-Pax/PLGA NPs do not exhibit increased potency as compared to 43% PGC-Pax NPs. However, reducing the proportion of 43% PGC-Pax to PLGA to 20:80 significantly increased the potency of the NP formulation compared to the 43% PGC-Pax NP treatment, supporting our hypothesis that the incorporation of additional polymers can reduce the hydrophobicity of the NP core and therefore increase drug release as indicated by higher potency in a 5 day cell viability assay.

In Vivo Evaluation of PGC-Pax NPs

Figure 16:
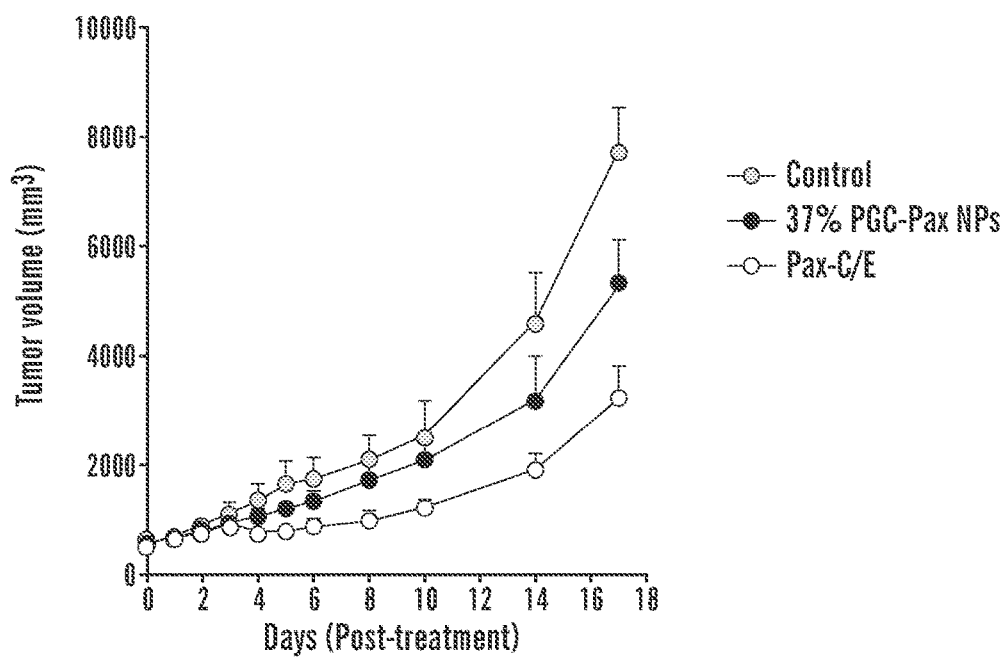
FIG. 16 shows in vivo analysis of 37% PGC-Pax NPs in a subcutaneous model of glioblastoma. When tumors reached 500 mm$^3$, rats (N=3 per group) received one 50 μL intratumoral injection of saline, 0.8 mg Pax equivalent 37% PGC-Pax NPs, or 0.8 mg Pax-C/E.

37% PGC-Pax NPs were evaluated in vivo in a subcutaneous GBM rat model (FIG. 16). When tumors reached 500 $mm^3$ in volume, animals (N=3 per group) received one intratumoral dose of either saline, 0.8 mg Pax as PGC-Pax NPs, or 0.8 mg Pax as Pax-C/E. Without wishing to be bound by a theory, in a cancer as aggressive as GBM, a combination of fast and slow drug release can be more effective for controlling initial tumor growth and subsequently leading to tumor regression. The inventors are evaluating the efficacy of 37% PGC-Pax+5 wt % Pax NPs in this animal model.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A linear, comb, branched, or dendrite oligomer or polymer comprising the following formula:

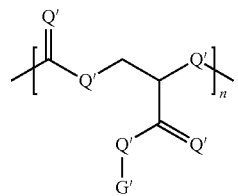

wherein each Q' is independently selected from among: O, S, Se, or NH;
wherein each G' is independently is independently selected from the following structures:

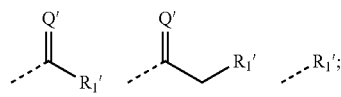

and
wherein $R_1'$ is selected from among hydrogen, a straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, succinyl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents, poly(ethylene glycol), poly(ethylene oxide), poly (hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor, a photocrosslinkable or ionically crosslinkable group;
wherein n is selected from an integer of 1-1,000; and
wherein each polymeric terminal group is selected from among amines, thiols, amides, phosphates, sulphates, hydroxides, metals, alkanes, alkenes, and alkynes.

2. The polymer of claim 1, wherein Q' is O.
3. The polymer of claim 1, wherein $R'_1$ is selected from among hydrogen or a straight or branched alkyl, cycloalkyl, aryl, olefin, silyl, alkylsilyl, arylsilyl, alkylaryl or arylalkyl chain of 2-50 carbons, wherein each alkyl, cycloalkyl, succinyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.
4. The polymer of claim 1, wherein $R'_1$ is selected from among hydrogen or a straight or branched alkyl, cycloalkyl, aryl, olefin, silyl, alkylsilyl, arylsilyl, alkylaryl or arylalkyl chain of 3-50 carbons.
5. The polymer of claim 1, wherein $R'_1$ is selected from among hydrogen or a straight or branched alkyl, alkylaryl or arylalkyl chain of 3-50 carbons.
6. The polymer of claim 1, wherein G' is

7. The polymer of claim 6, wherein Q' is O.
8. The polymer of claim 6, wherein $R'_1$ is selected from among hydrogen or a straight or branched alkyl, cycloalkyl, aryl, olefin, silyl, alkylsilyl, arylsilyl, alkylaryl or arylalkyl chain of 3-50 carbons.
9. The polymer of claim 6, wherein $R'_1$ is selected from among hydrogen or a straight or branched alkyl, alkylaryl or arylalkyl chain of 3-50 carbons.
10. The polymer of claim 1, wherein pharmaceutical agent is conjugated via a succinic acid moiety to between 5 and 95% of the available primary hydroxyl of the polymer back bone.
11. A polymeric film, sheet, mesh, foam, fiber, or particle comprising a polymer of claim 1.
12. A composition comprising a polymer of claim 1.
13. A biodegradable plastic for consumer goods comprising a polymer of claim 1.
14. A copolymer or polymer blend comprising a polymer of claim 1.
15. A cross-linked gel comprising a polymer of claim 1.
16. A superabsorbent polymer, detergent, adhesive, dispersant, or cosmetic comprising a cross-linked gel of claim 15.
17. A method comprising:
applying a polymeric film, sheet, mesh, foam, fiber, or particle of claim 11 to a surgical resection margin or within a treated or untreated tumor or cavity, or to target sites of disease away from the surgical margin.
18. A method comprising:
applying a polymeric film, sheet, mesh, foam, fiber, or particle of claim 11 to a tissue site, wherein the polymeric film, sheet, mesh, foam, fiber, or particle is secured to the tissue site.
19. A method comprising:
applying a polymeric film, sheet, mesh, foam, fiber, or particle of claim 11 to a surgical resection margin or within a treated or untreated tumor or cavity, or to target sites of disease away from the surgical margin; and
delivering an active agent to the surgical resection margin or the treated or untreated tumor or cavity, or the target sites of disease away from the surgical margin.
20. A method for treating cancer comprising administering a composition comprising a polymer of claim 1 and an agent to a subject in need thereof.

* * * * *